US007265264B2

(12) United States Patent
Neff

(10) Patent No.: US 7,265,264 B2
(45) Date of Patent: Sep. 4, 2007

(54) GENE FOR A DOF TRANSCRIPTION FACTOR CAPABLE OF ALTERING THE SIZE AND STATURE OF A PLANT

(75) Inventor: Michael M. Neff, St. Louis, MO (US)

(73) Assignee: Washington University, St. Louis, MO (US)

( * ) Notice: Subject to any disclaimer, the term of this patent is extended or adjusted under 35 U.S.C. 154(b) by 256 days.

(21) Appl. No.: 10/650,249

(22) Filed: Aug. 28, 2003

(65) Prior Publication Data

US 2004/0045055 A1 Mar. 4, 2004

Related U.S. Application Data

(60) Provisional application No. 60/406,657, filed on Aug. 28, 2002.

(51) Int. Cl.
*C12N 15/29* (2006.01)
*C12N 15/82* (2006.01)
*C12N 5/04* (2006.01)
*A01H 5/00* (2006.01)
*A01H 5/10* (2006.01)

(52) U.S. Cl. .............. 800/278; 800/298; 800/287; 800/286; 800/290; 800/320; 800/317; 435/419; 435/320.1

(58) Field of Classification Search ............. 800/290, 800/298, 286, 287, 278, 320, 317; 435/320.1, 435/410, 419
See application file for complete search history.

(56) References Cited

U.S. PATENT DOCUMENTS

| 4,987,071 A | 1/1991 | Cech et al. |
| 5,106,739 A | 4/1992 | Comai et al. |
| 5,107,065 A | 4/1992 | Shewmaker et al. |
| 5,116,742 A | 5/1992 | Cech et al. |
| 5,254,800 A | 10/1993 | Bird et al. |
| 5,880,330 A | 3/1999 | Weigel et al. |
| 6,297,429 B1 | 10/2001 | Takatsuji et al. |
| 2004/0006797 A1 | 1/2004 | Shi et al. |

FOREIGN PATENT DOCUMENTS

WO WO 02/055658 A2 7/2002

OTHER PUBLICATIONS

Papi et al (2002, Plant Physiology 128:411-417).*
Colliver et al (1997, Plant Mol. Biol. 35:509-522).*
Emery et al (2003, Current Biology 13:1768-1774).*
Bowie et al, Science 247:1306-1310, 1990.*
McConnell et al, Nature 411 (6838):709-713, 2001.*
Faske et al (1997, Plant Physiol. 115:705-715).*
Benes, V., et al., "NCBI Database for Nucleotide Sequences," *National Center for Biotechnology Information*, National Library of Medicine, 2000, Accession No. AL132975, Bethesda, MD, USA.

PCT International Search Report for PCT Patent Application PCT/US03/26784, Jan. 5, 2005, 7 pages, US Patent Office, Baum, S.
Bevan, M., "Binary *Agrobacterium* vectors for plant transformation," Nucl Acids Res, 1984, pp. 8711-8721, vol. 12(22), IRL Press Limited, Oxford, England.
Bitter, G.A., et al., "Expression and Secretion Vectors for Yeast," Methods in Enzymology, 1987, pp. 516-544, vol. 153, Academic Press, Inc.
Bower, R., et al., "Transgenic sugarcane plants via microprojectile bombardment," The Plant J, 1992, pp. 409-416, vol. 2(3), BIOS Scientific Publishers Ltd., Blackwell Scientific Publications, Oxford, England.
Brisson, N., et al., "Expression of a bacterial gene in plants by using a viral vector," Nature, Aug. 9, 1984, pp. 511-514, vol. 310.
Broglie, R., et al., "Light-Regulated Expression of a Pea Ribulose-1,5-biphosphate Carboxylase Small Subunit Gene in Transformed Plant Cells," Science, May 25, 1984, pp. 838-843, vol. 224(4651), American Association for the Advancement of Science.
Bustos, M.M., "Positive and negative *cis*-acting DNA domains are required for spatial and temporal regulation of gene expression by a seed storage protein promoter," EMBO J, 1991, pp. 1469-1479, vol. 10(6), Oxford University Press.
Bytebier, B., et al., "TDNA organization in tumor cultures and transgenic plants of the monocotyledon *Asparagus officinalis*," PNAS, 1987, pp. 5345-5349, vol. 84, National Academy of Sciences.
Caddick, M.X., et al., "An Ethanol inducible gene switch for plants used to manipulate carbon metabolism," Nature Biotechnology, Feb. 1998, pp. 177-180, vol. 16.
Casas, A.M., et al., "Transgenic sorghum plants via microprojectile bombardment," PNAS, Dec. 1993, pp. 11212-11216, vol. 90, National Academy of Sciences.
Chilton, —D., et al., "Stable Incorporation of Plasmid DNA into Higher Plant Cells: the Molecular Basis of Crown Gall Tumorigenesis," Cell, Jun. 1977, pp. 263-271, vol. 11, MIT.
Christou, P., et al., "Production of transgenic rice (*Oryza sativa L.*) plants from agronomically important *indica* and *japonica* varieties via electric discharge particle acceleration of exogenous DNA into immature zygotic embryos," Bio/Technology, 1991, pp. 957-962, vol. 9, Nature Publishing Company, New York, New York.
Christou, P., et al., "The Biotechnology of Crop Legumes," Euphytica, 1994, pp. 165-185, vol. 74.
Cooney, M., et al., "Site-Specific Oligonucleotide Binding Represses Transcription of the Human c-myc Gene in vitro," Science, Jul. 22, 1988, pp. 456-459, vol. 241 (4864), American Society for the Advancement of Science.

(Continued)

*Primary Examiner*—Stuart F. Baum
(74) *Attorney, Agent, or Firm*—Senniger Powers

(57) ABSTRACT

A transgenic plant transformed by a Dof transcription factor, OBP3, coding nucleic acid, wherein expression of the nucleic acid sequence in the plant results in an alteration in the size of the resulting plant as compared to a corresponding wild-type variety of plant. Also provided are agricultural products, including seeds, produced by the transgenic plants. Further provided are isolated OBP3's, isolated nucleic acid coding OBP3's, and vectors and host cells containing the latter.

18 Claims, 15 Drawing Sheets

OTHER PUBLICATIONS

Coruzzi, G., et al., "Tissue-specific and light-regulated expression of Spea nuclear gene encoding the small subunit of ribulose-1,5-bisphosphate carboxylase," EMBO J, 1984, pp. 1671-1679, vol. 3(8), IRL Press Ltd., Oxford, England.

Crossway, A., et al., "Transformation of tobacco protoplasts by direct DNA microinjection," Mol. Gen., 1986, pp. 179-185, vol. 202.

Croy, E.J., et al., "Chapter 2 Plant Nucleic Acids," Plant Molecular Biology LabFax, 1993, pp. 21-48, R.R.D. Croy, ed., BIOS Scientific Publishers Ltd., Oxford, England.

De Block, M., et al., "Expression of foreign gees in regenerated plants and in their progeny," EMBO J., 1984, pp. 1681-1689, vol. 3(8), IRL Press Ltd., Oxford, England.

de Framond, A.J., et al., "Mini-Ti: A New Vector Strategy for Plant Genetic Engineering," Bio/Technology, May 1983, pp. 262-269, Nature Publishing Company, New York, New York.

De Paolis, A., et al., "A *rolB* regulatory factor belongs to a new class of single zinc finger plant proteins," The Plant J, 1996, pp. 215-223, vol. 10(2), BIOS Scientific Publishers Ltd., Blackwell Scientific Publications, Oxford, England.

de la Peña, A., et al., "Transgenic rye plants obtained by injecting DNA into young floral tillers," Nature, Jan. 15, 1987, pp. 274-276, vol. 325.

Delagrave, S., et al., "Recursive ensemble mutagenesis," Prot Eng, 1993, pp. 327-331, vol. 6(3), Oxford Unversity Press.

Depicker, A., et al., "Nopaline synthase transcript mapping and DNA sequence," J Mol Appl Gen, 1982, pp. 561-573, vol. 1(6), Raven Press, New York.

Doyle, J.J., et al., "The Glycosylated Seed Storage Proteins of *Glycine max* and *Phaseolus vulgaris*," J. Biol. Chem., Jul. 15, 1986, pp. 9228-9238, vol. 261(20).

Fisk, H.J., et al., "The introduction and expression of transgenes in plants," Sci Hort, 1993, pp. 5-36, vol. 55, Elsevier Science Publishers B.V., Amsterdam.

Fraley, R.T., et al. "Lipisome-mediated delivery of tobacco mosaic virus ma into tobacco protoplasts: A sensitive assay for monitoring liposome-protoplast interactions," PNAS, Mar. 15, 1982, pp. 1859-1863, vol. 79(6), National Academy of Sciences.

Fraley, R.T., et al. "Expression of bacterial genes in plant cells," PNAS, Aug. 1, 1983, pp. 4803-4807, Vo. 80(15), National Academy of Sciences.

Fromm, M., et al., "Expression of genes transferred into monocot and dicot plant cells by electroporation," PNAS, Sep. 1, 1985, pp. 5824-5828, vol. 82(17), National Academy of Sciences.

Fromm, M., et al., "Inheritance and Expression of Chimeric Gene in the Progeny of Transgenic Maize Plants," Bio/Technology, Sep. 1990, pp. 833-839, vol. 8, Nature Publishing Company, New York, New York.

Gasser, C.S., et al., "Genetically engineered plants for crop improvement," Science, Jun. 16, 1989, pp. 1293-1299, vol. 244, American Society for the Advancement of Science.

Gielen, J., et al., "The complete nucleotide sequence of the TL-DNA of the *Agrobacterium tumefaciens* plasmid pTiAch5," EMBO J, 1984, pp. 835-846, vol. 3(4), IRL Press Limited, Oxford, England.

Gordon-Kamm, W.J., et al., "Transformation of Maize Cells and Regeneration of Fertile Transgenic Plants," Plant Cell, Jul. 1990, pp. 603-618, vol. 2.

Gowda, S., et al., "Identification of Promoter Sequences for the Major RNA Transcripts of Figwort Mosaic and Peanut Chlor Streak Viruses (*Caulimovirus* Group)," J Cell Biochem, 1989, pp. 301, Supplement 13D, UCLA Symposia on Molecular & Cellular Biology (Abstract M318).

Gurley, et al., "Upstream Sequences Required for Efficient Expression of a Soybean Heat Shock Gene," Mol Cell Biol, Feb. 1986, pp. 559-565, vol. 6(2).

Hajdukiewicz, P., et al., "The small, versatile *pPZP* family of *Agrobacterium* binary vectors for plant transformation," Plant Mol Biol, 1994, pp. 989-994, vol. 25, Kluwer Academic Publishers, Belgium.

Haseloff, J., et al., "Simple RNA enzymes with new and highly specific endoribonuclease activities," Nature, Aug. 18, 1988, pp. 585-591, vol. 334.

Hempel, F.D., et al., "Floral determination and expression of floral regulatory genes in *Arabidopsis*," Development, 1997, pp. 3845-3853, vol. 124, The Company of Biologists Limited, Great Britain.

Hershey, H.P., et al., "Isolation and characterization of cDNA clones for RNA species induced by substituted benzenesulfonamides in corn," Plant Mol Biol, 1991, pp. 679-690, vol. 17, Kluwer Academic Publishers, Belgium.

Hoekema, A., et al., "A binary plant vector strategy based on separation vir- and T-region of the *Agrobacterium tumefaciens* Ti-plasmid," Nature, May 12, 1983, pp. 179-180, vol. 303.

Hooykaas-Van Slogteren, G.M.S., et al., "Expression of Ti plasmid genes in monocotyledonous plants infected with *Agrobacterium tumefaciens*," Nature, Oct. 25, 1984, pp. 763-764, vol. 311.

Horn, M.E., et al., "Transgenic plants of Orchardgrass (*Dactylis glomerata* L.) from protoplasts," Plant Cell Reports, 1988, pp. 469-472, vol. 7(7).

Horsch, R.B., et al., "A Simple and General Method for Transferring Genes into Plants," Science, Mar. 8, 1985, pp. 1229-1231, vol. 227(4691), American Society for the Advancement of Science.

Ike, Y., et al., "Solid phase synthesis of polynucleotides. VIII. Synthesis of mixed oligodeoxyribonucleotides by the phosphotriester solid phase method[1]," Nucl Acids Res, 1983, pp. 477-488, vol. 11(2).

Itakura, K., et al., "Expression in *Escherichia coli* of a Chemically Synthesized Gene for the Hormone Somatostatin," Science, Dec. 9, 1977, pp. 1056-1063, vol. 198(4321), American Society for the Advancement of Science.

Itakura, K., et al., "Synthesis and use of synthetic oligonucleotides," Annual Rev Biochem, 1984, pp. 323-356, vol. 53, Annual Reviews, Inc., Palo Alto, California.

Ito, M., et al., "Meristem-specific gene expression directed by the promoter of the S-phase-specific gene, *cyc07*, in transgenic *Arabidopsis*," Plant Mol Biol, 1994, pp. 863-878, vol. 24, Kluwer Academic Publishers, Belgium.

Jack, T., et al., "*Arabidopsis* Homeotic Gene *APETALA3* Ectopic Expression: Transcriptional and Postranscriptional Regulation Determine Floral Organ Identity," Cell, Feb. 25, 1994, pp. 703-716, vol. 76.

Kakimoto, T., "CKI1, a Histidine Kinase Homolog Implicated in Cytokinin Signal Transduction," Science, Nov. 8, 1996, pp. 982-985, vol. 274(5289), American Society for the Advancement of Science.

Kang, H-G, et al., "Characterization of salicylic acid-responsive, *Arabidopsis* Dof domain proteins: overexpression of OBP3 leads to growth defects," The Plant J, 2000, pp. 329-339, vol. 21(4), BIOS Scientific Publishers Ltd., Blackwell Scientific Publications, Oxford, England.

Klee, H., et al., "*Agrobacterium*-mediated Plant Transformation and its Further Applications to Plant Biology," Ann. Rev. Plant Physiol., 1987, pp. 467-486, vol. 38, Annual Reviews Inc., Palo Alto, California.

Klein, T.M., et al., "High-velocity microprojectiles for delivering nucleic acids into living cells," Nature, May 7, 1987, pp. 70-73, vol. 327, Nature Publishing Group.

Knutzon, D.S., et al., "Modification of *Brassica* seed oil by antisense expression of a stearoyl-acyl carrier protein desaturase gene," PNAS, Apr. 1992, pp. 2624-2628, vol. 89, National Academy of Sciences.

Koziel, M.G., et al., "Field Performance of Elite Transgenic Maize Plants Expressing an Insecticidal Protein Derived from *Bacillus thuringiensis*," Bio/Technology, Feb. 11, 1993, pp. 194-200, vol. 11, Nature Publishing Company, New York, New York.

Krens, F.A., et al., "In vitro transformation of plant protoplasts with Ti-plasmid DNA," Nature, Mar. 4, 1982, pp. 72-74, vol. 296, Nature Publishing Group.

Lam, E., et al., "GT-1 Binding Site Confers Lights Responsive Expression in Transgenic Tobacco," Science, Apr. 27, 1990, pp. 471-474, vol. 248(4954), American Society for the Advancement of Science.

Lawton, M.A., et al., "Expression of soybean β-conclycinin gene under the control of the Cauliflower Mosaic Virus 35S and 19S promoters in transformed petunia tissues," Plant Mol Biol, 1987, pp. 315-324, vol. 9, Matinus Nijhoff Publishers, Dordrecht, The Netherlands.

Lörz, H., et al., "Gene transfer to cereal cells mediated by protoplast transformation," Mol Gen Genet, 1985, pp. 178-182, vol. 199, Springer International.

Luo, Z-X., et al., "A Simple Method for the Transformation of Rice Via the Pollen-Tube Pathway," Plant Mol Biol Reporter, 1988, pp. 165-174, vol. 6(3).

Martinez, M.C., et al., "Spatial pattern of cdc2 expression in relation to meristem activity and cell proliferation during plant development," PNAS, Aug. 1992, pp. 7360-7364, vol. 89, National Academy of Sciences.

Medford, J.I., et al., "Molecular Cloning and Characterization of Genes Expressed in Shoot Apical Meristems," The Plant Cell, Apr. 1991, pp. 359-370, vol. 3.

Mett, V.L., et al., "Copper-controllable gene expression system for whole plants," PNAS, May 1993, pp. 4567-4571, vol. 90, National Academy of Sciences.

Mol, J.N.M., et al., "Regulation of plant gene expression by antisense RNA," FEBS Letter, Aug. 1990, pp. 427-430, vol. 268(2), Elsevier Science Publishers B.V., Amsterdam.

Moser, H.E., et al., "Sequence-Specific Cleavage of Double Helical DNA by Triple Helix Formation," Science, Oct. 30, 1987, pp. 645-650, vol. 238, American Society for the Advancement of Science.

Nagel, R., et al., "Electroporation of binary Ti plasmid vector into Agrobacterium tumefaciens and Agrobacterium rhizogenes," FEMS Microbiology Letters, 1990, pp. 325-328, vol. 67(3), Elsevier Science Publishers, Amsterdam.

Narang, S.A., "DNA Synthesis," Tetrahedron, 1983, pp. 3-22, vol. 39(1), Pergamon Press, Oxford, England.

Neff, M.M., et al., "Genetic Interactions between Phytochrome A, Phytochrome B, and Cryptochrome 1 during Arabidopsis Development[1]," Plant Physiol, 1998, pp. 27-36, vol. 118, American Society of Plant Physiologists, Rockville, MD.

Neff, M.M., et al., "BAS1: A gene regulating brassinosteroid levels and light responsiveness in Arabidopsis," PNAS, Dec. 21, 1999, pp. 15316-15323, vol. 96(26), National Academy of Sciences.

Neff, M.M., et al., "Light: an indicator of time and place," Genes & Development, 2000, pp. 257-271, vol. 14, Cold Spring Harbor Press.

Odell, J.T., et al., "Identification of DNA sequences required for activity of the cauliflower mosaic virus 35S promoter," Nature, Feb. 28, 1985, pp. 810-815, vol. 313.

Ou-Lee, T-M, et al., "Expression of a foreign gene linked to either a plant-virus or a Drosophila promoter, after electroporation of protoplasts of rice, wheat, and sorghum," PNAS, Sep. 1986, pp. 6815-6819, vol. 83, National Academy of Sciences.

Papi, M., et al., "Identification and disruption of an Arabidopsis zinc finger gene controlling seed germination," Genes & Development, 2000, pp. 28-33, vol. 14, Cold Spring Harbor Laboratory Press.

Papi, M., et al., "Inactivation of the Phloem-Specific Dof Zinc Finger Gene DAG1 Affects Response to Light and Integrity of the Testa of Arabidopsis Seeds[1]," Plant Physiol, Feb. 2002, pp. 411-417, vol. 128, American Society of Plant Physiologists, Rockville, MD.

Peng, J., et al., "Green Revolution' genes encode mutant gibberellin response modulators," Nature, Jul. 15, 1999, pp. 256-261, vol. 400.

Plesch, G., et al., "Involvement of TAAAG elements suggests a role for Dof transcription factors in guard cell-specific gene expression," The Plant J, 2001, pp. 455-464, vol. 28(4), BIOS Scientific Publishers Ltd., Blackwell Scientific Publications, Oxford, England.

Praseuth, D., et al., "Sequence-specific binding and photocrosslinking of α and β oligodeoxynucleotides to the major groove of DNA via triple-helix formation," PNAS, Mar. 1988, pp. 1349-1353, vol. 85, National Academy of Sciences.

Reed, J.W., et al., "Mutations in the Gene for the Red/Far-Red Light Receptor Phytochrome B Alter Cell Elongation and Physiological Responses throughout Arabidopsis Development," The Plant Cell, Feb. 1993, pp. 147-157, vol. 5.

Richins, R.D., et al., "Sequence of figwort mosaic virus DNA (caulimovirus group)," Nucleic Acids Research, 1987, pp. 8451-8466, vol. 15(20), Oxford University Press.

Reichmann, J.L., et al. "A genomic perspective on plant transcription factors," Current Opinion in Plant Biology, 2000, pp. 423-434, vol. 3.

Rhodes, C.A., et al., "Genetically Transformed Maize Plants from Protoplasts," Science, Apr. 8, 1988, pp. 204-207, vol. 240, American Society for the Advancement of Science.

Ruvkun, G.B., et al., "A general method for site-directed mutagenesis in prokaryotes," Nature, Jan. 8, 1981, pp. 85-91, Vo. 289(1).

St. Schell, J., "Transgenic Plants as Tools to Study the Molecular Organization of Plant Genes," Science, Sep. 4, 1987, pp. 1176-1183, vol. 237, American Society for the Advancement of Science.

Schena, M., et al., "A steroid-inducible gene expression system for plant cells," PNAS, Dec. 1991, pp. 10421-10425, vol. 88.

Severin K., et al., "heat-inducible hygromycin resistance in transgenic tobacco," Plant Mol Biol, 1990, pp. 827-833, vol. 15, Kluwer Academic Publishers, Belgium.

Shimamoto, K., et al., "Fertile transgenic rice plants regenerated from transformed protoplasts," Nature, Mar. 16, 1989, pp. 274-276, vol. 338.

Somers, D.A., et al., "Fertile, Transgenic Oat Plants," Bio/Technology, Dec. 1992, pp. 1589-1594, vol. 10, Nature Publishing Company, New York, New York.

Stayton, M., et al., "High-level, Seed-specific Expression of Foreign Coding Sequences in Brassica napus," Aust J Plant Physiol, 1991, pp. 507-517, vol. 18.

Takamatsu, N., et al., "Expression of Bacterial chloramphenicol acetyltransferase gene in tobacco plants mediated by TMV-RNA," EMBO J, 1987, pp. 307-311, vol. 6(2), IRL Press Ltd., Oxford, England.

Tatusov, R.L., et al., "A Genomic Perspective on Protein Families," Science, Oct. 24, 1997, pp. 631-637, vol. 278, American Society for the Advancement of Science.

Terada, R., et al., "A wheat histone H3 promoter confers cell division-dependent and -independent expression of the gus A gene in transgenic rice plants," The Plant J, 1993, pp. 241-252, vol. 3(2), BIOS Scientific Publishers Ltd., Blackwell Scientific Publications, Oxford, England.

Tierney, M.L., et al., "Isolation and characterization of a genomic clone encoding the β-subunit of β-conglycinin," Planta, 1987, pp. 356-363, vol. 172, Springer-Verlag International.

Toriyama, K., et al., "Transgenic Rice Plants After Direct Gene Transfer into Protoplasts," Bio/Technology, Sep. 1988, pp. 1072-1074, vol. 6, Nature Publishing Company, New York, New York.

Vasil, V., et al., "Herbicide Resistant Fertile Transgenic Wheat Plants Obtained by Microprojectile Bombardment of Regenerable Embryogenic Callus," Bio/Technology, Jun. 1992, pp. 667-674, vol. 10, Nature Publishing Company, New York, New York.

Velten, J., et al., "Isolation of a dual plant promoter fragment from the Ti plasmid of Agrobacterium tumefaciens," EMBO J, 1984, pp. 2723-2730, vol. 3(12), IRL Press Ltd., Oxford, England.

Vincente-Carbajosa, J., et al., "A Maize Zinc-Finger Protein Binds the Prolamin Box in Zein Gene Promoters and Interacts with the Basic Leucine Zipper Transcriptional Activator Opaque2," PNAS, Jul. 1997, pp. 7685-7690, vol. 94, The National Academy of Sciences.

Walden, R., et al., "Activation tagging: a means of isolating genes implicated as playing a role in plant growth and development," Plant Mol Biol, 1994, pp. 1521-1528, vol. 26, Kluwer Academic Publishers, Belgium.

Wan, Y., et al., "Generation of Large Numbers of Independently Transformed Fertile Barley Plants[1]," Plant Physiol, 1994, pp. 37-48, vol. 104(1-4), American Society of Plant Physiologists, Rockville, MD.

Wang, Z-Y., et al., "Transgenic Plants of Tall Fescue (Festuca arundinacea Schreb.) Obtained by Direct Gene Transfer to Protoplasts," Bio-Technology, Jun. 1992, pp. 691-696, vol. 10, Nature Publishing Company, New York, New York.

Washio, K., "Identification of Dof proteins with implication in the gibberellin-regulated expression of a peptidase gene following the germination of rice grains," Biochimica et Biophysica Acta, 2001, pp. 54-62, vol. 1520, Elsevier Science Publishers, Amsterdam.

Weeks, J.T., et al., "Rapid Production of Multiple Independent Lines of Fertile Transgenic Wheat (*Triticum aestivum*)[1]," Plant Physiol, 1993, p. 1077-1084, vol. 102, American Society of Plant Physiologists, Rockville, MD.

Weintraub, H., et al., "Anti-Sense RNA as a molecular tool for genetic analysis," TIG, Jan. 1985, pp. 22-25, vol. 1.

Weigel, D., et al., "Activation Tagging in *Arabidopsis*[1]," Plant Physiol, Apr. 2000, pp. 1003-1013, vol. 122, American Society of Plant Physiologists, Rockville, MD.

Wissenbach, M., et al., "*Myb* Genes from *Hordeum vulgare*: tissue-specific expression of chimeric *Myb* promoter/*Gus* Genes in transgenic tobacco," The Plant J, 1993, pp. 411-422, vol. 4(3), BIOS Scientific Publishers Ltd., Blackwell Scientific Publications, Oxford, England.

Yamaguchi-Shinozaki, K., et al., "Analysis of an ABA-responsive rice gene promoter in transgenic tobacco," Plant Mol Biol, 1990, pp. 905-912, vol. 15, Kluwer Academic Publishers, Belgium.

Yanagisawa, S., "A novel DNA-binding domain that may form a single zinc finger motif," Nuc Acids Res, 1995, pp. 3403-3410, vol. 23(17); Oxford University Press.

Yanagisawa, S., "Dof DNA-binding domains of plant transcription factors contribute to multiple protein-protein interactions," Eur. J. Biochem, 1997, pp. 403-410, vol. 250.

Yanagisawa, S., et al., "Involvement of Maize Dof Zinc Finger Proteins in Tissue-Specific and Light-Regulated Gene Expression," The Plant Cell, Jan. 1998, pp. 75-89, vol. 10.

Yanagisawa, S., "Dof1 and Dof2 transcription factors are associated with expression of multiple genes involved in carbon metabolism in maize," The Plant J, 2000, pp. 281-288, vol. 21(3), BIOS Scientific Publishers Ltd., Blackwell Scientific Publications, Oxford, England.

Yanagisawa, S., et al., "Diversity and similarity among recognition sequences of dof transcription factors," The Plant J, 1999, pp. 209-214, vol. 17(2), BIOS Scientific Publishers Ltd., Blackwell Scientific Publications, Oxford, England.

Zambryski, P., et al., "Ti plasmid vector for the introduction of dna into plant cells without alteration of their normal regeneration capacity," EMBO J, 1983, pp. 2143-2150, vol. 2(12), IRL Press Ltd., Oxford, England.

Zhang, H.M., et al., "Transgenic rice plants produced by electroporation-mediated plasmid uptake into protoplasts," Plant Cell Rep, 1988, pp. 379-384, vol. 7(6), Springer International.

Zhang, W., et al., "Efficient regeneration of transgenic plants from rice protoplasts and correctly regulated expression of the foreign gene in the plants," Theor Appl Genet, 1988, pp. 835-840, vol. 76(6), Springer International.

Zhong, H., et al., "Transgenic plants of turfgrass (*Agrostis palustris* Huds.) from microprojectile bombardment of embryogenic callus," Plant Cell Rep, 1993, pp. 1-6, vol. 13(1), Springer International.

Ainley, W.M., et al., "Development of a heat shock inducible expression cassette for plants: Characterization of parameters for its use in transient expression assays," Plant Mol Biol, 1990, pp. 949-967, Kluwer Academic Publishers, Belgium.

Arkin, A.P., et al., "An algorithm for protein engineering: Simulations of recursive ensemble mutagenesis," PNAS, Aug. 1992, pp. 7811-7815, vol. 89, National Academy of Sciences.

Asch, D.K., et al., "Relationship of vector insert size to homologous integration during transformation of *Neurospora crassa* with the cloned *am* (GDH) gene," Mol Gen Genet, 1990, pp. 37-43, vol. 221(1), Springer International.

Asch, D.K., et al., "Analysis of Junction Sequences Resulting From Integration at Nonhomologous Loci in *Neurospora crassa*," Genetics, Apr. 1992, pp. 737-748, vol. 130.

Atanassova, R., et al. "A 126 bp fragment of a plant histone gene promoter confers preferential expression in meristems of transgenic *Arabidopsis*," The Plant J, 1992, pp. 291-300, vol. 2(3), BIOS Scientific Publishers Ltd., Blackwell Scientific Publications, Oxford, England.

Back, E., et al., "Isolation of the spinach nitrite reductase gene promoter which confers nitrate inducibility on GUS gene expression in transgenic tobacco," Plant Mol Biol, 1991, pp. 9-18, vol. 17, Kluwer Academic Publishers, Belgium.

Bartel, D.P., et al., "Isolation of New Ribozymes from a Large Pool of Random Sequences," Science, Sep. 10, 1993, pp. 1411-1418, vol. 261(5127), American Society for the Advancement of Science.

Bechtold, N., et al., "*In-planta Agrobacterium*-mediated gene transfer by infiltration of adult *Arabidopsis thaliana* plants," C R Acad Sci Ser III, 1993, pp. 1194-1199, vol. 316.

Becker, D., et al., "Fertile transgenic wheat from microprojectile bombardment of scutellar tissue," The Plant J, 1994, pp. 299-307, vol. 5(2), BIOS Scientific Publishers Ltd., Blackwell Scientific Publications, Oxford, England.

\* cited by examiner

```
                       SEQUENCE LISTING

<160> NUMBER OF SEQ ID NOS: 20

<210> SEQ ID NO 1
<211> LENGTH: 7580
<212> TYPE: DNA
<213> ORGANISM: Arabidopsis thaliana

<400> SEQUENCE: 1
agctctatta attcaagaga gcagcaaata aagcaaaaac tcaaaaccta agttttctga      60
atatgaaagg ggttagataa tcattctctc aactagttaa aaaaagtaat gataaaatta     120
aaaacacaat ggatcaatta agagacagta gtttatgata tatatggttg ggatcgatta     180
gttgacatca caaagatcaa aataatgacc ggtaattgcc caaataccaa ggcgacaatt     240
catgcgatat tcaaacacct taatgtcatt caaatactat aactaactat cctcaattaa     300
caaagctagc tagattttc tcaagtgagc aacagtctaa ttcttctgaa aaaacttgtt     360
ttttccgagt gtaaattatc caatctactt actacaattt gagcattaat ctagttttct     420
ctgcaacttt aaaaccaggt gtacaagtgt caacaccaga tctagcgtaa aacacttaag     480
ctagtactta aatagattat gcctattttt tcgaccatta tatattaaac tttccagcct     540
ttcgtgaaaa aatgcgcatg ttcttgttgg aatctaggaa tcttcttcta ctaaagattg     600
gcatgcacgt ggtaacgatt tccattgtat actatctcga tattttccca ccttaaatat     660
cttgaaaatt aagatcaaat tatatgagaa catatattgt atcattgttt gtaatagcct     720
tatatagtgt gtagatgtga actatggata caaaaaacaa taggaaagaa aaagctgcag     780
agaaggtgtt gctttacaac tatgaatatg ggctcatgag atgtacacta cagataagcg     840
aagattcctg ttgcatgaaa atgtgttact aataaaaaaa acacatgcac atttctataa     900
agacgaattt cttttaaata ataaatttct ataacaaata aagataagtg ctcctttaaa     960
```

-continued

```
aacatgcaaa agaatatata gatttaccgt atcagatttt catacaattt ttatatttt       1020 tgagcttgaa agattaacat gacaaactgt atcgtgtgtc ctcgtctatt caccoctaga      1080 agaagtgaaa catggaactt tatgtatttg catacggcga gctagcttct tccctacttg      1140
tccaatagat gaagacatta tcactcaggt tcagctactt cgaagcgcaa catatcgaca      1200
aaaaatcgtt ttagctctat catctgtctt ttgaagaaaa atatcaacat atcaaataca     1260
tatacacact ccccacaaat atataaccac aatatatatt ggttactacg aaattccaat     1320
gatattgctc tttgaaacaa ctaaactgtg aattacaagc taaggcaata tatctattat    1380
attctttctt tgtgtctcaa cttcatccct ttctaagtaa ttcaaattaa ttggaagttt    1440
tgtcatctaa attgaagttc ttcttaccgg atcattttgt ctcaggttga tatatacttt    1500
cttagtctga tacgaaaaac ttataaatat aatgattaga gagagacatg tttgatgtta    1560 tattttctg gtaaaaaaca tcttgattat gaactatata gttagggata tgtttgatgt    1620
tgtgtgtcga catagtgagg tccattaaaa agaaggtctg attaaatttt acgtttggac    1680
cacaaatctt tcttttagaa atcgcggact gggacacctt cctacaacat gtccgtcttt    1740
actaatctta cgtaccoctc acattcgtaa ccataaaatc atcaaatata atatagagac    1800
tggtgatcat aattcgaaat atttttcact aattcaatgt tatcggtaag ttatattagg    1860
ggtataacat caagaatcac gaaagaatta aaaacaacct tgtcgaatca tgatttgatt    1920
ttttggctta tactttctaa ttttatatc ttgtgctgca aattagcacc aaaatatata    1980
tattcttctt cttcaacatc gaattcttta ttttgttaaa ggcatttttt tcttaacaga    2040
ggaattttac atcattctta gactgaactt tcgggataaa aaatctcgcc atgcaaaggt    2100
aatttatttt ttcatgacaa aagccacaat ggcgataatt ataactataa tactatgcaa    2160
aacgaaactt tacttgggtc ataccgagga aaacaaaggt acactcgatt gtgacaactc    2220
caccaaagac caccccacta ccaattcacc tttatttgtt tctttattca ctcaaaatct    2280 tttaatttt tttaattaat tcaattattc gcttctctcg ttgttttta accttttaat    2340 taaaaattga aaggaggtgc ctagggttc tctctctgca tggccactct cgctcttcac     2400
atcttttttt gggcaccatt gttaacgtat gcaaaaaaaa aaaaaaaaa aaaaaaact     2460 tacatgctaa gaaactctc tttccttgtc gtttctctca taaagaaat ttatttaaac     2520 ttatttagt ccaaaatta tcgttgctga tgaaaaatac aatataggaa gtgggatcgg     2580
atcggacaag gagtgaatta tctaccaact tagatttcac tcgtcttttg attgacaagt    2640
aacatacaca ataaacacat atgcataatt atttccatct tcaaccaaat gttgtagtga    2700
agtaatttga tctatgttat acggacatct atctactaaa tttttgaaaa aaaaaaaaa   2760 aactatctat tacatgctcc aaattattac ttgcttatgt aatttatgcg tatattagag    2820
atgttggtgt ttttctgaaa tttgatatat gttcttttat ctctgaaata tgatatgtga    2880
atcatcatag cattttcagt ggttacaacc ttatcgaatc gacaaagat tgaaacaaat    2940 tggaaaaaaa taaaatagtt ttactatttt ctaagcagcg tgaaatgaat atcagtataa    3000
tatatgaaac aaattcgtac gtgataaata tgtatacagt gatacaacca agaacgatga    3060
cgtatatgat tgacttgcaa aaataagcaa acaaatacc tgttcaaatc gacacttaat    3120
tccaaaaagg ttagtaataa gtaagaaggc ttttatttat gaaacaaaa agaaataaag    3180 agcctaagag aatgatgaaa attgaaagag aaaaagagc attgttatag aaaagaaaaa    3240
aaagagagag taaagagaat taagaaacac aataaattaa acaaaggaaa cttcatttct    3300
tctctttatc ccattcagct cctccccttct ctctctctct ctctctctct ctctctagat   3360
```

-continued

```
caattctttc ttctatgatg tgattatcca ccatatctgc gacctcttac ctaaaaagga      3420
tacaagtaag agattcaaag atggttttct catctcttcc agtgaatcag ttcgattccc      3480
aaaattggca gcaggtaaaa atcagtttat gatatttgct agatgtttct gattcgttcc      3540
tttttcctcc aagctcgatc aagatttatg aaaatttgat gagattttgt tcgacaaaat      3600
tcctagctat tgtggacgcg catatatatt acttatgaat attcttagtt gattaaaccc      3660 ttttttttc ttgtcttctc gaatatacga aaatatataa agatgatttc aattttggtc       3720
tttttttcta cttcaagact ttttaaaaaa ttattcttag ttgataaaaa cctttttttct     3780 tgtcttctcc aagggcttat gtataatgtt tttcttacag gattaatttt ctctttggtt     3840 agattttac accgccatgg aattatcact tcaaaaataa aaagtttaa agttactatg        3900 actttaatct gagttatta tccattttct ttttgcagct ttgttgaaaa actataatta       3960
atctgcaatt cttgtcaaag tagtcacaat ttttatctat tttcttttgt ctccgaccaa     4020
tgtttcaaac tcgaatcctt tcgttaaaag ttgtttctgc tttattataa acctgaaact     4080
aattagtaca aattatgtta atatgcagca agggaaccaa catcagctag aatgtgtcac     4140
aactgaccag aaccctaata attacttacg gcagctctca tcaccaccga cttctcaggt     4200
tgcaggttcg agtcaagcta gagtgaattc aatggtggaa cgtgctcgga tcgcaaaagt     4260
cccattgcct gaagcagctc taaattgccc tagatgtgac tcaaccaata ctaagttctg     4320
ttacttcaat aactatagcc ttactcaacc tcgccatttc tgcaaaacat gtcgtcgcta     4380
ttggacacgt ggcggttcct tgaggaatgt tcctgttgga ggaggcttta ggaggaacaa     4440
gagaagcaaa tccagatcga aatctacggt cgtggtctcg actgataata ctactagtac     4500
ttcatcactt acttctcgcc caagttactc aaaccctagc aagtttcata gctacggtca     4560
aatcccggag tttaattcca acttgcccat cttgcctcct ctccaaagcc ttggagatta     4620
caattcaagc aacactggat tagattttgg tggaactcaa ataagcaaca tgataagtgg     4680
tatgagttct agtggtggga tcttggatgc atggagaata cctccatcac aacaagctca     4740
gcaattccct ttcttgatca acactaccgg attggtgcaa tcttcaaacg cgttatatcc     4800
attactagaa ggtaagggag gtgttaatca aggtgattct caacagaaga gtagtgatta     4860
ttccaatcag ctaatgttta agcccttgat ggattttct tcaggcgggg ttagcgccac      4920
gcaaacaaga aatgtgaagg cggaagagaa tgatcaggat cggggtaggg atgggatgg      4980 agtgaataac ttatcaagaa acttttttggg taatatcaac ataaactcag gcaggaacga    5040
ggaatacaca tcatggggag gtaacagttc ttggaccggt ttcacctcca acaactcaac     5100
aggccatctc tcattctaag tactcagcac tagctattct tgatgattct tttgttggtt     5160
ggggtgtaca ttggtgcttg tcatgcgagt tattgctgag gaagatcaaa ccatgcagct     5220
atatccaaag gctaattttg aggctcaaag gaaaggtatg gttataaaac tatctttttg     5280
atcttttaaa agatcttcaa agtgtgagta tgtttattgg ttggcttctg gtgatattta     5340
tgttttatta gaatttggtc ttatatattg gctatatata gaggtgtggg tgatatgtat     5400
gaattcaaga gttgatgttg gaactttttt tgtgtgttca ttgaataatc atcgaattct     5460
caatttcttg gagacccatt atgagacatt gagacatcta tagaacatat atgtaatgta     5520
tattaaacgt acttaagtcg aatttatga ccaaagtaaa taaattatgc cgaatgtaca      5580
tgctaatatc gagtttaaac tatttttcc aatataacaa ctattttctc tttcgtccaa      5640
cttatatact cttattctga ttcttatttt cttctttta attccttttt cctttcccaa     5700
```

-continued

```
gacacaaaaa aaaaaaaata cagaaacgaa aaaaagagat tttaaaaatt cataacccac    5760
gagaattatg cacctaaatt cagactaatc ccccaaattt cagaaattta tgtattttg    5820 cgatttaata ttgtgttcac aatcataatg gccaactaac taattgaaaa gacaatggaa    5880
tgactgaaac catgcataat ctctcaagtc tcaacctatg aagaatcatg taaccaatag    5940
actatcatca tgattagtta atgcatgatc tataatgtat tctttgaaca tagatatgtc    6000
atttatctgg atataaagat ggcgttttaa cctactttgc aattttttgtt atatcttct    6060 tctaatacat atgatcaata cacttttgtt tttaaagaa attaaaaact tatttcaaac    6120
atcgatcaca tttttacttt tgtttccata ttgactacat ttataggctc acactttgt    6180 ttcggatcta gatatcacat caatccactt gctttgaaga cgtggttgga acgtcttctt    6240
tttccacgat gttcctcgtg ggtgggggtc atctttggg accactgtcg tagaggcat    6300 cttgaacgat agccttttcct ttatcgcaat gatggcattt gtagaagcca tcttcctttt    6360
ctactgtcct ttcgatgaag tgacagatag ctgggcaatg gaatccgagg aggtttcccg    6420
atattaccct tgttgaaaaa gtctcaatag ccctctggtc ttctgagact gtatctttga    6480
tattcttgga gtagacgaga gtgtcgtgct ccaccatgtt ggggatctag atatcacatc    6540
aatccacttg ctttgaagac gtggttggaa cgtcttcttt ttccacgatg ttcctcgtgg    6600 gtggggtcc atctttggga ccactgtcg tagaggcatc ttgaacgata gccttttcctt    6660 tatcgcaatg atggcatttg tagaagccat cttccttttc tactgtcctt tcgatgaagt    6720
gacagatagc tgggcaatgg aatccgagga ggtttcccga tattaccctt tgttgaaaag    6780
tctcaatagc cctctggtct tctgagactg tatctttgat attcttggag tagacgagag    6840
tgtcgtgctc caccatgttg gggatctaga tatcacatca atccacttgc tttgaagacg    6900
tggttggaac gtcttctttt tccacgatgt tcctcgtggg tggggtcca tctttgggac    6960 cactgtcggt agaggcatct tgaacgatag ccttttcctttt atcgcaatga tggcatttgt    7020
agaagccatc ttccttttct actgtccttt cgatgaagtg acagatagct gggcaatgga    7080
atccgaggag gtttcccgat attacccttt gttgaaaagt ctcaatagcc ctctggtctt    7140
ctgagactgt atctttgata ttcttggagt agacgagagt gtcgtgctcc accatgttgg    7200
ggatctagat atcacatcaa tccacttgct ttgaagacgt ggttggaacg tcttcttttt    7260
ccacgatgtt cctcgtgggt ggggtccat ctttgggacc actgtcggta gaggcatctt    7320
gaacgatagc cttttcctta tcgcaatgat ggcatttgta gaagccatct tccttttcta    7380 ctgtccttc gatgaagtga cagatagctg ggcaatggaa tccgaggagg tttcccgata    7440 ttacccttg ttgaaaagtc tcaatagccc tctggtcttc tgagactgta tctttgatat    7500
tcttggagta gacgagagtg tcgtgctcca ccatgttggg gatccactag ttctagagcg    7560
gccgccaccg cggtggagct                                               7580
```

```
<210> SEQ ID NO 2
<211> LENGTH: 307
<212> TYPE: PRT
<213> ORGANISM: Arabidopsis thaliana

<400> SEQUENCE: 2

Met Gln Gln Gly Asn Gln His Gln Leu Glu Cys Val Thr Thr Asp Gln
 1               5                  10                  15

Asn Pro Asn Asn Tyr Leu Arg Gln Leu Ser Ser Pro Thr Ser Gln
             20                  25                  30

Val Ala Gly Ser Ser Gln Ala Arg Val Asn Ser Met Val Glu Arg Ala
```

```
                 35                  40                  45
Arg Ile Ala Lys Val Pro Leu Pro Glu Ala Ala Leu Asn Cys Pro Arg
     50                  55                  60

Cys Asp Ser Thr Asn Thr Lys Phe Cys Tyr Phe Asn Asn Tyr Ser Leu
 65                  70                  75                  80

Thr Gln Pro Arg His Phe Cys Lys Thr Cys Arg Arg Tyr Trp Thr Arg
                 85                  90                  95

Gly Gly Ser Leu Arg Asn Val Pro Val Gly Gly Phe Arg Arg Asn
                100                 105                 110

Lys Arg Ser Lys Ser Arg Ser Lys Ser Thr Val Val Ser Thr Asp
                115                 120                 125

Asn Thr Thr Ser Thr Ser Ser Leu Thr Ser Arg Pro Ser Tyr Ser Asn
    130                 135                 140

Pro Ser Lys Phe His Ser Tyr Gly Gln Ile Pro Glu Phe Asn Ser Asn
145                 150                 155                 160

Leu Pro Ile Leu Pro Pro Leu Gln Ser Leu Gly Asp Tyr Asn Ser Ser
                165                 170                 175

Asn Thr Gly Leu Asp Phe Gly Gly Thr Gln Ile Ser Asn Met Ile Ser
                180                 185                 190

Gly Met Ser Ser Ser Gly Gly Ile Leu Asp Ala Trp Arg Ile Pro Pro
                195                 200                 205

Ser Gln Gln Ala Gln Gln Phe Pro Phe Leu Ile Asn Thr Thr Gly Leu
    210                 215                 220

Val Gln Ser Ser Asn Ala Leu Tyr Pro Leu Leu Glu Gly Gly Val Ser
225                 230                 235                 240

Ala Thr Gln Thr Arg Asn Val Lys Ala Glu Glu Asn Asp Gln Asp Arg
                245                 250                 255

Gly Arg Asp Gly Asp Gly Val Asn Asn Leu Ser Arg Asn Phe Leu Gly
                260                 265                 270

Asn Ile Asn Ile Asn Ser Gly Arg Asn Glu Glu Tyr Thr Ser Trp Gly
                275                 280                 285

Gly Asn Ser Ser Trp Thr Gly Phe Thr Ser Asn Asn Ser Thr Gly His
    290                 295                 300

Leu Ser Phe
305

<210> SEQ ID NO 3
<211> LENGTH: 19
<212> TYPE: DNA
<213> ORGANISM: Artificial Sequence
<220> FEATURE:
<223> OTHER INFORMATION: Synthetic Primer

<400> SEQUENCE: 3
gctctctcga ggtcgacgg                                          19

<210> SEQ ID NO 4
<211> LENGTH: 21
<212> TYPE: DNA
<213> ORGANISM: Artificial Sequence
<220> FEATURE:
<223> OTHER INFORMATION: Synthetic Primer

<400> SEQUENCE: 4
aattatgccg aatgtacatg c                                       21

<210> SEQ ID NO 5
```

-continued

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
taatacgact cactataggg                                              20

<210> SEQ ID NO 6
<211> LENGTH: 19
<212> TYPE: DNA
<213> ORGANISM: Artificial Sequence
<220> FEATURE:
<223> OTHER INFORMATION: Synthetic Primer

<400> SEQUENCE: 6
ccatgatgtg tatccctcg                                               19

<210> SEQ ID NO 7
<211> LENGTH: 19
<212> TYPE: DNA
<213> ORGANISM: Artificial Sequence
<220> FEATURE:
<223> OTHER INFORMATION: Synthetic Primer

<400> SEQUENCE: 7
gtggtatgag ttctagtgg                                               19

<210> SEQ ID NO 8
<211> LENGTH: 28
<212> TYPE: DNA
<213> ORGANISM: Artificial Sequence
<220> FEATURE:
<223> OTHER INFORMATION: Synthetic Primer

<400> SEQUENCE: 8
cgcggatccg tgaaggcgga agagaatg                                     28

<210> SEQ ID NO 9
<211> LENGTH: 29
<212> TYPE: DNA
<213> ORGANISM: Artificial Sequence
<220> FEATURE:
<223> OTHER INFORMATION: Synthetic Primer

<400> SEQUENCE: 9
ccatcgatca tacatatcac ccacacctc                                    29

<210> SEQ ID NO 10
<211> LENGTH: 29
<212> TYPE: DNA
<213> ORGANISM: Artificial Sequence
<220> FEATURE:
<223> OTHER INFORMATION: Synthetic Primer

<400> SEQUENCE: 10
cggggtacca tacatatcac ccacacctc                                    29

<210> SEQ ID NO 11
<211> LENGTH: 27
<212> TYPE: DNA
<213> ORGANISM: Artificial Sequence
<220> FEATURE:
<223> OTHER INFORMATION: Synthetic Primer

<400> SEQUENCE: 11
```

```
                                      -continued gacctcgagt gaaggcggaa gagaatg                                        27

<210> SEQ ID NO 12
<211> LENGTH: 888
<212> TYPE: DNA
<213> ORGANISM: Arabidopsis thaliana

<400> SEQUENCE: 12
atggtggaac gtgctcggat cgcaaaagtc ccattgcctg aagcagctct aaattgccct     60
agatgtgact caaccaatac taagttctgt tacttcaata actatagcct tactcaacct   120
cgccatttct gcaaaacatg tcgtcgctat tggacacgtg gcggttcctt gaggaatgtt   180
cctgttggag gaggctttag gaggaacaag agaagcaaat ccagatcgaa atctacggtc   240
gtggtctcga ctgataatac tactagtact tcatcactta cttctcgccc aagttactca   300
aaccctagca gtttcatag ctacggtcaa atcccggagt ttaattccaa cttgcccatc   360
ttgcctcctc tccaaagcct tggagattac aattcaagca cactggatt agattttggt   420 ggaactcaaa taagcaacat gataagtggt atgagttcta gtggtgggat cttggatgca   480
tggagaatac ctccatcaca acaagctcag caattcccctt tcttgatcaa cactaccgga   540
ttggtgcaat cttcaaacgc gttatatcca ttactagaag gtaagggagg tgttaatcaa   600
ggtgattctc aacagaagag tagtgattat tccaatcagc taatgtttaa gcccttgatg   660
gatttttctt caggcggggt tagcgccacg caaacaagaa atgtgaaggc ggaagagaat   720
gatcaggatc ggggtaggga tggggatgga gtgaataact tatcaagaaa cttttttggt   780
aatatcaaca taaactcagg caggaacgag gaatacacat catggggagg taacagttct   840
tggaccggtt tcacctccaa caactcaaca ggccatctct cattctaa                888

<210> SEQ ID NO 13
<211> LENGTH: 177
<212> TYPE: DNA
<213> ORGANISM: Arabidopsis thaliana

<400> SEQUENCE: 13
atgcagcaag ggaaccaaca tcagctagaa tgtgtcacaa ctgaccagaa ccctaataat     60
tacttacggc agctctcatc accaccgact tctcaggttg caggttcgag tcaagctaga   120
gtgaattcaa tggtggaacg tgctcggatc gcaaaagtcc cattgcctga agcagct       177

<210> SEQ ID NO 14
<211> LENGTH: 48
<212> TYPE: DNA
<213> ORGANISM: Arabidopsis thaliana

<400> SEQUENCE: 14
atggtggaac gtgctcggat cgcaaaagtc ccattgcctg aagcagct                  48

<210> SEQ ID NO 15
<211> LENGTH: 684
<212> TYPE: DNA
<213> ORGANISM: Arabidopsis thaliana

<400> SEQUENCE: 15
aacaagagaa gcaaatccag atcgaaatct acggtcgtgg tctcgactga taatactact    60
agtacttcat cacttacttc tcgcccaagt tactcaaacc ctagcaagtt tcatagctac   120
ggtcaaatcc cggagtttaa ttccaacttg cccatcttgc ctcctctcca aagccttgga   180
```

```
gattacaatt caagcaacac tggattagat tttggtggaa ctcaaataag caacatgata    240
agtggtatga gttctagtgg tgggatcttg gatgcatgga gaatacctcc atcacaacaa    300
gctcagcaat tcccttcttt gatcaacact accggattgg tgcaatcttc aaacgcgtta    360
tatccattac tagaaggtaa gggaggtgtt aatcaaggtg attctcaaca gaagagtagt    420
gattattcca atcagctaat gtttaagccc ttgatggatt tttcttcagg cggggttagc    480
gccacgcaaa caagaaatgt gaaggcggaa gagaatgatc aggatcgggg tagggatggg    540
gatggagtga ataacttatc aagaaacttt tgggtaata tcaacataaa ctcaggcagg     600
aacgaggaat acacatcatg gggaggtaac agttcttgga ccggtttcac ctccaacaac    660
tcaacaggcc atctctcatt ctaa                                           684

<210> SEQ ID NO 16
<211> LENGTH: 156
<212> TYPE: DNA
<213> ORGANISM: Arabidopsis thaliana

<400> SEQUENCE: 16
ctaaattgcc ctagatgtga ctcaaccaat actaagttct gttacttcaa taactatagc     60
cttactcaac ctcgccattt ctgcaaaaca tgtcgtcgct attggacacg tggcggttcc    120
ttgaggaatg ttcctgttgg aggaggcttt aggagg                              156

<210> SEQ ID NO 17
<211> LENGTH: 1235
<212> TYPE: DNA
<213> ORGANISM: Arabidopsis thaliana

<400> SEQUENCE: 17
caaccaagaa cgatgacgta tatgattgac ttgcaaaaat aagcaaacaa aatacctgtt     60
caaatcgaca cttaattcca aaaggttag taataagtaa gaaggctttt atttatgaaa    120
acaaaaagaa ataaagagcc taagagaatg atgaaaattg aaagagaaaa aagagcattg    180
ttatagaaaa gaaaaaaaag agagagtaaa gagaattaag aaacacaata aattaaacaa    240
aggaaacttc atttcttctc tttatcccat tcagctcctc ccttctctct ctctctctct    300
ctctctctct ctagatcaat tctttcttct atgatgtgat tatccaccat atctgcgacc    360
tcttacctaa aaaggataca agtaagagat tcaaagatgg ttttctcatc tcttccagtg    420
aatcagttcg attcccaaaa ttggcagcag gtaaaaatca gtttatgata tttgctagat    480
gtttctgatt cgttcctttt tcctccaagc tcgatcaaga tttatgaaaa tttgatgaga    540
ttttgttcga caaattcct agctattgtg gacgcgcata tatattactt atgaatattc     600
ttagttgatt aaacccttt ttttcttgt cttctcgaat atacgaaaat atataaagat      660
gatttcaatt ttggtctttt tttctacttc aagactttt aaaaaattat tcttagttga    720
taaaaacctt ttttcttgtc ttctccaagg gcttatgtat aatgttttc ttacaggatt    780 aattttctct ttggttagat ttttacaccg ccatggaatt atcacttcaa aaataaaaaa    840
gtttaaagtt actatgactt taatctgagt tatttatcca ttttcttttt gcagctttgt    900
tgaaaaacta taattaatct gcaattcttg tcaaagtagt cacaattttt atctattttc    960
ttttgtctcc gaccaatgtt tcaaactcga atcctttcgt taaagttgt ttctgcttta   1020 ttataaacct gaaactaatt agtacaaatt atgttaatat gcagcaaggg aaccaacatc   1080
agctagaatg tgtcacaact gaccagaacc ctaataatta cttacggcag ctctcatcac   1140
caccgacttc tcaggttgca ggttcgagtc aagctagagt gaattcaatg gtggaacgtg   1200
```

-continued

| | |
|---|---|
| ctcggatcgc aaaagtccca ttgcctgaag cagct | 1235 |

<210> SEQ ID NO 18
<211> LENGTH: 1746
<212> TYPE: DNA
<213> ORGANISM: Arabidopsis thaliana

<400> SEQUENCE: 18

| | |
|---|---|
| aacaagagaa gcaaatccag atcgaaatct acggtcgtgg tctcgactga taatactact | 60 |
| agtacttcat cacttacttc tcgcccaagt tactcaaacc ctagcaagtt tcatagctac | 120 |
| ggtcaaatcc cggagtttaa ttccaacttg cccatcttgc ctcctctcca aagccttgga | 180 |
| gattacaatt caagcaacac tggattagat tttggtggaa ctcaaataag caacatgata | 240 |
| agtggtatga gttctagtgg tgggatcttg gatgcatgga gaatacctcc atcacaacaa | 300 |
| gctcagcaat tcccttttctt gatcaacact accggattgg tgcaatcttc aaacgcgtta | 360 |
| tatccattac tagaaggtaa gggaggtgtt aatcaaggtg attctcaaca gaagagtagt | 420 |
| gattattcca atcagctaat gtttaagccc ttgatggatt tttcttcagg cggggttagc | 480 |
| gccacgcaaa caagaaatgt gaaggcggaa gagaatgatc aggatcgggg tagggatggg | 540 |
| gatggagtga ataacttatc aagaaacttt tgggtaata tcaacataaa ctcaggcagg | 600 |
| aacgaggaat acacatcatg gggaggtaac agttcttgga ccggtttcac ctccaacaac | 660 |
| tcaacaggcc atctctcatt ctaataagta ctcagcacta gctattcttg atgattcttt | 720 |
| tgttggttgg ggtgtacatt ggtgcttgtc atgcgagtta ttgctgagga agatcaaacc | 780 |
| atgcagctat atccaaaggc taattttgag gctcaaagga aaggtatggt tataaaacta | 840 |
| tcttttttgat cttttaaaag atcttcaaag tgtgagtatg tttattggtt ggcttctggt | 900 |
| gatatttatg ttttattaga atttggtctt atatattggc tatatataga ggtgtgggtg | 960 |
| atatgtatga attcaagagt tgatgttgga aacttttttg tgtgttcatt gaataatcat | 1020 |
| cgaattctca atttcttgga gacccattat gagacattga gacatctata gaacatatat | 1080 |
| gtaatgtata ttaaacgtac ttaagtcgaa ttttatgacc aaagtaaata aattatgccg | 1140 |
| aatgtacatg ctaatatcga gtttaaacta tttttttccaa tataacaact atttttctctt | 1200 |
| tcgtccaact tatatactct tattctgatt cttatttttct tctttttaat tccttttttcc | 1260 |
| tttcccaaga cacaaaaaaa aaaaaataca gaaacgaaaa aaagagattt taaaaattca | 1320 |
| taacccacga gaattatgca cctaaaattca gactaatccc ccaaatttca gaaatttatg | 1380 |
| tatttttgcg atttaatatt gtgttcacaa tcataatggc caactaacta attgaaaaga | 1440 |
| caatggaatg actgaaacca tgcataatct ctcaagtctc aacctatgaa gaatcatgta | 1500 |
| accaatagac tatcatcatg attagttaat gcatgatcta taatgtattc tttgaacata | 1560 |
| gatatgtcat ttatctggat ataaagatgg cgtttttaacc tactttgcaa tttttgttat | 1620 |
| atctttcttc taatacatat gatcaataca cttttgtttt taaaagaaat taaaaactta | 1680 |
| tttcaaacat cgatcacatt tttacttttg tttccatatt gactacattt ataggctcac | 1740 |
| acttttt | 1746 |

<210> SEQ ID NO 19
<211> LENGTH: 1058
<212> TYPE: DNA
<213> ORGANISM: Arabidopsis thaliana

<400> SEQUENCE: 19

| | |
|---|---|
| caaccaagaa cgatgacgta tatgattgac ttgcaaaaat aagcaaacaa aatacctgtt | 60 |

```
caaatcgaca cttaattcca aaaaggttag taataagtaa gaaggctttt atttatgaaa      120
acaaaaagaa ataaagagcc taagagaatg atgaaaattg aaagagaaaa aagagcattg      180
ttatagaaaa gaaaaaaaag agagagtaaa gagaattaag aaacacaata aattaaacaa      240
aggaaacttc atttcttctc tttatcccat tcagctcctc ccttctctct ctctctctct      300
ctctctctct ctagatcaat tctttcttct atgatgtgat tatccaccat atctgcgacc      360
tcttacctaa aaggatacaa gtaagagatt caaagatgg ttttctcatc tcttccagtg      420
aatcagttcg attcccaaaa ttggcagcag gtaaaaatca gtttatgata tttgctagat      480
gtttctgatt cgttcctttt tcctccaagc tcgatcaaga tttatgaaaa tttgatgaga      540
ttttgttcga caaaattcct agctattgtg gacgcgcata tatattactt atgaatattc      600
ttagttgatt aaacccttttt tttttcttgt cttctcgaat atacgaaaat atataaagat      660
gatttcaatt ttggtctttt tttctacttc aagactttt aaaaaattat tcttagttga      720 taaaacctt ttttcttgtc ttctccaagg gcttatgtat aatgtttttc ttacaggatt      780
aattttctct ttggttagat ttttacaccg ccatggaatt atcacttcaa aaataaaaaa      840
gtttaaagtt actatgactt taatctgagt tatttatcca ttttcttttt gcagctttgt      900
tgaaaaacta taattaatct gcaattcttg tcaaagtagt cacaattttt atctattttc      960
ttttgtctcc gaccaatgtt tcaaactcga atcctttcgt taaaagttgt ttctgcttta     1020
ttataaacct gaaactaatt agtacaaatt atgttaat                             1058

<210> SEQ ID NO 20
<211> LENGTH: 1062
<212> TYPE: DNA
<213> ORGANISM: Arabidopsis thaliana

<400> SEQUENCE: 20
taagtactca gcactagcta ttcttgatga ttcttttgtt ggttggggtg tacattggtg       60
cttgtcatgc gagttattgc tgaggaagat caaaccatgc agctatatcc aaaggctaat      120
tttgaggctc aaaggaaagg tatggttata aaactatctt tttgatcttt taaaagatct      180
tcaaagtgtg agtatgttta ttggttggct tctggtgata tttatgtttt attagaattt      240
ggtcttatat attggctata tatagaggtg tgggtgatat gtatgaattc aagagttgat      300
gttggaaact tttttgtgtg ttcattgaat aatcatcgaa ttctcaattt cttggagacc      360
cattatgaga cattgagaca tctatagaac atatatgtaa tgtatattaa acgtacttaa      420
gtcgaatttt atgaccaaag taaataaatt atgccgaatg tacatgctaa tatcgagttt      480
aaactatttt ttccaatata caactatttt tctctttcgt ccaacttata tactcttatt      540
ctgattctta ttttcttctt tttaattcct ttttcctttc ccaagacaca aaaaaaaaa      600 aatacagaaa cgaaaaaaag agattttaaa aattcataac ccacgagaat tatgcaccta      660
aattcagact aatcccccaa atttcagaaa tttatgtatt tttgcgattt aatattgtgt      720
tcacaatcat aatggccaac taactaattg aaaagacaat ggaatgactg aaaccatgca      780
taatctctca agtctcaacc tatgaagaat catgtaacca atagactatc atcatgatta      840
gttaatgcat gatctataat gtattctttg aacatagata tgtcatttat ctggatataa      900
agatggcgtt ttaacctact ttgcaatttt tgttatatct ttcttctaat acatatgatc      960
aatacacttt tgttttttaaa agaaattaaa aacttatttc aaacatcgat cacattttta     1020
cttttgtttc catattgact acatttatag gctcacactt tt                        1062
```

GENE FOR A DOF TRANSCRIPTION FACTOR CAPABLE OF ALTERING THE SIZE AND STATURE OF A PLANT

This application claims the benefit of priority of the Provisional patent application Ser. No. 60/406,657 filed Aug. 28, 2002, herein incorporated by reference.

FIELD OF INVENTION

The present invention relates generally to plant genetic engineering, and specifically to a method for producing genetically engineered plants characterized as having altered size and stature.

BACKGROUND OF INVENTION

For each plant species, there exists a wide discrepancy in plant growth due to environmental conditions. Under most conditions, the maximum growth potential of a plant is not realized. Plant breeding has demonstrated that a plant's resources can be redirected to individual organs to enhance growth.

Genetic engineering of plants, which entails the isolation and manipulation of genetic material, e.g., DNA or RNA, and the subsequent introduction of that material into a plant or plant cells, has changed plant breeding and agriculture considerably over recent years. Increased crop food values, higher yields, feed value, reduced production costs, pest resistance, stress tolerance, drought resistance, the production of pharmaceuticals, chemicals and biological molecules as well as other beneficial traits are all potentially achievable through genetic engineering techniques.

Plant growth responds to the increased availability of mineral nutrients in the soil, but shoot and root growth respond differently. Moreover, a direct relationship between mineral nutrient availability and change of growth rate is rarely observed over a larger concentration range. This suggest that plant growth is limited materially by nutrients required for cell growth as well as by signaling pathways that control the rate of organ growth for the overall benefit of the plant. Although the components of these regulatory pathways have not been identified, they define two distinct avenues to potentially improve plant growth.

Plants rarely grow under optimal conditions. Plant growth can be limited by water availability, mineral nutrients and a short growing season. Drought tolerance in genetic variants of a given species is well correlated with the penetration depth of its root system into the soil. Fertilizers are often not optimally utilized because of insufficiently penetrating root systems. Although the induction of flowering can now be controlled, thereby extending the potential growth range of some important crop species, this does not in itself lead to increased biomass.

The ability to manipulate gene expression provides a means of producing new characteristics in transformed plants. For example, the ability to increase the size of a plant's root system would permit increased nutrient assimilation from the soil. Moreover, the ability to increase leaf growth would increase the capacity of a plant to assimilate solar energy. Obviously, the ability to control the growth of an entire plant, or specific target organs thereof would be very desirable.

SOB1/OBP3 is a member of the Dof family of transcription factors that, to date, remain unique to plants. Computer programs that predict gene function have identified more than 50 Dof transcription factors in the *Arabidopsis* genome (Riechmann, J. L. and Ratcliffe, O. J. (2000) Curr Opin Plant Bio 3:423-434). This family of transcriptional regulators shares a conserved DNA-binding domain made up of 52 amino acid residues in which a $CX_2CX_{21}CX_2C$ motif is predicted to form a single zinc finger, hence their name domain of one finger. These transcription factors are thought to have a common core recognition sequence of AAAG (Yanagisawa, S. and Schmidt, R. J. (1999) Plant J 17:209-214).

Transcriptional activation, DNA binding and mRNA accumulation studies have been previously reported for OBP3 and two other OBPs from *Arabidopsis* (Kang, H.-G. and Singh, K. B. (2000) Plant J 21:329-339). Though these studies show salicylic acid and auxin induction of all three OBP mRNAs, they have not revealed a role for these transcription factors during development. The experimental findings of Kang and Singh (2000) demonstrated that constitutive expression of the OBP3 gene in *Arabidopsis* results in severely dwarfed plants with stunted root growth. Applicants speculate that the differences in phenotypes between 35S:OBP3 (the nucleic acid construct utilized by Kang and Singh), and sob1-D phyB-4 (the nucleic acid construct of this invention) may be caused by the differences between constitutive expression seen with the CaMV 35S promoter and the amplified transcriptional expression patterns often seen in activation-tagging mutants (Neff, M. M. et al. (1999) Proc Natl Acad Sci USA 96:15316-15323; Weigel, D. et al. (2000) Plant Physiol 122:1003-1013).

There is a need for a mechanism to genetically alter plants to efficiently and effectively control their size and stature with completely normal and healthy root growth. The present invention provides genetically stable plants that are either larger or smaller based on the over- or under-expression of the SOB1/OBP3 gene. Applicants further provide plant cells transformed by OBP3 to control photomorphogenesis.

SUMMARY OF THE INVENTION

The present invention is based on the discovery that a change in the size and stature of a plant can be achieved by altering the level of OBP3 expression.

One aspect of the invention is a transgenic plant cell transformed by an OBP (OBF (ocs binding factor) binding protein) coding nucleic acid expression vector, wherein expression of the nucleic acid sequence in the plant cell results in an alteration in the size of the resulting plant as compared to a corresponding wild-type variety of the plant cell. In one embodiment, the OBP coding nucleic acid sequence is the OBP3 from *Arabidopsis thaliana*.

Another aspect of the invention is a transgenic plant cell transformed by an OBP (OBF (ocs binding factor) binding protein) antisense coding nucleic acid expression vector, wherein expression of the nucleic acid sequence in the plant cell results in an increase in the size of the resulting plant as compared to a corresponding wild-type variety of the plant cell. In one embodiment, the OBP antisense coding nucleic acid sequence is the OBP3 from *Arabidopsis thaliana*.

Another aspect of the invention is an agricultural product produced by any of the below-described transgenic plants, plant parts or seeds.

Another aspect of the invention is an isolated OBP3 as described below. In one embodiment, the OBP3 is SEQ ID NO:2. Another aspect of the invention is an isolated OBP3 coding nucleic acid, wherein the OBP3 coding nucleic acid codes for OBP3 as described below. In one embodiment, the OBP3 coding nucleic acid is SEQ ID NO:1.

Another aspect of the invention is an isolated recombinant antisense expression vector comprising:

(a) a promoter, said promoter being functional in a plant cell; and (b) an *Arabidopsis thaliana* OBP3 antisense coding nucleic acid, said promoter being operably linked to said OBP3 antisense coding nucleic acid and said antisense coding nucleic acid oriented with respect to said promoter such that the RNA produced is complementary in nucleotide sequence and capable of hybridizing in a stringent manner to mRNA encoding *Arabidopsis thaliana* OBP3, wherein said OBP3 antisense coding nucleic acid comprises a nucleotide sequence of at least 15 contiguous nucleotides of SEQ ID NO:1 compared to a corresponding wild-type variety of the host cell.

Another aspect of the invention is a method for producing a transgenic plant having altered size as compared to the corresponding wild-type plant, said method comprising:

(a) transforming plant cells by introducing a nucleic acid vector encoding *Arabidopsis thaliana* OBP3;

(b) producing plants from said transformed plant cells.

In preferred embodiments, the OBP3 and OBP3 coding nucleic acid are as described below.

Another aspect of the invention is a method for altering the size of a plant, said method comprising:

(a) introducing a nucleic acid vector encoding *Arabidopsis thaliana* OBP3 into a plant cell;

(b) regenerating the plant cell into a transgenic plant;

(c) evaluating the change in size by comparing the plant obtained by introducing the nucleic acid molecule with the size of a corresponding wild-type plant.

The methods described can be performed such that the size of the plant is either increased or decreased. For example, plant size is decreased via increasing the expression of OBP3 and plant size is increased via decreasing expression of OBP3.

DESCRIPTION OF THE FIGURES

FIG. 1 discloses plants resulting from the study carried out in Example 2. Seedlings were grown for 10 days in white light (50 µEm$^2$s$^1$). Analysis of T2 and T3 generations indicate that the sob1-D mutation is dominant for suppression of the phyB-4 long-hypocotyl phenotype and semidominant for the leaf/petiole phenotype conferred by the homozygous suppressor shown here. F2 analysis from crosses with the wild type indicate that seedling and adult phenotypes are similar for both sob1-D phyB and sob1-D PHYB genotypes.

FIG. 2 discloses a plasmid according to Example 3. The pSOB1-H plasmid was cloned from sob1-D phyB-4 genomic DNA digested with the restriction endonuclease HindIII before ligation and transformation into *E. coli*. Primer P1 was used for sequence analysis and identification of genomic DNA adjacent to the enhancer elements. Primers P2 and P3 were used for PCR analysis to demonstrate that the DNA adjacent to the enhancers in the pSOB1-H plasmid was the same as the genomic DNA in the sob1-D phyB-4 mutant. Primers P4 and P5, which flank a predicted intron (*), were used for RT-PCR analysis of OPB3 transcript accumulation in the sob 1-D phyB-4 mutant. OBP3 has two potential transcriptional start sites (**). A SacI fragment containing the enhancer elements and the SOB1/OPB3 ORF was transformed into a phyB-4 mutant for recapitulation of the sob1-D phenotype.

FIG. 3 discloses results from the study carried out in Example 4. RT-PCR was performed essentially as described in (Neff, M. M. et al. (1999) Proc Natl Acad Sci USA 96:15316-15323). An agarose gel of EtBR-stained PCR products (⅙$^{th}$ of the total reaction) is shown. Both primer pairs span a predicted intron allowing the identification of both cDNA and genomic DNA derived PCR products. The faster migrating (lower) band in each case is a product the cDNA template. Other nearby open reading frames did not have altered expression the sob1-D phyB-4 mutant.

FIG. 4 discloses the seedlings resulting from the study carried out in Example 5. Seven-day-old seedlings were photographed after being grown in white light. Wild type (A), phyB-4 (B) and sob1-D phyB-4 (C) seedlings were compared with two independent phyB-4 primary transformants harboring the sob1-D recapitulation T-DNA (D and E).

FIG. 5 discloses the plants resulting from the studies carried out in Examples 5 & 6. Homozygous phyB-4 mutants that are SOB1/SOB1 (A), sob1-D/SOB1 (B) or sob1-D/sob1-D (C) were grown under greenhouse conditions for approximately two weeks. Heterozygous sob1-D/+ lines (B) suppress the long-petiole, shade-avoidance phenotype of phyB-4mutants (A). Homozygous sob1-D/sob1-D lines (C) are the most severe dwarfs. The zygosity of the sob1-D mutation was confirmed in the progeny from each self-pollinated plant.

FIG. 6 discloses the plants resulting from the study carried out in Example 5. Adult sob1-D phyB-4 mutants (B) are severely dwarfed when compared to phyB-4 (A). Some primary transformants, heterozygous for the sob1-D recapitulation T-DNA (C), also exhibit the same adult phenotype as sob1-D phyB-4 homozygotes (B).

FIG. 7 discloses the results resulting from the study carried out in Example 6. Six day old wild-type (open bars), phyB-4 (single-hatched bars) and sob1-D phyB-4 seedlings (double-hatched bars) were grown in 50 mEm$^2$s$^1$ of continuous white light (A) or darkness (B) before having their hypocotyls measured or photographed (C). The sob1-D mutation suppresses the long-hypocotyl phenotype of phyB-4 in white light (A) and confers a long hypocotyl phenotype in the dark (B) with etiolated sob1-D phyB-4 mutant seedlings (C, right) resembling the wild type (C, left) and phyB-4 (C, middle). Error bars=±1 SE from the mean of 3 independent experiments (n ~30).

FIG. 8 discloses graphically discloses results from the study carried out in Example 6. Seedlings were grown in 50 mEm$^2$s$^1$ of continuous white light on vertical plates. Their images were digitized with a flat-bed scanner at the same time each day. Root length was measured using NIH Image software. Error bars=±1 SE from the mean from 2 independent experiments (n~20).

FIG. 9 graphically discloses results from the study carried out in Example 6. Six day old sob1-D phyB-4 hypocotyls (double-dashed line) were compared to those from the wild-type (solid line) and phyB-4 (single-dashed line) when grown in the dark and at varying intensities of white light. Error bars=±1 SE from the mean (n~30).

FIG. 10 discloses seedlings resulting from the study carried out in Example 6. Seedlings were grown for six days in continuous far-red light before being photographed. The sob1-D mutation was genotyped by it's linkage to the kanamycin resistance gene and confirmed by PCR. The phyA mutation was genotyped with a PCR-based dCAPS maker (Neff, M. M. et al. (1999) Proc Natl Acad Sci USA 96:15316-15323).

FIG. 11 discloses seedlings resulting from the study carried out in Example 6. Seedlings were grown for six days in continuous blue light before being photographed. The sob1-D mutation was genotyped by it's linkage to the kanamycin resistance gene and confirmed by PCR. The cry1 mutation was genotyped with a PCR-based dCAPS marker (Neff, M. M. et al. (1999) Proc Natl Acad Sci USA 96:15316-15323).

FIG. 12 discloses the results from the study carried out in Example 6. RT-PCR analysis demonstrates that multiple OBP3 RNAi transgenic lines have reduced expression of OBP3 when compared to the wild-type. UBQ10 primers were used as a template control.

FIG. 13 discloses plants resulting from the study carried out in Example 6. OBP3 RNAi lines #1 and #2 (heterozygous for the transgene) appear to be significantly larger than the wild-type (Col-0).

FIG. 14 discloses plants resulting from the study carried out in Example 7. Two-month-old wildtype tobacco plants (A) are compared to four independent transformation events containing the sob1-D/OBP3-overexpressing transgene (B through E). Unlike the wild type (A), transformation events #3 (B), #6 (C) and #34 (D) are half the size of the wild type. Transformation event #7 (E) is a strong dwarf with small leaves. Unlike the wild type, all four independent transformation events have multiple shoots due to decreased apical dominance. All plants are the same age and have been grown under similar conditions.

FIG. 15 discloses the plants resulting from the study carried out in Example 7. This close-up shot of two-month-old tobacco compares the wild type (A) with two independent transformation events containing the sob1-D/OBP3-overexpressing transgene (B, and C). Unlike the wild type (A), transformation event #34 (C) has multiple shoots due to decreased apical dominance. Transformation event #7 (B) is a strong dwarf with small leaves and multiple shoots. All plants are the same age and have been grown under similar conditions.

ABBREVIATION AND DEFINITIONS

Figure 1:
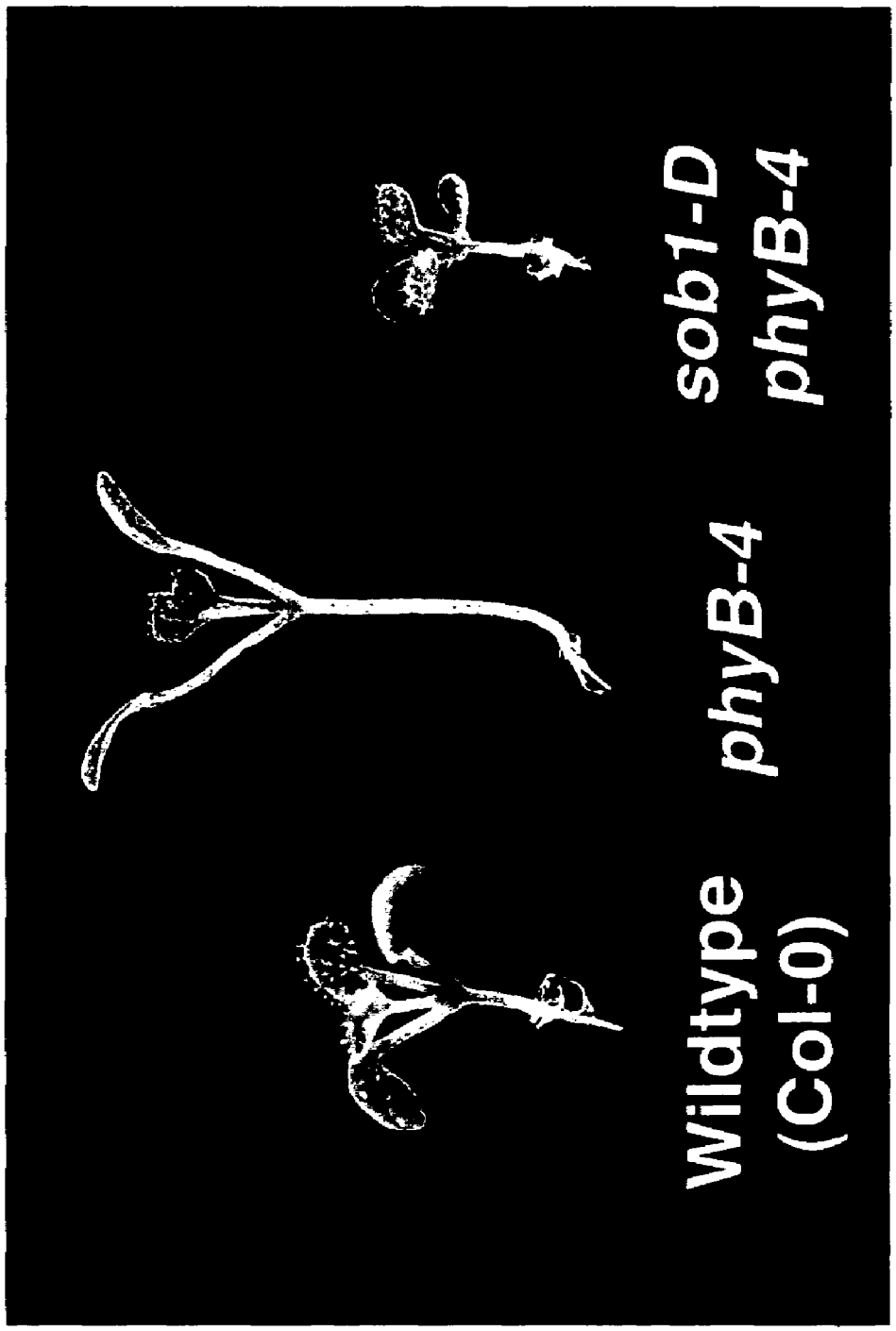
FIG. 1: The sob1-D mutation suppresses the phyB-4 long hypocotyl phenotype.

To facilitate understanding of the invention, a number of terms are defined below. Definitions of certain terms are included here. Any term not defined is understood to have the normal meaning used by scientists contemporaneous with the submission of this application.

As used herein, the term "plant" refers to either a whole plant, a plant part including seed, cuttings, tubers, fruit, flowers, etc., a plant cell, or a group of plant cells, such as plant tissue or plant seed and progeny thereof. Plantlets are also included within the meaning of "plant". Plants included in the invention are any plants amenable to transformation techniques, including gymnosperms and angiosperms, both monocotyledons and dicotyledons and trees.

Examples of monocotyledonous angiosperms include, but are not limited to, asparagus, field and sweet corn, barley, wheat, rice, sorghum, onion, pearl millet, rye and oats and other cereal grains. Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Examples of woody species include poplar, pine, sequoia, cedar, oak, etc. Tree species include but are not limited to: fir, pine, spruce, larch, cedar, hemlock, acacia, alder, aspen, beech, birch, oak, gum trees, poplar and the like.

As used herein, the term "variety" refers to a group of plants within a species that share constant characteristics that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

Alterations in "characteristics of a plant" refer to any changes in at least one of morphology of a plant and color of a plant, more specifically, any changes in at least one of morphology of a flower, color of a flower, a size of a plant, and the number of branches. These changes are evaluated by comparing the characteristics of a plant obtained by introducing a gene of the present invention with the characteristics of a plant (wild-type, horticultural type or wild accession variety) before introducing the gene. "Wild-type" refers to any plant or plants (mutant, horticultural variety or wild accession variety) that can be used for transformation by the methods of the present invention, but have not been transformed with the genes of or by the methods of this invention. These "wild-type" plants are used as a control for comparison to the corresponding (i.e. plants from the same variety grown under the same conditions) plants that have been transformed by the methods of this invention. Comparison of the wild-type plants and the transformed plants of this invention can be made by comparing the resulting characteristics of a statistically significant population of a parental non-transformed line ("wild-type") and the characteristics of a statistically significant population of the transgenic siblings with statistical analysis by t-test. A successful transformation of the plants of this invention can be demonstrated by unpaired t-test preferably wherein P=0.15, more preferably wherein P=0.10, most preferably wherein P=0.05.

Alterations in morphology of a flower and/or color of a flower are examples of preferable alterations of plant morphology. (Hereinafter, the term "flower" refers to petals unless otherwise specified.)

Examples of altered morphology of a flower include, but are not limited to, morphology which may be caused by an alteration in a shape of an individual petal (large petals, small petals, sawtooth-shaped petals, round petals, wave-shaped petals, etc.), morphology which may be caused by an alteration in the number of petals (double flower, single flower, etc.), and morphology which may be caused by abnormal development of petals (star-shaped petals, etc.).

Examples of color change of a flower include, but are not limited to, single colors such as white, scarlet red, salmon pink, rose, pink, blue violet, violet, pale violet, sky blue, violet red, and yellowish white, and multi-color patterns of two or more colors (e.g., variegation, spots, marginal variegation, coloring of an outer edge of a petal).

Examples of a changed size of a plant include, but are not limited to, a dwarf and a semi-dwarf. The dwarfism is preferably about ½ or less, more preferably about ⅓ or less of a standard size of the plant before the introduction of the gene. An example of altered branch number includes but is not limited to increased branching.

Changed characteristics of a plant include preferably morphology caused by an abnormal development of petals, a double color pattern, a dwarf, or increased branching; and more preferably a combination thereof (e.g., a combination of abnormal development of petals and a double color pattern and/or a combination of a dwarf and increased branching). More preferably, changed characteristics of a plant include morphology of a star shape, coloring of an outer edge of a petal, a dwarf, or increased branching; and more preferably a combination thereof (e.g., a combination of morphology of a star shape and coloring of an outer edge of a petal and/or a combination of a dwarf and increased branching).

As also used herein, the terms "nucleic acid" and "nucleic acid molecule" are intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene.

The term "transcription factor" as used herein refers to a protein which binds to a DNA regulatory region of genes to control the synthesis of mRNA. Some transcription factors are known to have a highly conservative amino acid sequence called a zinc finger motif in their DNA binding domains.

As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in Current Protocols in Molecular Biology, 6.3.1-6.3.6, John Wiley & Sons, N.Y. (1989). A preferred, non-limiting example of stringent hybridization conditions are hybridization in 6×SSC at about 45° C., followed by one or more washes in 0.2×SSC, 0.1% SDS at 50-65° C. Examples of moderate to high stringency conditions include, for example, include initial hybridization in 6×SSC, 5× Denhardt's solution, 100 g/ml fish sperm DNA, 0.1% SDS, at 55 C. for sufficient time to permit hybridization (e.g., several hours to overnight), followed by washing two times for 15 min each in 2×SSC, 0.1% SDS, at room temperature, and two times for 15 min each in 0.5-1×SSC, 0.1% SDS, at 55 C., followed by autoradiography. Typically, the nucleic acid molecule is capable of hybridizing when the hybridization mixture is washed at least one time in 0.1×SSC at 50° C., preferably at 55° C., more preferably at 60° C., and still more preferably at 65° C. Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

As used herein, a "naturally occurring" nucleic acid molecule refers to an RNA or DNA molecule having a nucleotide sequence that occurs in nature (e.g., encodes a natural protein).

As used herein, the term "allelic variant" refers to a nucleotide sequence containing polymorphisms that lead to changes in the amino acid sequences of OBP3 and that exist within a natural population (e.g., a plant species or variety). Such natural allelic variations can typically result in 1-5% variance in an OBP3 nucleic acid.

As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode proteins having the same or similar functions. As also used herein, the term "paralogs" refers to two nucleic acids that are related by duplication within a genome. Paralogs usually have different functions, but these functions may be related (Tatusov, R. L. et al. (1997) Science 278:631-637).

As used herein, the term "biologically active portion of" OBP3 is intended to include a portion, e.g., a domain/motif, of OBP3 that participates in the developmental pathway affecting the size of a plant or participates in the transcription of a protein involved in the developmental pathway affecting the size of a plant.

As used herein, an OBP3 "chimeric protein" or "fusion protein" comprises an OBP3 polypeptide operatively linked to a non-OBP3 polypeptide. An OBP3 polypeptide refers to a polypeptide having an amino acid sequence corresponding to OBP3, whereas a non-OBP3 polypeptide refers to a polypeptide having an amino acid sequence corresponding to a protein which is not substantially homologous to the OBP3, e.g., a protein that is different from the OBP3 and is derived from the same or a different organism. Within the fusion protein, the term "operatively linked" indicates that the OBP3 polypeptide and the non-OBP3 polypeptide are fused to each other so that both sequences fulfill the proposed function attributed to the sequence used.

"Homologs" are defined herein as two nucleic acids or proteins that have similar, or "homologous", nucleotide or amino acid sequences, respectively. Homologs include allelic variants, orthologs, paralogs, agonists and antagonists of OBP3s as defined hereafter. The term "homolog" further encompasses nucleic acid molecules that differ from the nucleotide sequence shown in SEQ ID NO:1 (and portions thereof) due to degeneracy of the genetic code and thus encode the same OBP3 protein as that encoded by the nucleotide sequences shown in SEQ ID NO:1. As used herein a "naturally occurring" OBP3 refers to an OBP3 amino acid sequence that occurs in nature. Preferably, a naturally occurring OBP3 comprises an amino acid sequence of SEQ ID NO:2.

The term "plant expression vector" as used herein refers to a nucleic acid sequence in which various regulatory elements, such as a promotor for, regulating expression of the gene of the present invention, are linked to each other so as to be operable in a host plant cell.

The term "plant promoter" as used herein refers to a promoter that functions in a plant.

The term "terminator" as used herein refers to a sequence positioned downstream of a region of a gene encoding a protein, which is involved in the termination of transcription of mRNA, and the addition of a poly A sequence. The terminator is known to contribute to the stability of mRNA, thereby affecting the expression level of a gene. Examples of such terminators include, but are not limited to, CaMV 35S terminator and a terminator of a nopaline synthase gene (Tnos).

The term "growing" or "regeneration" as used herein means growing a whole plant from a plant cell, a group of plant cells, a plant part (including seeds), or a plant piece (e.g., from a protoplast, callus, or tissue part).

DESCRIPTION OF THE PREFERRED EMBODIMENTS

Genes and Their Alleles and Homologs for Plant Phenotype Alteration Related to Size SOB1/OBP3is a member of the Dof family of transcription factors that, to date, remain unique to plants. Computer programs that predict gene function have identified more than 50 Dof transcription factors in the *Arabidopsis* genome (Riechmann, J. L. and Ratcliffe, O. J. (2000) Curr Opin Plant Bio 3:423-434). This family of transcriptional regulators shares a conserved DNA-binding domain made up of 52 amino acid residues in which a $CX_2CX_{21}CX_2C$ motif is predicted to form a single zinc finger, hence their name domain of one finger. These transcription factors are thought to have a common core recognition sequence of AAAG (Yanagisawa, S. and Schmidt, R. J. (1999) Plant J 17:209-214).

The present invention is based on the unexpected observation that a Dof transcription factor, and in particular OBP3, when expressed at levels other than those expressed in a wild-type plant, may affect the aerial growth of a plant without affecting the root growth of the same. An illustrative Dof transcription factor, OBP3 (also known as SOB1), is provided herein, although the invention is to be understood to include any Dof transcription factor having the activity as described for this illustrative species. The transcription factor OBP3 is involved in regulating the size and stature of a plant. Specifically, the present invention is based on the observation that increasing the amount of OBP3 results in plants that are smaller in size and stature than plants containing normal amounts of OBP3, while decreasing the amount of OBP3 leads to plants that are larger than plants with normal amounts of OBP3.

Based on these observations, one embodiment of the present invention provides methods for altering the size and stature of a plant which comprises the step of genetically altering the plant, using molecular techniques commonly known in the art, so the plant has an altered level of OBP3 when compared to a non-altered plant sufficient to alter the size and stature of the developing plant. Examples of such techniques are disclosed in the examples below. Examples of such alterations include alterations in the size of the aerial portion of the plant, including for example, alterations in the leaf, including alterations in the shape, color, and number of leaves, and the length of the petiole; alterations in the number, shape, and color of petals; alterations in branching; and alterations in the height. Alterations may also be effected in the non-aerial portions of the plant, including the root tissue and the hypocotyl. Examples of such alterations include, for example, alterations in root mass and length and alterations in hypocotyl mass and length. All above-mentioned alterations include both an increase and decrease in such characteristics. The reduced growth phenotype, commonly referred to as the dwarf phenotype, may be a useful trait for improving crop yield, for example, by reducing the shade-avoidance syndrome exhibited by many crop plants when grown at high density. Generally, in response to being within shade caused by nearby vegetation, plants will alter their architecture in an effort to escape the shaded area. As such, plants develop a shade avoidance response which is generally characterized by an increase in elongation growth, which is an inefficient use of a plant's resources, and thereby results in a decrease in the degree of branching and a shortened flowering period for the plant. www.kcl.ac.uk/kis/schools/life_sciences/life_sci/DevlinR.html. Reduction in shade avoidance allows a plant to utilize its resources more for growth and production of leaves, fruits and seeds, wasting less of its resources on stalk growth, and thereby results in a healthier and more productive plant. Reduction in shade avoidance also allows for higher density planting. In addition, the dwarf phenotype may also be used, for example, to generate varieties of horticultural plants with semi-dwarfed aerial portions and normal roots, such as for example, turfgrass with semi-dwarf blades and normal roots. Such would allow for a denser growing grass (i.e., a greater number of blades per unit of soil).

Accordingly, one embodiment of the invention is a transgenic plant cell transformed by a nucleic acid sequence encoding an OBP3 polypeptide, wherein expression of said polypeptide in the plant cell results in an alteration in the size of the resulting aerial portion of a plant generated from the cell without dwarfing root tissue as compared to a corresponding wild-type variety of plant. In another embodiment of the invention, the polypeptide is over-expressed resulting in a decrease in the size of the resulting aerial portion of the plant as compared to a corresponding wild-type variety of plant. In yet another embodiment of the invention, the OBP3 is *Arabidopsis thaliana* OBP3 and orthologs thereof.

In a particular embodiment of the invention, the nucleic acid sequence encoding the polypeptide is selected from the group consisting of (a) the nucleotide sequence shown in SEQ ID NO:1, or the complement thereof; (b) a nucleotide sequence that hybridizes to said nucleotide sequence of (a) under a wash stringency equivalent to 0.1×SSC to 2.0×SSC, 0.1% SDS, at 50-65° C., and which encodes a polypeptide having activity differing from that of *Arabidopsis thaliana* OBP3 by about 40% or less; (c) a nucleotide sequence encoding the same amino acid sequence as said nucleotide sequence of (a), but which is degenerate in accordance with the degeneracy of the genetic code; and (d) a nucleotide sequence encoding the same amino acid sequence as said nucleotide sequence of (b), but which is degenerate in accordance with the degeneracy of the genetic code. In another embodiment, the nucleic acid sequence encoding the polypeptide encodes a polypeptide having activity differing from that of *Arabidopsis thaliana* OBP3 by about 30% or less. In another embodiment, the nucleic acid sequence encoding the polypeptide encodes a polypeptide having activity differing from that of *Arabidopsis thaliana* OBP3 by about 20% or less. In another embodiment, the nucleic acid sequence encoding the polypeptide encodes a polypeptide having activity differing from that of *Arabidopsis thaliana* OBP3 by about 10% or less.

Likewise, plants may be grown that demonstrate an increase in the size of the aerial portion of the plant. Such is achieved by repressing the expression of OBP3 in the plant. Accordingly, one embodiment of the invention comprises a transgenic plant cell transformed by an antisense nucleic acid sequence complementary to a nucleic acid sequence encoding an OBP3 polypeptide, wherein said antisense nucleic acid sequence results in an increase in the size of a resulting plant as compared to a corresponding wild-type variety of plant. In another embodiment, the OBP3 is *Arabidopsis thaliana* OBP3 and orthologs thereof.

In a particular embodiment of the invention, the nucleic acid sequence encoding the OBP3 polypeptide is selected from the group consisting of: (a) the nucleic acid sequence shown in SEQ ID NO:1, or the complement thereof; (b) a nucleic acid sequence that hybridizes to said nucleotide sequence of (a) under a wash stringency equivalent to 0.1×SSC to 2.0×SSC, 0.1% SDS, at 50-65° C., and which encodes a polypeptide having activity differing from that of *Arabidopsis thaliana* OBP3 by about 40% or less; (c) a nucleic acid sequence encoding the same amino acid sequence as said nucleotide sequence of (a), but which is degenerate in accordance with the degeneracy of the genetic code; and (d) a nucleic acid sequence encoding the same amino acid sequence as said nucleotide sequence of (b), but which is degenerate in accordance with the degeneracy of the genetic code. In another embodiment, the nucleic acid encoding the polypeptide encodes a polypeptide having activity differing from that of *Arabidopsis thaliana* OBP3 by about 30% or less. In another embodiment, the nucleic acid encoding the polypeptide encodes a polypeptide having activity differing from that of *Arabidopsis thaliana* OBP3 by about 20% or less. In another embodiment, the nucleic acid encoding the polypeptide encodes a polypeptide having activity differing from that of *Arabidopsis thaliana* OBP3 by about 10% or less.

Any plant that can be genetically altered using molecular techniques and any plants propagated containing the genetic alteration can be used in the present method. Such plants can also be altered according to the present invention. Methods known in the art for molecularly altering a plant are discussed in detail below. The preferred plants include both dicot and monocotyledonous plants. The most preferred plants are plants with economic value as a food or biomass source, or horticultural plants. Such plants include, but are not limited to, turfgrasses, leafy plants such as tobacco, spinach, and lettuce, maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and forage crops and seed bearing plants such as rice, corn, soy bean, etc.

Moreover, the present invention includes transgenic plants and plant parts, such as for example, seeds, fruits, leaves, and flowers, comprising the transgenic plant cells. Additionally, the present invention includes agricultural products produced from the transgenic plant cells, plant parts, or plants disclosed herein.

The methods of the present invention rely on altering plants using molecular techniques. Molecular techniques refers to procedures in which DNA is manipulated in a test tube during at least one stage of the process, such as the direct manipulation of DNA or the use of shuttle host such as bacterium. Additional examples of molecular techniques include, for example, methods of using PCR to multiply a nucleic acid of interest for introduction and expression in a plant or plant cell via expression vectors or direct introduction of the nucleic acid; methods of using nucleic acid libraries to determine, isolate, introduce, and express a nucleic acid of interest into a plant or plant cell via expression vectors or direct introduction of the nucleic acid; isolation of nucleic acid segments, concatemerization of said nucleic acid segments into a larger nucleic acid, introduction, and expression of the same in a plant or plant cell via expression vectors or direct introduction of the nucleic acid; and isolation of mRNA from a gene, creation of cDNA from the mRNA by reverse transcription, and introduction and expression of the same in a plant or plant cell via expression vectors or direct introduction of the nucleic acid. Such methods are well known in the art and are described in, for example, Sambrook, et al., Molecular Cloning: a Laboratory Manual, Cold Spring Harbor Press (1989). Some of the techniques that are used to alter a plant are discussed in more detail below. Molecular techniques are differentiated from classical genetics in which randomly occurring spontaneous mutants or classical mutagenic techniques are applied to a given plant type. Some altered plants are presently known in the art that have been generated through non-molecular techniques such as random mutation.

It should be noted that the present invention encompasses not only the specific DNA sequences disclosed herein and the polypeptides encoded thereby, but also biologically functional equivalent nucleotide and amino acid sequences. The phrase "biologically functional equivalent nucleotide sequences" denotes DNAs and RNAs, including chromosomal DNA, plasmid DNA, cDNA, synthetic DNA, and mRNA nucleotide sequences, that encode polypeptides exhibiting the same or similar activity as that of the enzyme polypeptides encoded by the sequences disclosed herein when assayed by standard methods, or by complementation. Such biologically functional equivalent nucleotide sequences can encode polypeptides that contain a region or moiety exhibiting sequence similarity to the corresponding region or moiety of the presently disclosed polypeptides.

One can isolate polypeptides useful in the present invention from various organisms based on homology or sequence identity. Although particular embodiments of nucleotide sequences encoding the polypeptides disclosed herein are shown in the various SEQ IDs presented, it should be understood that other biologically functional equivalent forms of such polypeptide-encoding nucleic acids can be readily isolated using conventional DNA-DNA or DNA-RNA hybridization techniques. Thus, the present invention also includes nucleotide sequences that hybridize to any of the nucleic acid SEQ IDs and their complementary sequences presented herein, and that code on expression for polypeptides exhibiting the same or similar activity as that of the presently disclosed polypeptides. Such nucleotide sequences preferably hybridize to the nucleic acid sequences presented herein or their complementary sequences under moderate to high stringency as disclosed above (see Sambrook et al., 1989).

The present invention also encompasses nucleotide sequences that hybridize under salt and temperature conditions equivalent to those described above to genomic DNA, plasmid DNA, cDNA, or synthetic DNA molecules that encode the same amino acid sequences as these nucleotide sequences, and genetically degenerate forms thereof due to the degenerancy of the genetic code, and that code on expression for a polypeptide that has the same or similar activity as that of the polypeptides disclosed herein.

Using the above-described molecular techniques, and others known to those of skill in the art, one of ordinary skill in the art can isolate homologs of OBP3 comprising the amino acid sequence shown in SEQ ID NO:2. Said homologs would be useful in the present methods. Preferably, the homologs will have an amino acid sequence that exhibits at least 80-85%, more preferably 90%, and most preferably 95%, 96%, 97%, 98% or even 99% identity or homology with all or part of the *Arabidopsis thaliana* OBP3. Preferably, the homologs will also have an activity differing from that of *Arabidopsis thaliana* OBP3 by about 40% or less; more preferably by about 30% or less, even more preferably by about 20% or less, and most preferably by about 10% or less. Sequence identity can be determined using the "BestFit" or "Gap" programs of the Sequence Analysis Software Package, Genetics Computer Group, Inc., University of Wisconsin Biotechnology Center, Madison, Wis. 53711.

One subset of these homologs is allelic variants. Allelic variants can be identified by sequencing the nucleic acid sequence of interest in a number of different plants, which can be readily carried out by using hybridization probes to identify the same OBP3 genetic locus in those plants. Any and all such nucleic acid variations and resulting amino acid polymorphisms or variations in OBP3 that are the result of natural allelic variation and that do not alter the functional activity of OBP3, are intended to be within the scope of the invention.

Moreover, nucleic acid molecules encoding OBP3 from the same or other species such as OBP3 analogs, orthologs and paralogs, are intended to be within the scope of the present invention. These nucleic acid molecules can be isolated according to the methods disclosed above. Analogs, orthologs and paralogs of a naturally occurring OBP3 can differ from the naturally occurring OBP3 by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably 90%, and most preferably 95%, 96%, 97%, 98% or even 99% identity or homology with all or part of a naturally occurring OBP3 amino acid sequence and will exhibit a function similar to OBP3. Preferably, the orthologs will also have an activity differing from that of *Arabidopsis thaliana* OBP3 by about 40% or less; more preferably by about 30% or less, even more preferably by about 20% or less, and most preferably by about 10% or less. Orthologs of the present invention are also preferably capable of participating in determining the size of plants. Sequence identity may be determined as described above.

In addition to naturally-occurring variants of an OBP3 sequence that may exist in the population, the skilled artisan will further appreciate that changes can be introduced by mutation into the nucleotide sequence of SEQ ID NO:1, thereby leading to changes in the amino acid sequence of the encoded OBP3, without altering the functional ability of the OBP3. For example, nucleotide substitutions leading to amino acid substitutions at "non-essential" amino acid residues can be made in the sequence of SEQ ID NO:2. A "non-essential" amino acid residue is a residue that can be altered from the wild-type sequence of OBP3 without altering the activity of said OBP3, whereas an "essential" amino acid residue is required for OBP3 activity. Other amino acid residues, however, (e.g., those that are not conserved or only semi-conserved in the domain having OBP3 activity) may not be essential for activity and thus are likely to be amenable to alteration without altering OBP3 activity.

Biologically functional equivalent nucleotide sequences of the present invention also include nucleotide sequences that encode conservative amino acid changes within the amino acid sequences of the present polypeptides, producing silent changes therein. Such nucleotide sequences thus contain corresponding base substitutions based upon the genetic code compared to the nucleotide sequences encoding the present polypeptides. Substitutes for an amino acid within the fundamental polypeptide amino acid sequences discussed herein can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cyteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid changes within the present polypeptide sequences can be made by substituting one amino acid within one of these groups with another amino acid within the same group. The encoding nucleotide sequences (gene, plasmid DNA, cDNA, synthetic DNA, or mRNA) will thus have corresponding base substitutions, permitting them to code on expression for the biologically functional equivalent forms of the present polypeptides.

Accordingly, another embodiment of the invention is an isolated nucleic acid molecule comprising a nucleotide sequence selected from the group consisting of (a) the nucleotide sequence shown in SEQ ID NO:1, or the complement thereof; (b) a nucleotide sequence that hybridizes to said nucleotide sequence of (a) under a wash stringency equivalent to 0.1×SSC to 2.0×SSC, 0.1% SDS, at 50-65° C., and which encodes a polypeptide having activity differing from that of *Arabidopsis thaliana* OBP3 by about 40% or less; (c) a nucleotide sequence encoding the same amino acid sequence as said nucleotide sequence of (a), but which is degenerate in accordance with the degeneracy of the genetic code; and (d) a nucleotide sequence encoding the same amino acid sequence as said nucleotide sequence of (b), but which is degenerate in accordance with the degeneracy of the genetic code. In another embodiment, the nucleotide sequence in (b) encodes a polypeptide having activity differing from that of *Arabidopsis thaliana* OBP3 by about 30% or less. In another embodiment, the nucleotide sequence in (b) encodes a polypeptide having activity differing from that of *Arabidopsis thaliana* OBP3 by about 20% or less. In another embodiment, the nucleotide sequence in (b) encodes a polypeptide having activity differing from that of *Arabidopsis thaliana* OBP3 by about 10% or less. Another aspect of the invention is plants, plant cells, plant parts, such as for example, seeds, fruits, leaves, and flowers, agricultural products, host cells, and vectors comprising one or more of the disclosed nucleic acid sequences.

Another aspect of the invention pertains to nucleic acid molecules encoding OBP3 that contains changes in amino acid residues that are not essential for OBP3 activity. Such OBP3 differs in amino acid sequence from a sequence contained in SEQ ID NO:2, yet retain at least one of the OBP3 activities described herein. In one embodiment, the isolated nucleic acid molecule comprises a nucleotide sequence encoding a protein, wherein the protein comprises an amino acid sequence at least about 50% homologous to the amino acid sequence of SEQ ID NO:2. Preferably, the protein encoded by the nucleic acid molecule is at least about 50-60% homologous to the sequence of SEQ ID NO:2, more preferably at least about 60-70% homologous to the sequence of SEQ ID NO:2, even more preferably at least about 70-80%, 80-90%, 90-95% homologous to the sequence of SEQ ID NO:2, and most preferably at least about 96%, 97%, 98%, or 99% homologous to the sequence of SEQ ID NO:2. The differences in homology of the amino acid sequences may be a result of conservative amino acid changes or substitutions. The preferred OBP3 homologs of the present invention are capable of participating in the developmental pathway affecting the size of a plant or participating in the transcription of a protein involved in the developmental pathway affecting the size of a plant.

Accordingly, one embodiment of the invention is an isolated protein that exhibits at least one activity of OBP3, selected from the group consisting of (a) SEQ ID NO: 2; (b) a protein having an amino acid sequence which includes the amino acid sequence of SEQ ID NO: 2; and (c) a protein including an amino acid sequence wherein at least 60% of the amino acids of the amino acid sequence correspond to the amino acid sequence of SEQ. ID NO. 2. In another embodiment of the invention, the isolated protein is a protein including an amino acid sequence wherein at least 70% of the amino acids of the amino acid sequence correspond to the amino acid sequence of SEQ. ID NO. 2. In another embodiment of the invention, the isolated protein is a protein including an amino acid sequence wherein at least 80% of the amino acids of the amino acid sequence correspond to the amino acid sequence of SEQ. ID NO. 2. In another embodiment of the invention, the isolated protein is a protein including an amino acid sequence wherein at least 85% of the amino acids of the amino acid sequence correspond to the amino acid sequence of SEQ. ID NO. 2. In another embodiment of the invention, the isolated protein is a protein including an amino acid sequence wherein at least 90% of the amino acids of the amino acid sequence correspond to the amino acid sequence of SEQ. ID NO. 2. In another embodiment of the invention, the isolated protein is a protein including an amino acid sequence wherein at least 95% of the amino acids of the amino acid sequence correspond to the amino acid sequence of SEQ. ID NO. 2. In another embodiment of the invention, the isolated protein is a protein including an amino acid sequence wherein at least 98% of the amino acids of the amino acid sequence correspond to the amino acid sequence of SEQ. ID NO. 2.

Another embodiment of the invention is a polypeptide encoded by a nucleic acid sequence encoding an OBP3 polypeptide, said nucleic acid sequence selected from the group consisting of (a) the nucleotide sequence shown in SEQ ID NO:1, or the complement thereof; (b) a nucleotide sequence that hybridizes to said nucleotide sequence of (a) under a wash stringency equivalent to 0.1×SSC to 2.0×SSC, 0.1% SDS, at 50-65° C., and which encodes a polypeptide having activity differing from that of *Arabidopsis thaliana* OBP3 by about 40% or less; (c) a nucleotide sequence encoding the same amino acid sequence as said nucleotide sequence of (a), but which is degenerate in accordance with the degeneracy of the genetic code; and (d) a nucleotide sequence encoding the same amino acid sequence as said nucleotide sequence of (b), but which is degenerate in accordance with the degeneracy of the genetic code. In another embodiment, the nucleotide sequence in (b) encodes a polypeptide having activity differing from that of *Arabidopsis thaliana* OBP3 by about 30% or less. In another embodiment, the nucleotide sequence in (b) encodes a polypeptide having activity differing from that of *Arabidop-* *sis thaliana* OBP3 by about 20% or less. In another embodiment, the nucleotide sequence in (b) encodes a polypeptide having activity differing from that of *Arabidopsis thaliana* OBP3 by about 10% or less.

Moreover, the nucleic acid molecule of the invention can comprise only a portion of the coding region of the sequence in SEQ ID NO:1, for example, a fragment which can be used as a probe or primer or a fragment encoding a biologically active portion of OBP3. The nucleotide sequences determined from the cloning of the OBP3 gene from *Arabidopsis thaliana* allows for the generation of probes and primers designed for use in identifying and/or cloning OBP3 homologs in other cell types and organisms, as well as OBP3 homologs from other plants and related species. The methods for determining the proper primer or probe are commonly known in the art (see Sambrook, et al., Molecular Cloning: a Laboratory Manual, Cold Spring Harbor Press (1989)).

Portions of proteins encoded by the OBP3 nucleic acid molecule of the invention are preferably biologically active portions of the OBP3 described herein. To determine whether OBP3 or a biologically active portion thereof, can participate in transcription of a protein involved in the developmental pathway affecting the size of a plant, or whether repression of OBP3 results in increased size of a plant, an analysis of a plant comprising the OBP3 may be performed. More specifically, nucleic acid fragments encoding biologically active portions of OBP3 can be prepared by isolating a portion of one of the sequences in SEQ ID NO:1, expressing the encoded portion of the OBP3 or peptide (e.g., by recombinant expression in vitro) and assessing the phentoype of the plant resulting from the expression or repression of the encoded portion of the OBP3 or peptide.

Biologically active portions of OBP3 are encompassed by the present invention and include peptides comprising amino acid sequences derived from the amino acid sequence of OBP3, e.g., an amino acid sequence of SEQ ID NO:2, or the amino acid sequence of a protein homologous to OBP3, which include fewer amino acids than a full length OBP3 or the full length protein which is homologous to OBP3, and exhibit at least one activity of OBP3. Typically, biologically active portions (e.g., peptides which are, for example, 5, 10, 15, 20, 30, 35, 36, 37, 38, 39, 40, 50, 100 or more amino acids in length) comprise a domain or motif with at least one activity of OBP3. Moreover, other biologically active portions in which other regions of the protein are deleted, can be prepared by recombinant techniques and evaluated for one or more of the activities described herein. Preferably, the biologically active portions of OBP3 include one or more selected domains/motifs or portions thereof having biological activity.

Another aspect of the invention is OBP3 chimeric or fusion proteins. A non-OBP3 polypeptide can be fused to the N-terminus or C-terminus of the OBP3 polypeptide. For example, in one embodiment, the fusion protein is a GST-OBP3 fusion protein in which the OBP3 sequence is fused to the C-terminus of the GST sequence. Such fusion proteins can facilitate the purification of recombinant OBP3. In another embodiment, the fusion protein is a OBP3 containing a heterologous signal sequence at its N-terminus. In certain host cells (e.g., mammalian host cells), expression and/or secretion of OBP3 can be increased through use of a heterologous signal sequence.

Preferably, an OBP3 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, Eds. Ausubel et al. John Wiley & Sons, 1992). Moreover, many expression vectors are commercially available that already encode a fusion moiety (e.g., a GST polypeptide, a metal ion affinity tag, a c-myc epitope tag, etc.). A OBP3 encoding nucleic acid can be cloned into such an expression vector such that the fusion moiety is linked in-frame to the OBP3.

In addition to fragments and fusion proteins of OBP3 described herein, the present invention includes homologs and analogs of naturally occurring OBP3 and OBP3 encoding nucleic acids in a plant.

An agonist of OBP3 can retain substantially the same, or a subset, of the biological activities of OBP3. An antagonist of OBP3 can inhibit one or more of the activities of the naturally occurring form of OBP3. For example, the OBP3 antagonist can competitively bind to a downstream or upstream member of the cellular signaling cascade that includes OBP3.

Nucleic acid molecules corresponding to natural allelic variants and analogs, orthologs and paralogs of an OBP3 cDNA can be isolated based on their identity to the *Arabidopisis thaliana* OBP3 nucleic acids described herein using OBP3 cDNAs, or a portion thereof, as a hybridization probe according to standard hybridization techniques under stringent hybridization conditions. In an alternative embodiment, homologs of OBP3 can be identified by screening combinatorial libraries of mutants, e.g., truncation mutants, of the OBP3 for OBP3 agonist or antagonist activity. In one embodiment, a variegated library of OBP3 variants is generated by combinatorial mutagenesis at the nucleic acid level and is encoded by a variegated gene library. A variegated library of OBP3 variants can be produced by, for example, enzymatically ligating a mixture of synthetic oligonucleotides into gene sequences such that a degenerate set of potential OBP3 sequences is expressible as individual polypeptides, or alternatively, as a set of larger fusion proteins (e.g., for phage display) containing the set of OBP3 sequences therein. There are a variety of methods that can be used to produce libraries of potential OBP3 homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential OBP3 sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of OBP3 coding regions can be used to generate a variegated population of OBP3 fragments for screening and subsequent selection of homologs of OBP3. In one embodiment, a library of coding sequence fragments can be generated by treating a double stranded PCR fragment of an OBP3 coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of OBP3.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of OBP3 homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify OBP3 homologs (Arkin and Yourvan (1992) Proc Natl Acad Sci USA 89:7811-7815; Delgrave et al. (1993) Protein Eng 6:327-331).

Expression Vectors

The polynucleotide sequences of the present invention can also be part of an expression cassette or vector that comprises, operably linked in the 5' to 3' direction, a promoter, a polynucleotide of the present invention, and a transcriptional termination signal sequence functional in a host cell. The promoter can be of any of the types discussed herein, for example, a tissue specific promoter, a developmental regulated promoter, an organelle specific promoter, a seed specific promoter, a plastid specific promoter, etc. The expression cassette or vector can further comprise an operably linked targeting, transit or secretion peptide coding region capable of directing transport of the protein produced. The expression cassette or vector can also further comprise a nucleotide sequence encoding a selectable marker and a purification moiety. In addition, the expression cassette or vector can further comprise an additional sequence encoding an enzyme capable of cleaving the polypeptide of the present invention between the tandem repeats in order to produce non-repeating peptide units. The enzyme encoding sequence can be under the control of a separate promoter, for example an inducible or developmentally regulated promoter so that production of the enzyme is triggered only after substantial amounts of the repeating polypeptide of the present invention has been produced Accordingly, in one embodiment, the expression vector comprises an OBP3 polypeptide encoding nucleic acid sequence. In another embodiment, the expression vector comprises an antisense nucleic acid sequence encoding a nucleic acid complementary to the OBP3 polypeptide encoding nucleic acid sequence. A nucleic acid sequence that encodes OBP3 can be operably linked to expression control sequences. An expression control sequence operably linked to a coding sequence is ligated such that expression of the coding sequence is achieved under conditions compatible with the expression control sequences. As used herein, the term "expression control sequence" refers to a nucleic acid sequence that regulates the expression of a nucleic acid sequence to which it is operably linked. Expression control sequences are operably linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, a splicing signal for introns or maintenance of the correct reading frame of that gene to permit proper translation of mRNA, and stop codons. The term "control sequences" is intended to comprise components whose presence can influence expression, and can also include additional components whose presence is advantageous, for example, leader sequences and fusion partner sequences. Expression control sequences can include a promoter.

As provided above, several embodiments of the present invention employ expression units (or expression vectors or systems) to express an exogenously supplied gene, such as OBP3, or antisense molecule, in a plant. Such expression units may also be referred to as expression cassettes. Methods for generating expression units/systems/vectors for use in plants are well known in the art and can readily be adapted for use in altering the amount of OBP3 present in a plant cell. Typically, such units employ a protein, nucleotide sequence, or antisense coding region, such as the OBP3 *Arabidopsis* gene, or a homologue thereof, and one or more expression control elements. The choice of the protein/nucleotide sequence/antisense coding region, as well as the control elements, employed will be based on the effect desired (i.e., reduction or increase in the amount of OBP3), the plant that is to be altered, the method chosen for altering the amount of OBP3 and the transformation system used. A skilled artisan can readily use any appropriate plant/vector/expression system in the present methods following the outline provided herein.

The expression control elements used to regulate the expression of the protein or antisense coding region can either be the expression control element that is normally found associated with the coding sequence (homologous_ expression element) or can be a heterologous expression control element. A variety of homologous and heterologous expression control elements are known in the art and can readily be used to make expression units for use in the present invention. Expression control elements include, for example, promoters, enhancers, and termination signal sequences. Transcription initiation regions, for example, can include any of the various opine initiation regions, such as octopine, mannopine, nopaline and the like that are found in the Ti plasmids of *Agrobacterium tumafacians*. Alternatively, plant viral promoters viral promoters can also be used, such as the cauliflower mosaic virus 35S promoter to control gene expression in a plant. In addition, plant promoters such as prolifera promoter, fruit-specific promoters, Ap3 promoter, heat shock promoters, seed-specific promoters, etc. can also be used. The most preferred promoters will be active in dividing tissue, particularly meristematic cells.

Included within the meaning of promoter is a sequence sufficient to direct transcription. Also included are those promoter elements which are sufficient to render promoter-dependent gene expression controllable for cell-type specific, tissue-specific, environmentally- or developmentally-regulated, or expression that is inducible by external signals or agents. Such elements may be located in the 5' or 3' regions of the gene. Both constitutive and inducible promoters, are included in the invention (see e.g., Bitter et al., *Methods in Enzymology* (1987) 153:516-544).

The expression of structural genes employed in the present invention may be driven by a number of promoters. Although the endogenous promoter of a structural gene of interest, for example of the OBP3 gene, may be utilized for transcriptional regulation of the gene, the promoter may also be a foreign regulatory sequence. For plant expression vectors, suitable viral promoters include the 35S RNA and 19S RNA promoters of CaMV (Brisson et al., *Nature* (1984) 310:511; Odell et al., *Nature* (1985) 313:810); the enhanced CaMV 35S promoter; the Figwort Mosaic Virus (FMV) promoter (Gowda et al., *J. Cell Biochem.* (1989) 13D:301; Richins et al., *Nucleic Acids Res.* (1987) 15(20): 8451-66) and the coat protein promoter of TMV (Takamatsu et al., *EMBO J.* (1987) 6:307). Alternatively, plant promoters such as the light-inducible promoter from the small subunit of ribulose bis-phosphate carboxylase (ssRUBISCO) (Coruzzi et al., *EMBO J.* (1984) 3:1671; Broglie et al., *Science* (1984) 224:838); mannopine synthase (MAS) promoter (Velten et al., *EMBO J.* (1984) 3:2723), nopaline synthase (NOS) and octopine synthase (OCS) promoters (carried on tumor-inducing plasmids of *Agrobacterium tumefaciens* and having plant activity); ethylene inducible promoter whose level of activity is increased in response to treatment with ethylene or an equivalent compound such as propylene; heat shock promoters, e.g., soybean hsp17.5-E or hsp17.3-B (Gurley et al., *Mol. Cell. Biol.* (1986) 6:559; Severin et al., *Plant Mol. Biol.* (1990) 15:827; Ou-Lee et al., *Proc. Natl. Acad. Sci. USA* (1986) 83: 6815; Ainley et al., *Plant Mol. Biol.* (1990) 14: 949); a nitrate-inducible promoter derived from the spinach nitrite reductase gene (Back et al., *Plant Mol. Biol.* (1991) 17: 9); hormone inducible promoters (Yamaguchi-Shinozaki et al., *Plant Mol. Biol.* (1990) 15: 905; Kares et al., *Plant Mol. Biol.* (1990) 15: 905) or ethanol-inducible promoters (Caddick et al., *Nature Biotech.* (1998) 16:177) may be used.

Examples of useful tissue specific, developmentally-regulated promoters include the β-conglycinin 7S promoter (Doyle et al., *J. Biol. Chem.* (1986) 261: 9228; Slighton and Beachy, *Planta* (1987)172: 356), and seed-specific promoters (Knutzon et al., *Proc. Natl. Acad. Sci. USA* (1992) 89: 2624; Bustos et al., *EMBO J.* (1991) 10: 1469; Lam and Chua, *Science* (1990) 248: 471; Stayton et al., *Aust. J. Plant. Physiol.* (1991) 18: 507). Plant functional promoters useful for preferential expression in seed plastids include, for example, those from plant storage protein genes and from genes involved in fatty acid biosynthesis in oilseeds. Examples of such promoters include the 5' regulatory regions from such genes as napin (Kridl et al., *Seed Sci. Res.* (1991) 1: 209), phaseolin, zein, soybean trypsin inhibitor, ACP, stearoyl-ACP desaturase, and oleosin. Seed-specific gene regulation is discussed in EP 0 255 378. Promoter hybrids can also be constructed to enhance transcriptional activity (Hoffman, U.S. Pat. No. 5,106,739), or to combine desired transcriptional activity and tissue specificity.

Tissue specific promoters may also be utilized in the present invention. As used herein, the term "tissue-specific promoter" means a DNA sequence that serves as a promoter, i.e., regulates expression of a selected DNA sequence operably linked to the promoter. A tissue-specific promoter effects expression of the selected DNA sequence in specific cells, e.g., in the root or in the shoot of a plant. The term also covers so-called "leaky" promoters, which regulate expression of a selected DNA primarily in one tissue, but cause expression in other tissues as well. Such promoters also may include additional DNA sequences that are necessary for expression, such as introns and enhancer sequences. These additional sequences may be either endogenous to the organism from which the promoter is derived, endogenous to the plant which is being transformed, or may be exogenous to both. An example of a tissue specific promoter is the HHA promoter expressed in shoot meristems (Atanassova et al., *Plant J.* (1992) 2:291). Other tissue specific promoters useful in transgenic plants, including the cdc2a promoter and cyc07 promoter, will be known to those of skill in the art. (See for example, Ito et al., *Plant Mol. Biol.* (1994) 24:863; Martinez et al., *Proc. Natl. Acad. Sci. USA* (1992) 89:7360; Medford et al., *Plant Cell* (1991) 3:359; Terada et al., *Plant J.* (1993) 3:241; Wissenbach et al., *Plant J.* (1993) 4:411). Examples of tissue specific promoters active in floral meristems are the promoters of the apetala 3 and apetala 1 genes which are described in Jack et al., *Cell* (1994) 76:703 and Hempel et al., *Development* (1997) 124:3845. In addition, a meristem-specific promoter from the UFO gene (U.S. Pat. No. 5,880,330) may be useful in the practice of the invention.

Promoters useful in the invention include both constitutive and inducible natural promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter, which is activated by copper ions (Mett et al., *Proc. Natl. Acad. Sci., U.S.A.* (1993) 90:4567); In2-1 and In2-2 regulator sequences, which are activated by substituted benzenesulfonamides, e.g., herbicide safeners (Hershey et al., *Plant Mol. Biol.* (1991) 17:679); the GRE regulatory sequences, which are induced by glucocorticoids (Schena et al., *Proc. Natl. Acad. Sci., U.S.A.* (1991) 88:10421); and ethanol-inducible promoters (Caddick et al., *Nature Biotech.* (1998) 16:177). Other promoters, both constitutive and inducible, and enhancers will be known to those of skill in the art.

The particular promoter selected should be capable of causing sufficient expression to result in the over-expression of the OBP3 gene product, e.g., OBP3 polypeptide, to decrease the size of the aerial portion of a plant. The promoters used in the vector constructs of the present invention may be modified, or located at different positions within a construct, if desired, to affect their control characteristics. In a preferred approach, multimerized copies of enhancer elements from the cauliflower mosaic virus (CaMV) 35S promoter are incorporated into the OBP3 gene or expression construct, and more preferably near (e.g., within 381 nucleotides) 5' to the start of the OBP3 gene. When these enhancers are inserted near a gene, its transcription can be enhanced.

Either a constitutive promoter (such as the CaMV or Nos promoter illustrated above), an organ-specific promoter (such as the E8 promoter from tomato) or an inducible promoter is typically ligated to the protein or antisense encoding region using standard techniques known in the art. The promoter may be operably linked to the protein, nucleic acid, or antisense coding region in any manner known to one of skill in the art. The expression unit may be further optimized by employing supplemental elements such as transcription terminators and/or enhancer elements.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., *EMBO J* (1984) 3:835-846) or the nopaline synthase signal (Depicker et al., *Mol. and Appl. Genet.* (1982) 1:561-573).

Thus, for expression in plants, the expression units will typically contain, in addition to the protein, nucleic acid sequence, or antisense coding sequence, a plant promoter region, a transcription initiation site and a transcription termination sequence. Alternatively, the expression unit may contain, in addition to a protein, a nucleic acid sequence, or an antisense coding sequence, a promoter, one or more enhancers or enhancer elements, a transcription initiation site, and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

Accordingly, one embodiment of the invention is a recombinant expression vector comprising a promoter, said promoter being functional in a plant cell; and nucleic acid sequence encoding an OPB3 polypeptide, wherein said nucleic acid sequence is operably linked to said promoter wherein said nucleic acid comprises a nucleic acid sequence of at least 15 contiguous nucleic acids of SEQ ID NO:1. In another embodiment, the nucleic sequence comprises a nucleic acid sequence selected from the group consisting of: (a) the nucleotide sequence shown in SEQ ID NO:1, or the complement thereof; (b) a nucleotide sequence that hybridizes to said nucleotide sequence of (a) under a wash stringency equivalent to 0.1×SSC to 2.0×SSC, 0.1% SDS, at 50-65° C., and which encodes a polypeptide having activity differing from that of *Arabidopsis thaliana* OBP3 by about 40% or less; (c) a nucleotide sequence encoding the same amino acid sequence as said nucleotide sequence of (a), but which is degenerate in accordance with the degeneracy of the genetic code; and (d) a nucleotide sequence encoding the same amino acid sequence as said nucleotide sequence of (b), but which is degenerate in accordance with the degeneracy of the genetic code. In another embodiment, the nucleotide sequence of (b) encodes a polypeptide having activity differing from that of *Arabidopsis thaliana* OBP3 by about 30% or less. In another embodiment, the nucleotide sequence of (b) encodes a polypeptide having activity differing from that of *Arabidopsis thaliana* OBP3 by about 20% or less. In another embodiment, the nucleotide sequence of (b) encodes a polypeptide having activity differing from that of *Arabidopsis thaliana* OBP3 by about 10% or less.

The resulting expression unit is ligated into or otherwise constructed to be included in a vector which is appropriate for higher plant transformation. In plants, transformation vectors capable of introducing nucleic acid sequences encoding OBP3 are easily designed, and generally contain one or more nucleic acid sequences of interest under the transcriptional control of 5' and 3' regulatory sequences. Such vectors generally comprise, operably linked in sequence in the 5' to 3' direction, a promoter sequence that directs the transcription of a downstream heterologous structural DNA in a plant; optionally, a 5' non-translated leader sequence; a nucleic acid sequence that encodes a protein of interest; and a 3' non-translated region that encodes a polyadenylation signal which functions in plant cells to cause the termination of transcription and the addition of polyadenylate nucleotides to the 3' end of the mRNA encoding said protein. Typical 5'-3' regulatory sequences include a transcription initiation start site, a ribosome binding site, an RNA processing signal, a transcription termination site, and/or a polyadenylation signal. Vectors for plant transformation have been reviewed in Rodriguez et al. (1988), Glick et al. (1993), and Croy (1993).

The vector will also typically contain a selectable marker gene by which transformed plant cells can be identified in culture. The marker may generally be associated with the heterologous nucleic acid sequence, i.e., the structural gene operably linked to a promoter. As used herein, the term "marker" refers to a gene encoding a trait or a phenotype that permits the selection of, or the screening for, a plant or plant cell containing the marker. Usually, the marker gene will encode antibiotic resistance. This allows for selection of transformed cells from among cells that are not transformed. Alternatively, the marker gene may be a herbicide resistance gene. The marker gene may be an antibiotic resistance gene that allows the appropriate antibiotic to be used to select for transformed cells from among cells that are not transformed, or the marker gene may be a herbicide resistance gene. Examples of suitable selectable markers include adenosine deaminase, dihydrofolate reductase, hygromycin-B-phosphotransferase, thymidine kinase, xanthine-guanine phospho-ribosyltransferase, glyphosphate and glufosinate resistance and amino-glycoside 3'-O-phosphotransferase II (kanamycin, neomycin and G418 resistance). These markers include resistance to G418, hygromycin, bleomycin, kanamycin, and gentamicin. Other suitable markers will be known to those of skill in the art.

Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

Preferably, the plant expression vector may include a plant promoter, a terminator, a drug resistant gene and more than one enhancer. It is well known to those skilled in the art that a type of the plant expression vector and regulator elements may be varied depending on the type of host cell. A plant expression vector used according to the present invention may further contain a T-DNA region. The T-DNA region allows a gene to be efficiently introduced into plant genome especially when *Agrobacterium* is used to transform a plant.

Constitutive promoters as well as tissue-specific promoters which selectively function in a part of a plant body, including a flower, are preferable. Examples of plant promoters include, but are not limited to, Cauliflower mosaic virus (CaMV) 35S promoter and a promoter of nopaline synthase.

A drug resistant gene is desirable to facilitate the selection of transgenic plants. The examples of such drug resistant genes for use in the invention include, but are not limited to, a neomycin phosphotransferase II (NPTII) gene for conferring kanamycin resistance, and a hygromycin phosphotransferase gene for conferring hygromycin resistance.

An enhancer may be used to enhance the expression level of a gene of interest. As the enhancer, an enhancer region containing a sequence upstream of the above-mentioned CaMV 35S promoter is preferable. More than one enhancer may be used in one plant expression vector.

The plant expression vector according to the present invention may be produced by using a recombinant DNA technique well known to those skilled in the art. The examples of preferable vectors for constructing a plant expression vector include, but are not limited to pBI-type vectors or pPZP-type vectors. Additionally, examples of vectors and methods of making the same are described in the Examples below.

A plant expression vector may be introduced into a plant cell by using methods well known to those skilled in the art, for example, a method of infecting a plant cell with *Agrobacterium* or a method of directly introducing a vector into a cell. The method using *Agrobacterium* may be performed, for example, as described in Nagel et al. (1990) Microbiol. Lett., 67:325. According to this method, *Agrobacterium* is first transformed with a plant expression vector by, for example, electroporation, and then the transformed *Agrobacterium* is infected to a plant cell by a well-known method such as a leaf-disk method. Examples of the methods for directly introducing a plant expression vector into a cell include, but are not limited to, an electroporation method, a particle gun method, a calcium phosphate method, and a polyethylene glycol method. These methods are well known in the art and a method suitable for a particular plant to be transformed may be suitably selected by those skilled in the art.

The cells in which plant expression vectors have been introduced are selected, for example, based on their drug resistance such as resistance to kanamycin. Thereafter, the cells may be regenerated to a plant body by using a conventional method.

Methods to Decrease the Size of Plants

As provided above, the methods of the present invention can be used to alter plants such that the amount of OBP3 is increased, thus producing plants that are dwarfed in size. To obtain a plant that has an increased amount of OBP3 when compared to a non-altered plant, molecular techniques are used to increase the amount of OBP3 present in the altered plant.

Accordingly, in one embodiment, the method of altering the size and stature of a plant comprises over-expressing the polypeptide encoding OBP3, wherein said over expression of the polypeptide results in the reduced size of the aerial portion of the plant compared to a wild type plant. In another embodiment, the method of altering the size and stature of a plant comprises over-expressing the polypeptide encoding OBP3, wherein said over expression of the polypeptide results in the reduced size of the aerial portion of the plant compared to a wild type plant without dwarfing or significantly altering the root growth.

Accordingly, in one embodiment, the amount of OBP3 polypeptide expressed in the plant is from about 2 to than about 100 times greater than the amount of OBP3 polypeptide expressed in a wild type plant. In another embodiment, the amount of OBP3 polypeptide expressed in the plant is from about 2 to about 75 times greater than the amount of OBP3 polypeptide expressed in a wild type plant. In another embodiment, the amount of OBP3 polypeptide expressed in the plant is from about 2 to about 50 times greater than the amount of OBP3 polypeptide expressed in a wild type plant. In another embodiment, the amount of OBP3 polypeptide expressed in the plant is from about 2 to about 25 times greater than the amount of OBP3 polypeptide expressed in a wild type plant. In another embodiment, the amount of OBP3 polypeptide expressed in the plant is from about 2 to about 15 times greater than the amount of OBP3 polypeptide expressed in a wild type plant. In another embodiment, the amount of OBP3 polypeptide expressed in the plant is from about 5 to about 10 times greater than the amount of OBP3 polypeptide expressed in a wild type plant. In another embodiment, the amount of OBP3 polypeptide expressed in the plant is from about 2 to about 5 times greater than the amount of OBP3 polypeptide expressed in a wild type plant. In another embodiment, the amount of OBP3 polypeptide expressed in the plant is from about 2 times to about 10 times greater than the amount of OBP3 polypeptide expressed in a wild type plant.

In another embodiment of the invention, the method for altering the size of the aerial portion of a plant without dwarfing root tissue, said method comprises: (a) introducing a nucleic acid vector encoding *Arabidopsis thaliana* OBP3 into a plant cell; (b) regenerating the plant cell into a transgenic plant. Transgenic plants can be easily identified by evaluating the change in size by comparing the whole plant obtained by introducing the nucleic acid molecule with the size of a corresponding wild-type plant. In another embodiment, the altered size of the aerial portion of the plant comprises a decrease in the size of the aerial portion of the resulting plant.

In a specific embodiment of the invention, a method for producing a transgenic plant or plant part having altered size of the aerial portion of the plant without dwarfing root tissue as compared to the corresponding wild-type plant, said method comprises: (a) transforming plant cells by introducing a nucleic acid sequence encoding an OBP3 polypeptide, said nucleic acid sequence selected from the group consisting of: (i) the nucleotide sequence shown in SEQ ID NO:1, or the complement thereof; (ii) a nucleotide sequence that hybridizes to said nucleotide sequence of (i) under a wash stringency equivalent to 0.1×SSC to 2.0×SSC, 0.1% SDS, at 50-65° C., and which encodes a polypeptide having activity differing from that of *Arabidopsis thaliana* OBP3 by about 40% or less; (iii) a nucleotide sequence encoding the same amino acid sequence as said nucleotide sequence of (i), but which is degenerate in accordance with the degeneracy of the genetic code; and (iv) a nucleotide sequence encoding the same amino acid sequence as said nucleotide sequence of (ii), but which is degenerate in accordance with the degeneracy of the genetic code; (b) producing plants from said transformed plant cells. In another embodiment, the nucleotide sequence of (ii) encodes a polypeptide having activity differing from that of *Arabidopsis thaliana* OBP3 by about 30% or less. In another embodiment, the nucleotide sequence of (ii) encodes a polypeptide having activity differing from that of *Arabidopsis thaliana* OBP3 by about 20% or less. In another embodiment, the nucleotide sequence of (ii) encodes a polypeptide having activity differing from that of *Arabidopsis thaliana* OBP3 by about 10% or less. In another embodiment of the invention, the nucleic acid sequence is contained in a nucleic acid containing vector. In another embodiment, the altered size of the aerial portion of the plant comprises a decrease in the size of the aerial portion of the resulting plant.

Another embodiment of the invention is a resulting transgenic plant or plant part produced according to the methods disclosed herein. Another embodiment of the invention is a plant or agricultural product produced by the resulting plants or plant cells of the methods disclosed herein. Accordingly, in one embodiment of the invention, the plant product is a seed, a leaf, a fruit, or a flower produced by the resulting plants or plant parts of the methods disclosed herein.

As used herein, a plant is said to have an increased amount of OBP3 when the plant has more OBP3 than the non-altered plant. The present methods are therefore accomplished by targeting the levels of OBP3 in a plant.

What is contemplated is a reduction sufficient and effective to alter the size of a plant in a manner useful for the purposes outlined herein. Thus any alteration in the amount of OBP3, so long as it results in altered size of a plant, is contemplated by the present invention. Preferably, the alteration in the amount of the OBP3 is an increase in the amount of OBP3 expressed sufficient enough to result in a decrease in the size of the plant without dwarfing the roots.

In the preferred embodiment, the method of the present invention will result in plants at least 50% smaller than the standard size of a plant when compared to non-altered plants.

A variety of targets, strategies and molecular techniques can be used by a skilled artisan to increase the amount of OBP3 present in a plant. For example, to obtain a an increase in the amount of OBP3, molecular techniques can be used to increase the level of expression or activate the gene encoding one or more OBPs that are normally produced in the plant. The OBP3 can be altered in a variety of ways by a skilled artisan so as to obtain an alteration in the size of a plant.

Methods to Increase the Size of Plants

The methods of the present invention can be used to alter plants such that the levels of OBP3 are decreased, thus producing plants that are larger than wild-type plants. To obtain a plant that has larger than normal phenotype when compared to a non-altered plant, molecular techniques are used to decrease the amount of OBP3 present in the altered plant. As used herein, a plant is said to have a reduced or decreased amount of OBP3 when the plant has less OBP3 than the non-altered plant.

In another embodiment, the method of altering the size and stature of a plant comprises under-expressing, for example by repressing or knocking out, expression of the polypeptide encoding OBP3, such as by use of antisense nucleotides or RNAi, wherein said under-expression of the polypeptide results in increased aerial growth of the plant compared to a wild type plant. In another embodiment, the method of altering the size and stature of a plant comprises under-expressing, for example by repressing or knocking out, expression of the polypeptide encoding OBP3, such as by use of antisense nucleotides or RNAi, wherein said under expression of the polypeptide results in increased aerial growth of the plant compared to a wild type plant without altering the root growth. Repression of polypeptide expression includes not only the complete lack of polypeptide expression, but also any reduction in polypeptide expression sufficient to affect aerial growth of the plant.

Accordingly, in one embodiment of the invention, the amount of OBP3 polypeptide expressed in the plant is from about 2 to about 100 times less than the amount of OBP3 polypeptide expressed in a wild type plant. In another embodiment, the amount of OBP3 polypeptide expressed in the plant is from about 2 to about 75 times less than the amount of OBP3 polypeptide expressed in a wild type plant. In another embodiment, the amount of OBP3 polypeptide expressed in the plant is from about 2 to about 50 times less than the amount of OBP3 polypeptide expressed in a wild type plant. In another embodiment, the amount of OBP3 polypeptide expressed in the plant is from about 2 to about 25 times less than the amount of OBP3 polypeptide expressed in a wild type plant amount of OBP3 polypeptide expressed in the plant is from about 2 to about 15 times less than the amount of OBP3 polypeptide expressed in a wild type plant. In another embodiment, the amount of OBP3 polypeptide expressed in the plant is from about 5 to about 10 times less than the amount of OBP3 polypeptide expressed in a wild type plant. In another embodiment, the amount of OBP3 polypeptide expressed in the plant is from about 2 to about 5 times less than the amount of OBP3 polypeptide expressed in a wild type plant. In another embodiment, the amount of OBP3 polypeptide expressed in the plant is from about 2 times to about 10 times less than the amount of OBP3 polypeptide expressed in a wild type plant.

In a specific embodiment of the invention, a method for producing a transgenic plant or plant part having altered size of the aerial portion of the plant without dwarfing root tissue as compared to the corresponding wild-type plant, said method comprises: (a) transforming plant cells by introducing a antisense coding nucleic acid sequence complementary to a nucleic acid sequence encoding an OBP3 polypeptide, said nucleic acid sequence selected from the group consisting of: (i) the nucleotide sequence complementary to the nucleotide sequence shown in SEQ ID NO:1; (ii) a nucleotide sequence that hybridizes to said nucleotide sequence of (i) under a wash stringency equivalent to 0.1×SSC to 2.0× SSC, 0.1% SDS, at 50-65° C., and which encodes a polypeptide repressing activity of *Arabidopsis thaliana* OBP3 by about 60% or more; (iii) a nucleotide sequence encoding the same amino acid sequence as said nucleotide sequence of (i), but which is degenerate in accordance with the degeneracy of the genetic code; and (iv) a nucleotide sequence encoding the same amino acid sequence as said nucleotide sequence of (ii), but which is degenerate in accordance with the degeneracy of the genetic code; (b) producing plants from said transformed plant cells. In another embodiment, the antisense encoding nucleic acid sequence complementary to the nucleic acid sequence encoding an OBP3 encodes a polypeptide repressing activity of *Arabidopsis thaliana* OBP3 by about 70% or more. In another embodiment, the antisense encoding nucleic acid sequence complementary to the nucleic acid sequence encoding an OBP3 encodes a polypeptide repressing activity of *Arabidopsis thaliana* OBP3 by about 90% or more. In another embodiment, the antisense encoding nucleic acid sequence complementary to the nucleic acid sequence encoding an OBP3 encodes a polypeptide repressing activity of *Arabidopsis thaliana* OBP3 by about 95% or more. In another embodiment of the invention, the antisense encoding nucleic acid sequence complementary to the nucleic acid sequence encoding an OBP3 polypeptide is contained in a nucleic acid containing vector. In another embodiment, the altered size of the aerial portion of the plant comprises an increase in the size of the aerial portion of the resulting plant.

Another embodiment of the invention is a resulting transgenic plant or plant part produced according to the methods disclosed herein. Another embodiment of the invention is a plant or agricultural product produced by the resulting plants or plant cells of the methods disclosed herein. Accordingly, in one embodiment of the invention, the plant product is a seed, a leaf, a fruit, or a flower produced by the resulting plants or plant parts of the methods disclosed herein.

In the preferred embodiment, the method of the present invention will result in plants having a significant increase in size when compared to non-altered plants. In the Examples that follow, plants having a decrease in OBP3 were obtained.

Inactivation of OBP3

Another approach to inactivate one or more endogenous DNA plant genes that encode OBP3 employs homologous recombination to disrupt the gene. The techniques for recombinational inactivation are known in the art and can readily be adapted to the present invention, for example see D. K. Asch, et al. (1990) Mol. Gen. Genet. 221:37-43; K. K. Asch, et al. (1992) Genetics 130:737-748.

Transformation of Plant Cells

When an appropriate vector is obtained, for example as described above, transgenic plants are prepared which contain the desired expression unit or into which a recombination inactivation vector has been introduced. Transgenic plant cells may also be prepared in the same manner. A plant expression vector may be introduced into a plant cell by using methods well known to those skilled in the art. See, for example, Methods of Enzymology, Vol. 153, 1987, Wu and Grossman, Eds., Academic Press, incorporated herein by reference, and as disclosed in the Examples below that illustrate the invention.

Nucleic acid sequences can be directly introduced into a plant cell by contacting the plant cell using mechanical or chemical means. In one method of transformation, the vector is microinjected directly into plant cells by use of micropipettes to mechanically transfer the recombinant DNA into the plant cell (Crossway. (1985) Mol. Gen. Genetics 202: 179-185). In another method, the genetic material is transferred into the plant cell using polyethylene glycol (Krens, et al. (1982) Nature 296:72-74), or high velocity ballistic penetration by small particles with the nucleic acid either within the matrix of small beads or particles, or on the surface, is used (Klein, et al. (1987) Nature 327:70-73). In still another method protoplasts are fused with other entities which contain the DNA whose introduction is desired. These entities are minicells, cells, lysosomes or other fusible lipid-surfaced bodies (Fraley, et al. (1982) *Proc. Natl. Acad. Sci. USA,* 79:1859-1863).

Another method involves the transfer of exogenous bacteriophage or plasmid DNA into germinating pollen grains to modify plant properties. As the pollen tube emerges from the mature pollen grain, cell wall material is deposited behind the growing tip. Another method, known as direct transformation, induces uptake and integration of plasmid or linearized DNA in the genome of plant protoplasts, i.e., single cells stripped of cell wall material (Lorz et al., Mol. Genet. 199:178-182, 1985).

DNA may also be introduced into the plant cells by electroporation (From et al. (1985) Proc. Natl. Acad. Sci. USA 82:5824). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Selection of the transformed plant cells with the transformed gene can be accomplished using phenotypic markers as described herein.

For transformation mediated by bacterial infection, a plant cell is infected with *Agrobacterium tumefaciens* or *A. rhizogenes* previously transformed with the DNA to be introduced. *Agrobacterium* is a representative genus of the gram-negative family *Rhizobiaceae*. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

A method using *Agrobacterium* inserts sequences of a plasmid, known as the Ti-plasmid, into the genome of plant cells (Chilton et al., *Cell* (1977) 11:263:271). A heterologous nucleic acid sequence can be introduced into a plant cell utilizing *Agrobacterium tumefaciens* containing the Ti plasmid. In using an *A. tumefaciens* culture as a transformation vehicle, it is most advantageous to use a non-oncogenic strain of the *Agrobacterium* as the vector carrier so that normal non-oncogenic differentiation of the transformed tissues is possible. It is also preferred that the *Agrobacterium* harbor a binary Ti plasmid system. Such a binary system comprises 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, Biotechnology, 1:262, 1983; Hoekema, et al., Nature, 303:179, 1983). Such a binary system is preferred because it does not require integration into Ti plasmid in *Agrobacterium*. A method using *Agrobacterium* may be performed, for example, as described in Nagel et al. Microbiol. Lett., (1990) 67:325. According to this method, *Agrobacterium* is first transformed with a plant expression vector by, for example, electroporation, and then the transformed *Agrobacterium* is infected to a plant cell by a well-known method, such as for example, a leaf-disk method. Methods involving the use of *Agrobacterium* include, but are not limited to: 1) co-cultivation of *Agrobacterium* with cultured isolated protoplasts; 2) transformation of plant cells or tissues with *Agrobacterium*; or 3) transformation of seeds, apices or meristems with *Agrobacterium*.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome (J. Schell. (1987) Science 237:1176-1183). Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid (Hoekema, et al. (1983) Nature 303:179-189). The transferred DNA region can be increased in size by the insertion-of heterologous DNA without its ability to be transferred being affected. Thus a modified Ti or Ri plasmid, in which the disease-causing genes have been deleted, can be used as a vector for the transfer of the gene constructs of this invention into an appropriate plant cell.

Construction of recombinant Ti and RI plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors," (Ruvkum and Ausubel. (1981) Nature 298:85-88), promoters (Lawton, et al. (1987) Plant Mol. Biol. 9:315-324) and structural genes for antibiotic resistance as a selection factor (Fraley, et al. (1983) Proc. Natl. Acad. Sci. USA 80:4803-4807).

There are two classes of recombinant Ti and Ri plasmid vector systems now in use. In one class, called "co-integrate," the shuttle vector containing the gene of interest is inserted by genetic recombination into a non-oncogenic Ti plasmid that contains both the cis-acting and trans-acting elements required for plant transformation as, for example, in the pMLJ1 shuttle vector of DeBlock, et al. (1984) EMBO J 3:1681-1689 and the non-oncogenic Ti plasmid pGV3850, described by Zambryski, et al. (1983) EMBO J 2:2143-2150. In the second class or "binary" system, the gene of interest is inserted into a shuttle vector containing the cis-acting elements required for plant transformation. The other necessary functions are provided in trans by the non-oncogenic Ti plasmid, as exemplified by the pBIN19 shuttle vector described by Bevan ((1984) Nucleic Acids Res. 12:8711-8721) and the non-oncogenic Ti plasmid pAL4404 described by Hoekma, et al., (1983). Some of these vectors are commercially available.

There are two common ways to transform plant cells with *Agrobacterium*: co-cultivation of *Agrobacterium* with cultured isolated protoplasts, or transformation of intact cells or tissues with *Agrobacterium*. The first requires an established culture system that allows for culturing protoplasts and subsequent plant regeneration from cultured protoplasts. The second method requires (a) that the intact plant tissues, such as cotyledons, can be transformed by *Agrobacterium* and (b) that the transformed cells or tissues can be induced to regenerate into whole plants.

Most dicot species can be transformed by *Agrobacterium* as all species which are a natural plant host for *Agrobacterium* are transformable in vitro. Monocotyledonous plants, and in particular, cereals, are not natural hosts to *Agrobacterium*. Attempts to transform them using *Agrobacterium* have been unsuccessful until recently (Hooykas-Van Slogteren, et al. (1984) Nature 311:763-764). However, there is growing evidence now that certain monocots can be transformed by *Agrobacterium*. Using novel experimental approaches cereal species such as rye (de la Pena, et al. (1987) Nature 325:274-276), maize (Rhodes, et al. (1988) Science 240:204-207), and rice (Shimamoto, et al. (1989) Nature 338:274-276) may now be transformed.

In addition, gene transfer can be accomplished by in situ transformation by *Agrobacterium*, as described in Bechtold, et al., *C.R. Acad. Sci. Paris* (1993) 316:194. This approach is based upon the vacuum infiltration of a suspension of *Agrobacterium* cells.

In addition to the methods disclosed above, specific methods for transforming a wide variety of dicots and obtaining transgenic plants are well documented in the literature (Gasser and Fraley, 1989; Fisk and Dandekar, 1993; Christou, 1994; and the references cited therein).

Successful transformation and plant regeneration have been achieved in the monocots as follows: asparagus (*Asparagus officinalis*; Bytebier et al. 1987); barley (*Hordeum vulgarae*; Wan and Lemaux 1994); maize (*Zea mays*; Rhodes et al., 1988; Gordon-Kamm et al., 1990; Fromm et al., 1990; Koziel et al., 1993); oats (*Avena sativa*; Somers et al., 1992); orchard grass (*Dactylis glomerata*; Horn et al., 1988); rice (*Oryza sativa*, including *indica* and *japonica* varieties; Toriyama et al., 1988; Zhang et al., 1988; Luo and Wu 1988; Zhang and Wu 1988; Christou et al., 1991); rye (*Secale cereale*; De la Pena et al., 1987); sorghum (*Sorghum bicolor*, Cassas et al. 1993); sugar cane (*Saccharum* spp.; Bower and Birch 1992); tall fescue (*Festuca arundinacea*; Wang et al. 1992); turfgrass (*Agrostis palustris*; Zhong et al., 1993); and wheat (*Triticum aestivum*; Vasil et al. 1992; Weeks et al. 1993; Becker et al. 1994).

Identification of transformed cells or plants is generally accomplished by including a selectable marker in the transforming vector, or by obtaining evidence of successful bacterial infection.

Accordingly, one embodiment is a transgenic plant cell transformed by a nucleic acid sequence encoding an OBP3 polypeptide, wherein expression of said polypeptide in the plant cell results in an alteration in the size of the resulting aerial portion of a plant generated from the cell without dwarfing root tissue as compared to a corresponding wild-type variety of plant. In another embodiment, the nucleic acid sequence polypeptide is over-expressed resulting in a decrease in the size of the resulting aerial portion of a plant generated from the cell without dwarfing the root tissue as compared to a wild type variety plant. In yet another embodiment, the nucleic acid sequence encoding the polypeptide is selected from the group consisting of: (a) the nucleotide sequence shown in SEQ ID NO:1, or the complement thereof; (b) a nucleotide sequence that hybridizes to said nucleotide sequence of (a) under a wash stringency equivalent to 0.1×SSC to 2.0×SSC, 0.1% SDS, at 50-65° C., and which encodes a polypeptide having activity differing from that of *Arabidopsis thaliana* OBP3 by about 40% or less; (c) a nucleotide sequence encoding the same amino acid sequence as said nucleotide sequence of (a), but which is degenerate in accordance with the degeneracy of the genetic code; and (d) a nucleotide sequence encoding the same amino acid sequence as said nucleotide sequence of (b), but which is degenerate in accordance with the degeneracy of the genetic code. In another embodiment, the nucleotide sequence in (b) encodes a polypeptide having activity differing from that of *Arabidopsis thaliana* OBP3 by about 30% or less. In another embodiment, the nucleotide sequence in (b) encodes a polypeptide having activity differing from that of *Arabidopsis thaliana* OBP3 by about 20% or less. In another embodiment, the nucleotide sequence in (b) encodes a polypeptide having activity differing from that of *Arabidopsis thaliana* OBP3 by about 10% or less.

A transgenic plant cell may also be used to cause a plant cell or plant to under-express a nucleic acid or polypeptide of interest, for example by repressing or knocking out the same. Methods of using antisense and RNAi technology are described below.

Accordingly, another embodiment of the invention is a transgenic plant cell transformed by an antisense nucleic acid sequence complementary to a nucleic acid sequence encoding an OBP3 polypeptide, wherein said antisense nucleic acid sequence results in an increase in the size of a resulting plant as compared to a corresponding wild-type variety of plant. In another embodiment, the antisense nucleic acid sequence is complementary to a nucleic acid sequence encoding an *Arabidopsis thaliana* OBP3 and homologs, analogs, orthologs, and paralogs thereof.

In a preferred embodiment, the nucleic acid sequence encoding the polypeptide is selected from the group consisting of: (a) the nucleotide sequence shown in SEQ ID NO:1, or the complement thereof; (b) a nucleotide sequence that hybridizes to said nucleotide sequence of (a) under a wash stringency equivalent to 0.1×SSC to 2.0×SSC, 0.1% SDS, at 50-65° C., and which encodes a polypeptide having activity differing from that of *Arabidopsis thaliana* OBP3 by about 40% or less; (c) a nucleotide sequence encoding the same amino acid sequence as said nucleotide sequence of (a), but which is degenerate in accordance with the degeneracy of the genetic code; and (d) a nucleotide sequence encoding the same amino acid sequence as said nucleotide sequence of (b), but which is degenerate in accordance with the degeneracy of the genetic code. In another embodiment, the nucleotide sequence in (b) encodes a polypeptide having activity differing from that of *Arabidopsis thaliana* OBP3 by about 30% or less. In another embodiment, the nucleotide sequence in (b) encodes a polypeptide having activity differing from that of *Arabidopsis thaliana* OBP3 by about 20% or less. In another embodiment, the nucleotide sequence in (b) encodes a polypeptide having activity differing from that of *Arabidopsis thaliana* OBP3 by about 10% or less.

The invention also includes plants, plant parts, plant products, such as for example, seeds, flowers, leaves, or fruits, and agricultural products, comprising the transgenic plant cells described herein. Moreover, the invention also includes plants, plant parts, plant products, such as for example, seeds, flowers, leaves, or fruits, and agricultural products, produced by transgenic plants comprising the transgenic plant cells described herein.

Regeneration of Transformed Plants

Normally, a plant cell is regenerated to obtain a whole plant from the transformation process. The immediate product of the transformation is referred to as a "transgenote".

Regeneration from protoplasts varies from species to species of plants, but generally a suspension of protoplasts is first made. In certain species, embryo formation can then be induced from the protoplast suspension. The culture media will generally contain various amino acids and hormones, necessary for growth and regeneration. Examples of hormones utilized include auxins and cytokinins. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see Methods in Enzymology, Vol. 118 and Klee et al. (1987) Ann Rev Plant Physiol 38:467). Utilizing the leaf disk-transformation-regeneration method of Horsch et al. (Horsch et al. (1985) Science 227:1229), disks are cultured on selective media, followed by shoot formation in about 24 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, mature transgenic plants can be self crossed to produce a homozygous inbred plant. The resulting inbred plant produces seed containing the newly introduced foreign gene(s). These seeds can be grown to produce plants that would produce the selected phenotype, e.g. increased yield. Additional desired phenotypes include increased growth density, and decreased size of the resulting aerial portion of the plant without dwarfing root tissue as compared to a corresponding wild-type variety of plant.

Parts obtained from regenerated plant, such as flowers, seeds, leaves, branches, roots, fruit, and the like are included in the invention, provided that these parts comprise plant cells that have been transformed as described. Progeny and variants, and mutants of the regenerated plants are also included within the scope of the invention, provided that these parts comprise the introduced nucleic acid sequences.

Plants exhibiting increased growth and/or yield as compared with wild-type plants can be selected by visual observation. The invention includes plants produced by the method of the invention, as well as plant tissue and seeds.

Expression of the introduced gene of the present invention in the regenerated plant body can be confirmed by using a procedure well known to those skilled in the art. This confirmation can be performed by northern blot analysis, for example. More specifically, the total RNAs may be extracted from leaves of a resultant plant, and may be subjected to denatured agarose gel electrophoresis, and then, RNAs may be blotted onto an appropriate membrane. The blot can be hybridized with a labeled RNA probe complementary to a part of the introduced gene to detect mRNA from the gene of the present invention.

The plant of the present invention is a transgenic plant produced by the above-mentioned procedure. It is preferable that the altered characteristics of the transgenic plant (i.e., morphology of a flower, coloring of a flower, a size of a plant, and/or the number of branches) include that which is not found in a known wild-type or horticultural type. It is also preferable that the altered characteristics of a plant are horticulturally valuable. Furthermore, it is preferable that altered characteristics of a flower are stably conserved over subsequent generations.

Accordingly, the present invention includes transgenic plants comprising any of the transgenic plant cells or vectors described herein, including plants generated from the transgenic plant cells or transgenic plants, or by any methods described herein.

Antisense Nucleic Acids

In addition to the nucleic acid molecules encoding the OBP3 described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire OBP3 coding strand, or to only a portion thereof. In one embodiment, an antisense nucleic acid molecule is antisense to a "coding region" of the coding strand of a nucleotide sequence encoding OBP3. The term "coding region" refers to the region of the nucleotide sequence comprising codons that are translated into amino acid residues (e.g., the entire coding region of, , , comprises nucleotides 1 to . . . ). In another embodiment, the antisense nucleic acid molecule is antisense to a "noncoding region" of the coding strand of a nucleotide sequence encoding OBP3. The term "noncoding region" refers to 5' and 3' sequences that flank the coding region that are not translated into amino acids (i.e., also referred to as 5' and 3' untranslated regions). In another embodiment, the antisense nucleic acid molecule is antisense to a "coding region" contiguous with a "noncoding region" of the coding strand of a nucleotide sequence encoding OBP3.

Given the coding strand sequences encoding the OBP3 disclosed herein (e.g., the sequence set forth in SEQ ID NO:1) antisense nucleic acids of the invention can be designed according to the rules of Watson and Crick base pairing. The antisense nucleic acid molecule can be complementary to the entire coding region of OBP3 mRNA, but more preferably is an oligonucleotide which is antisense to only a portion of the coding or noncoding region of OBP3 mRNA. For example, the antisense oligonucleotide can be complementary to the region surrounding the translation start site of OBP3 mRNA. An antisense oligonucleotide can be, for example, about 5, 10, 15, 20, 25, 30, 35, 40, 45 or 50 nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosylqueosine, 5'-methoxycarboxymethyluracil, 5-methoxyuracil, 2-methylthio-N6-isopenten- yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding OBP3 to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

The invention further provides a recombinant expression vector comprising an OBP3 DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to an OBP3 mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus wherein antisense nucleic acids are produced under the control of a high efficiency regulatory region. The activity of the regulatory region can be determined by the cell type into which the vector is introduced. For a discussion of the regulation of gene expression using antisense genes see Weintraub, H. et al. (1986) Trends Gen 1 and Mol et al. (1990) FEBS Lett 268:427-430. Methods for inhibiting expression in plants using antisense constructs, including generation of antisense sequences in situ are described, for example, in U.S. Pat. Nos. 5,107,065 and 5,254,800.

Accordingly, in one embodiment, the invention is a recombinant antisense expression vector comprising: (a) a promoter, said promoter being functional in a plant cell; and (b) an antisense coding nucleic acid sequence complementary to a nucleic acid sequence encoding an OPB3 polypeptide, wherein said antisense nucleic acid sequence is operably linked to said promoter and is oriented with respect to said promoter such that RNA produced by said antisense coding nucleic acid sequence is complementary to and capable of hybridizing in a stringent manner to mRNA encoding OPB3, wherein said OBP3 antisense coding nucleic acid comprises a nucleotide sequence of at least 15 contiguous nucleotides complementary to SEQ ID NO:1. In another embodiment, the antisense coding nucleic acid sequence comprises a nucleotide sequence of at least 15 contiguous nucleotides complementary to SEQ ID NO:12. In another embodiment, the antisense coding nucleic acid sequence comprises a nucleotide sequence of at least 15 contiguous nucleotides complementary to SEQ ID NO:13. In another embodiment, the antisense coding nucleic acid sequence comprises a nucleotide sequence of at least 15 contiguous nucleotides complementary to SEQ ID NO:14. In another embodiment, the antisense coding nucleic acid sequence comprises a nucleotide sequence of at least 15 contiguous nucleotides complementary to SEQ ID NO:15. In another embodiment, the antisense coding nucleic acid sequence comprises a nucleotide sequence of at least 15 contiguous nucleotides complementary to SEQ ID NO:16. In another embodiment, the antisense coding nucleic acid sequence comprises a nucleotide sequence of at least 15 contiguous nucleotides complementary to SEQ ID NO:17. In another embodiment, the antisense coding nucleic acid sequence comprises a nucleotide sequence of at least 15 contiguous nucleotides complementary to SEQ ID NO:18. In another embodiment, the antisense coding nucleic acid sequence comprises a nucleotide sequence of at least 15 contiguous nucleotides complementary to SEQ ID NO:19. In another embodiment, the antisense coding nucleic acid sequence comprises a nucleotide sequence of at least 15 contiguous nucleotides complementary to SEQ ID NO:20. In still another embodiment, the said nucleic acid sequence encoding an OBP3 polypeptide is selected from the group consisting of: (a) the nucleotide sequence shown in SEQ ID NO:1, or the complement thereof; (b) a nucleotide sequence that hybridizes to said nucleotide sequence of (a) under a wash stringency equivalent to 0.1×SSC to 2.0×SSC, 0.1% SDS, at 50-65° C., and which encodes a polypeptide having activity differing from that of *Arabidopsis thaliana* OBP3 by about 40% or less; (c) a nucleotide sequence encoding the same amino acid sequence as said nucleotide sequence of (a), but which is degenerate in accordance with the degeneracy of the genetic code; and (d) a nucleotide sequence encoding the same amino acid sequence as said nucleotide sequence of (b), but which is degenerate in accordance with the degeneracy of the genetic code. In another embodiment of the invention, the nucleotide sequence of (b) encodes a polypeptide having activity differing from that of *Arabidopsis thaliana* OBP3 by about 30% or less. In another embodiment of the invention, the nucleotide sequence of (b) encodes a polypeptide having activity differing from that of *Arabidopsis thaliana* OBP3 by about 20% or less. In another embodiment of the invention, the nucleotide sequence of (b) encodes a polypeptide having activity differing from that of *Arabidopsis thaliana* OBP3 by about 10% or less.

Other methods that can be used to inhibit expression of an endogenous gene in a plant may also be used in the present methods. For example, formation of a triple helix at an essential region of a duplex gene serves this purpose. The triplex code, permitting design of the proper single stranded participant is also known in the art. (See H. E. Moser, et al. (1987) Science 238:645-650 and M. Cooney, et al. (1988) Science 241:456-459). Regions in the control sequences containing stretches of purine bases are particularly attractive targets. Triple helix formation along with photocrosslinking is described, e.g., in D. Praseuth, et al. (1988) Proc. Natl Acad. Sci. USA 85:1349-1353.

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes described in Haselhoff and Gerlach (1988) Nature 334:585-591) can be used to catalytically cleave GBSRP mRNA transcripts to thereby inhibit translation of GBSRP mRNA. A ribozyme having specificity for an OBP3-encoding nucleic acid can be designed based upon the nucleotide sequence of an OBP3 cDNA. For example, a derivative of a Tetrahymena L-19 IVS RNA can be constructed in which the nucleotide sequence of the active site is complementary to the nucleotide sequence to be cleaved in an OBP3-encoding mRNA. See, e.g., Cech et al. U.S. Pat. No. 4,987,071 and Cech et al. U.S. Pat. No. 5,116,742. Alternatively, OBP3 mRNA can be used to select a catalytic RNA having a specific ribonuclease activity from a pool of RNA molecules. See, e.g., Bartel, D. and Szostak, J. W. (1993) Science 261:1411-1418.

The invention also provides plant, plant tissue and seeds produced by the methods of the invention.

This invention will be better understood by reference to the following Examples, which are intended to merely illustrate the best mode now known for practicing the invention. The scope of the invention is not to be considered limited thereto, however.

EXAMPLE 1

Seedling Growth and Light Conditions

Seeds were sterilized by shaking in 70% EtOH with 0.05% Triton X-100 for 15 min. After a 15 min treatment in 95% EtOH, seeds were dried on sterile Whatman filter paper in a laminar-flow hood. Dry, sterile seeds were sprinkled on one-half-strength Murashige Minimal Organics Media with 1.5% sucrose (GibcoBRL). Phytagar (0.8%) was used as a gelling agent when kanamycin (30 mg/L) was included. Phytagel (1%) was used as a gelling agent for media without kanamycin. Four 17-W fluorescent bulbs (F17T8/TL711, Philips Lighting Company), and two 25-W frosted incandescent bulbs (BC25T10/IF, Philips Lighting Company) in an incubator (model E-30-B, Percival, Boone Iowa) supplied the white light. Light emitting diodes in an incubator (model E-30-LED, Percival, Boone Iowa) supplied blue and far-red lights. All seedlings were grown at 24° C. Digitized images of seedlings were measured as in Neff and Chory (1998) Plant Physiol 118:27-36.

EXAMPLE 2

Isolation of the sob1-D Mutation sob1-D phyB-4 mutant was isolated in an activation-tagging mutant screen for suppressors of the phyB-4 long hypocotyl phenotype (FIG. 1). Arabidopsis phyB-4 mutants were transformed with the activation tagging construct pSKI074 (Genbank accession number AF218466, Weigel, D. et al. (2000) Plant Physiol 122:1003-1013) essentially the same as in Neff, M. M. et al. (1999) Proc Natl Acad Sci USA 96:15316-15323. This construct contains a tandem array of four head-to-tail copies of enhancer elements from the CaMV 35S promoter (Weigel, D. et al. (2000) Plant Physiol 122:1003-1013). These elements are known to enhance the expression of nearby open-reading-frames (ORFs) after insertion into the Arabidopsis genome, causing a dominant, gain-of-function mutant phenotype.

Primary transformants, heterozygous for the transgene were selected for on growth media containing of kanamycin (Neff, M. M. et al. (1999) Proc Natl Acad Sci USA 96:15316-15323). The conditions (~50 µM/m2/sec of white light, 24° C.) were sufficient to identify those mutants that suppress the long hypocotyl phenotype of the phyB-4 mutant. To confirm genetic heritability of the mutant phenotype and to begin establishing linkage to the T-DNA transgene, T2 seeds from self-fertilized sob1-D phyB-4 plants were re-screened on two plates of growth media, one with and one without kanamycin. To confirm linkage of the dominant mutant phenotype with the T-DNA transgene and to identify individuals homozygous for the mutating transgene, T3 seeds from self-fertilized T2 plants were re-screened on two plates of growth media, one with and one without kanamycin.

EXAMPLE 3

Plasmid Rescue

Figure 2:
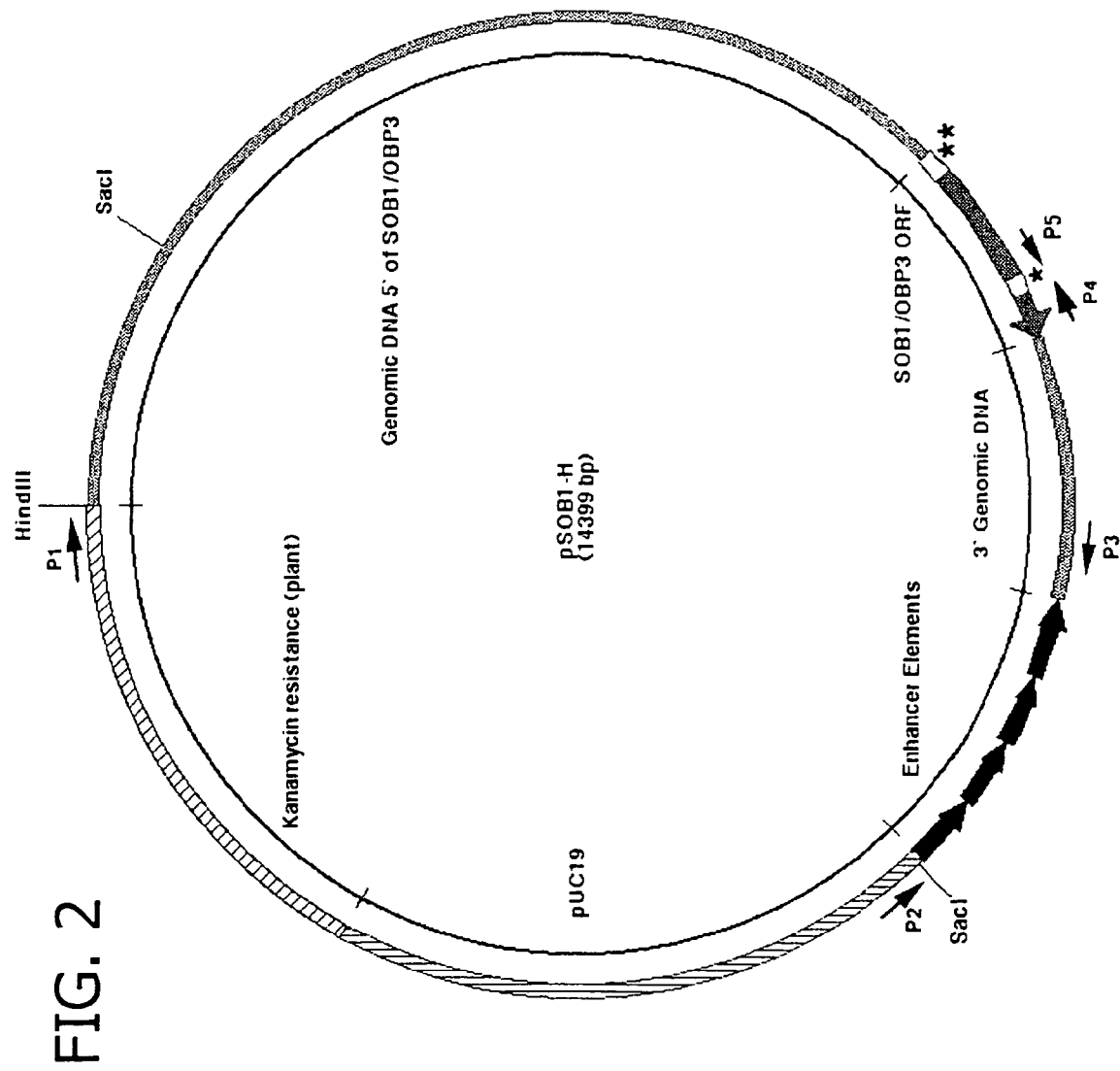
FIG. 2: The pSOB-H rescued plasmid contains the entire OBP3/SOB1 open reading frame (ORF).

Genomic DNA adjacent to the enhancer elements was cloned from homozygous sob1-D phyB-4 plants via plasmid rescue (FIG. 2). Southern analysis and plasmid rescue was performed essentially as in Neff, M. M. et al. (1999) Proc Natl Acad Sci USA 96:15316-15323. Plant genomic DNA was digested with the restriction endonuclease HindIII and re-ligated with T4 DNA ligase. To identify genomic DNA flanking the enhancer elements, the resulting 14.4 kb plasmid, pSOB1-H (SEQ ID NO:1), was sequenced with primer P1(SEQ ID NO:3)(5'-GCTCTCTCGAGGTCGACGG-3') near the HindIII site in the T-DNA. BLASTn analysis indicated that this rescued plasmid contained the entire SOB1/OBP3 ORF with the 3' end of the gene closest to the T-DNA enhancer elements. To confirm that the genomic DNA adjacent to the enhancers in the pSOB1-H plasmid is the same as the genomic DNA in the sob1-D phyB-4 mutant, primers P2 (SEQ ID NO:4)(5'-AATTATGCCGAATGTA-CATGC-3') and P3 (SEQ ID NO:5)(5'-TAATACGACT-CACTATAGGG-3') were used for PCR analysis. pSOB1-H includes approximately 1.2 kb of non-coding genomic DNA between the enhancer elements and the 3' end of the SOB1/OBP3 ORF. Approximately 5.3 kb of genomic DNA 5' of the ORF is also contained in this rescued plasmid.

EXAMPLE 4

RT-PCR Analysis of the OBP3 Gene

Figure 3:
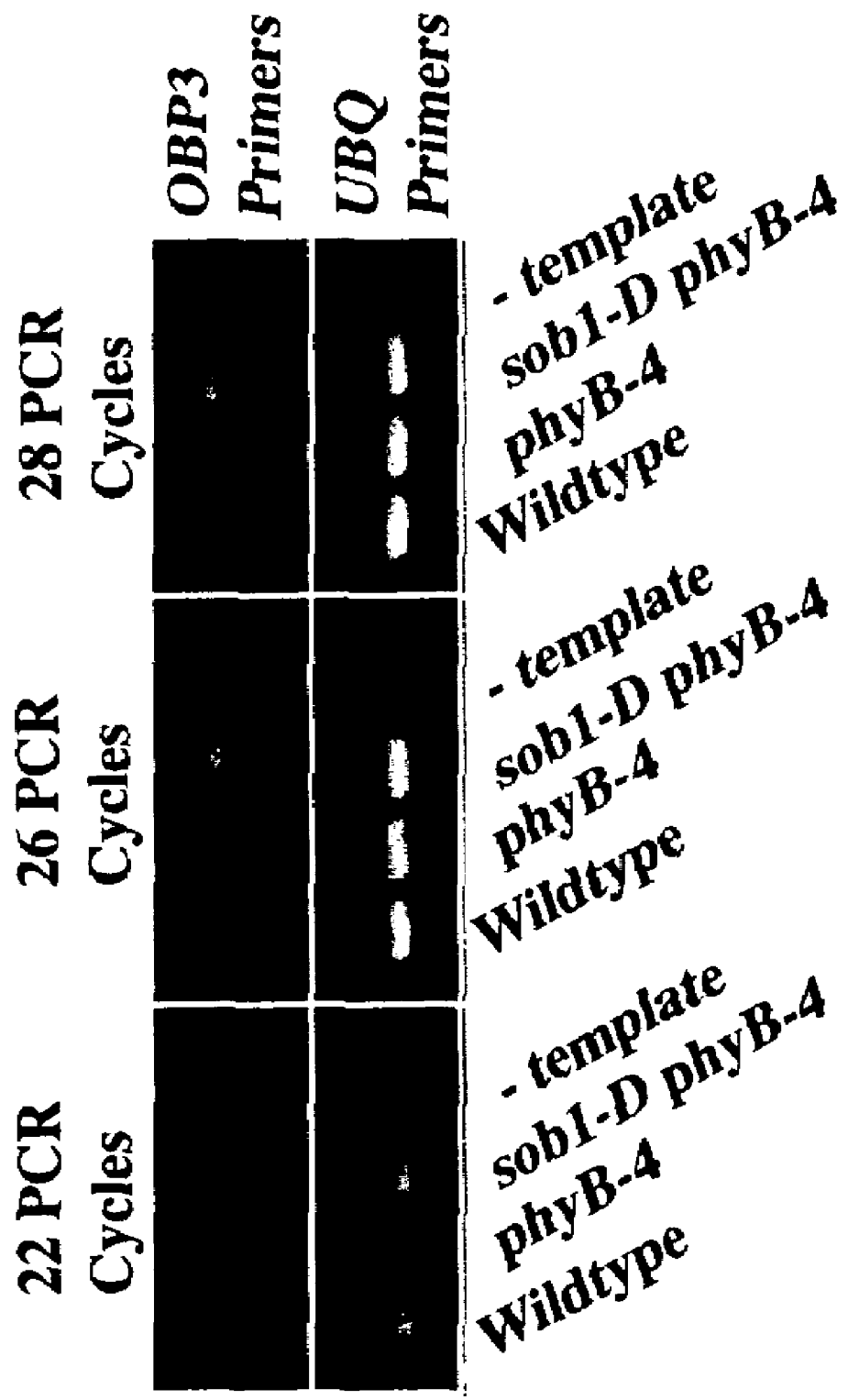
FIG. 3: OBP3 transcript is overexpressed in the sob1-D phyB-4 mutant.

RT-PCR analysis was performed essentially the same as in Neff, M. M. et al. (1999) Proc Natl Acad Sci USA 96:15316-15323 (See FIG. 3). UBQ10 primers were used as a template loading control, as in Neff, M. M. et al. (1999) Proc Natl Acad Sci USA 96:15316-15323. The OBP3-specific primers P4 (SEQ ID NO:6)(5'-CCATGATGTGTATCCCTCG-3') and P5 (SEQ ID NO:7)(5'-GTGGTATGAGTTCTAGTGG-3') flank the only predicted intron in the SOB1/OBP3 ORF. Total RNA was isolated from 7 day-old seedlings grown under the same conditions as the original mutant screen.

EXAMPLE 5

Cloning of the sob1-D Mutation

Figure 4:
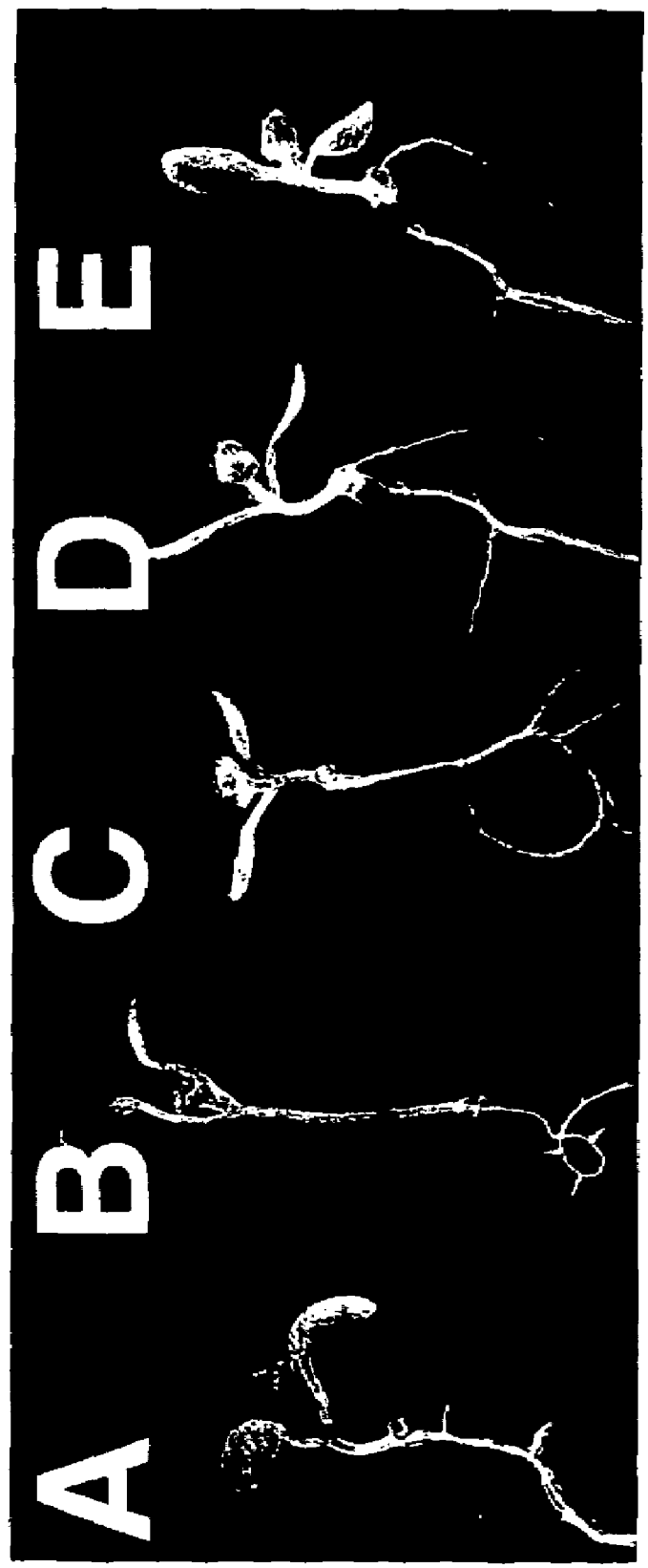
FIG. 4: The sob1-D phyB-4 seedling phenotype is caused by overexpression of OBP3.
Figure 5:
FIG. 5: The sob1-D mutation confers dwarfism in adult plants.
Figure 6:
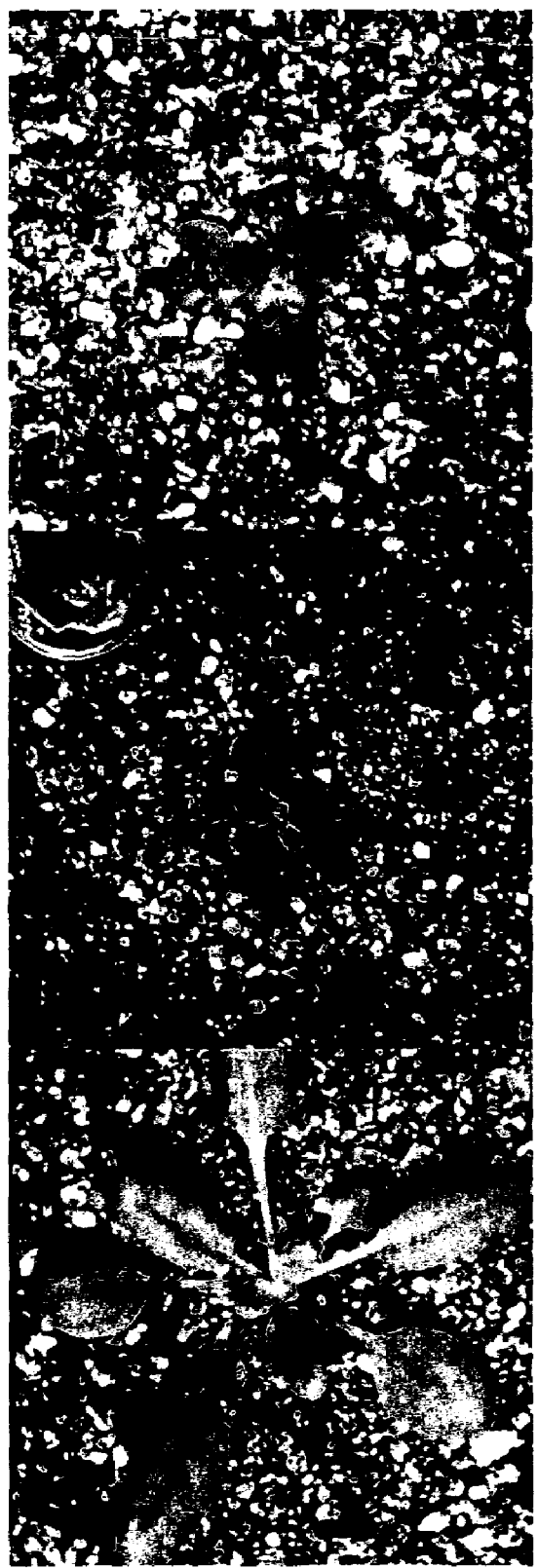
FIG. 6: The sob1-D phyB-4 adult phenotype is caused by overexpression of OBP3.

The sob1-D recapitulation construct, pCC2, was generated by ligating a SacI fragment from pSOB1-H into pPZP212 (Hajdukiewicz, P. et al. (1994) Plant Mol Biol 25:989-994) cut with SacI. The SacI fragment isolated from pCC2 contained all four copies of the CaMV 35S enhancer elements, the SOB1/OBP3 ORF and approximately 4.1 kb of non-coding DNA 5' of the SOB1/OBP3 ORF. Transgenic phyB-4 plants containing this transgene reproducibly recapitulate the sob1-D mutant phenotypes in both seedlings (FIG. 4) and adults (See FIGS. 5 and 6), demonstrating that the sob1-D/OBP3-OX mutation can be used to generate dwarf Arabidopsis.

EXAMPLE 6

Characterization of the sob1-D Mutation

As adults, the sob1-D mutation confers dosage-dependent dwarfism in the rosette with homozygous sob1-D/sob1-D lines being more severely dwarfed than heterozygous sob1-

D/SOB1 lines (FIG. 5), suggesting that the dosage of sob1-D/OBP3-OX expression can be used to fine-tune the degree of dwarfism in transgenic plants.

Figure 7:
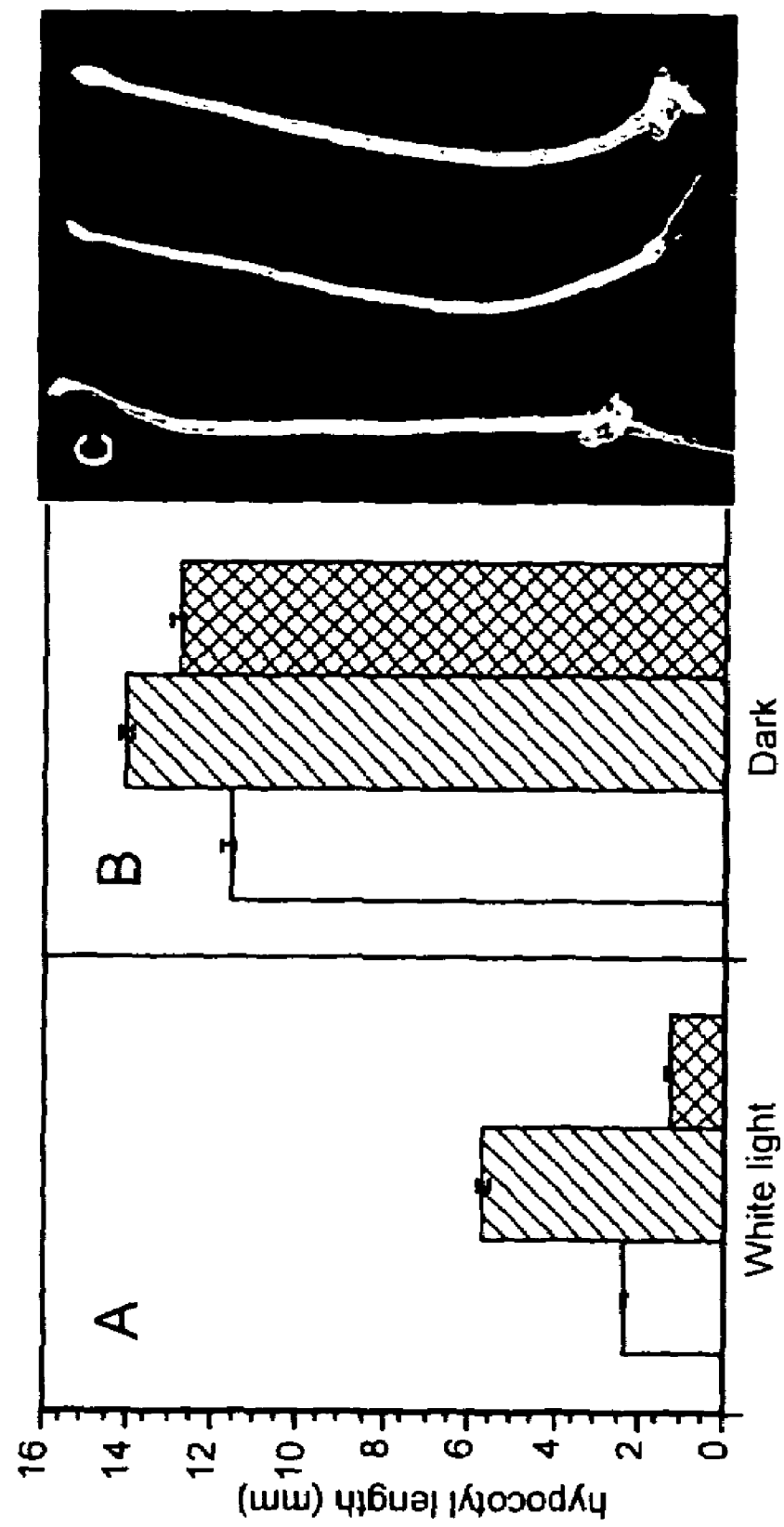
FIG. 7: sob1-D phyB-4 mutants have long hypocotyls when grown in the dark.

Clearly the sob1-D/OBP3-OX mutation confers dwarfism in adult plants. Dark-grown sob1-D phyB-4 hypocotyls elongate as well or better than the wild type and phyB-4 indicates that the dwarfing phenotype conferred by this dominant mutation is dependent upon light (FIG. 7).

Figure 8:
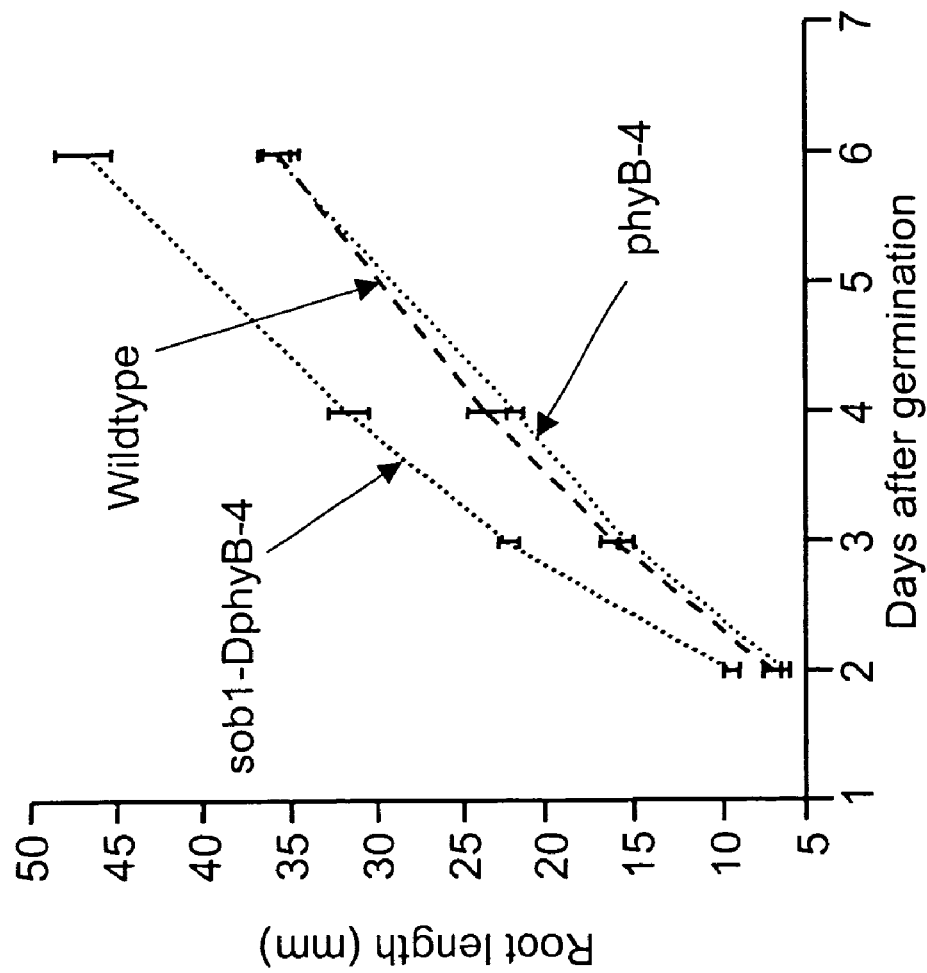
FIG. 8: sob1-D phyB-4 roots are longer than phyB-4 or the wild-type.

To test the possibility that all tissues are dwarfed by the sob1-D/OBP3-OX mutation; wildtype, phyB-4 and sob1-D phyB-4 plants were grown in white light on vertical agar plates and the roots were measured of a course of many days (FIG. 8). The roots of the sob1-D phyB-4 mutant grow more than the wild type or phyB-4, indicating that the sob1-D/OBP3-OX mutation does not confer dwarfism is all tissues. Thus, this mutation can be used to dwarf the stature of aerial tissue without dwarfing root tissue.

Figure 9:
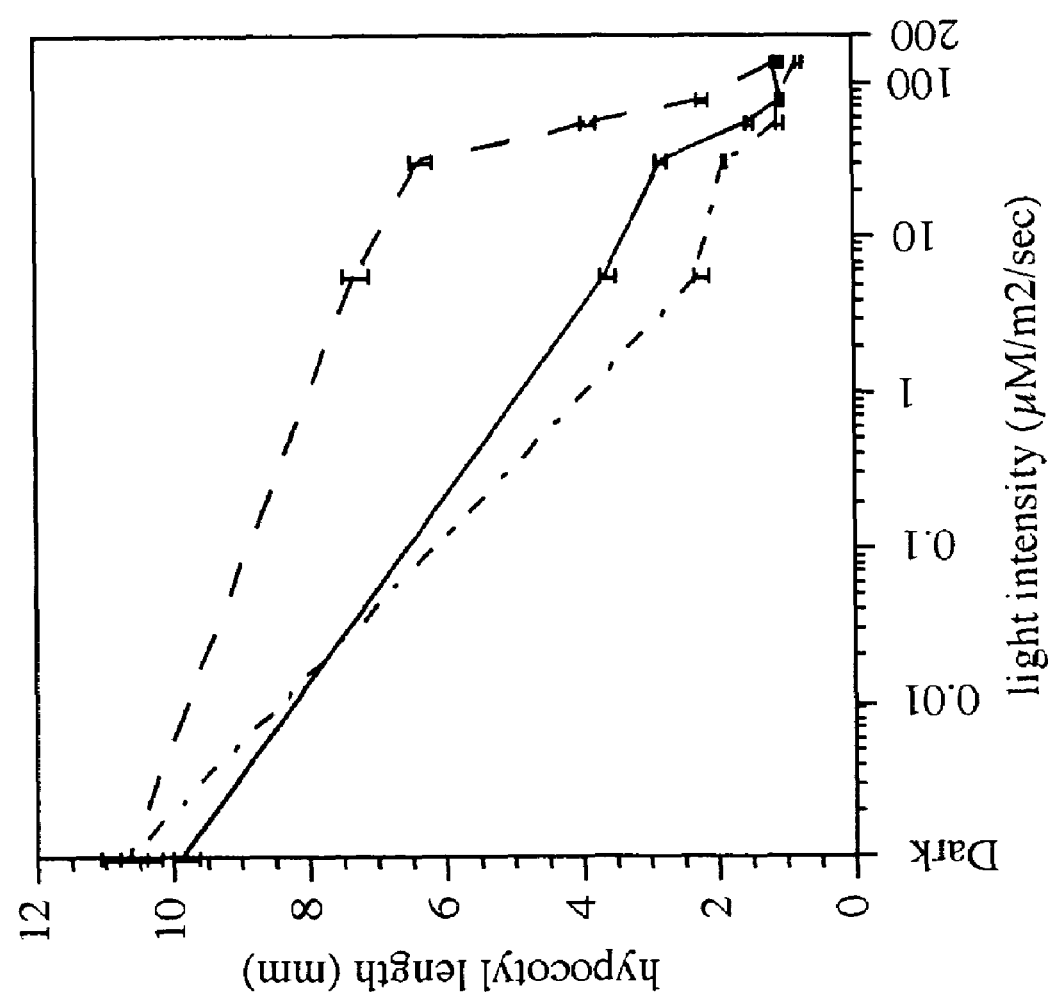
FIG. 9: sob1-D phyB4 hypocotyls are hyper-responsive to light.
Figure 10:
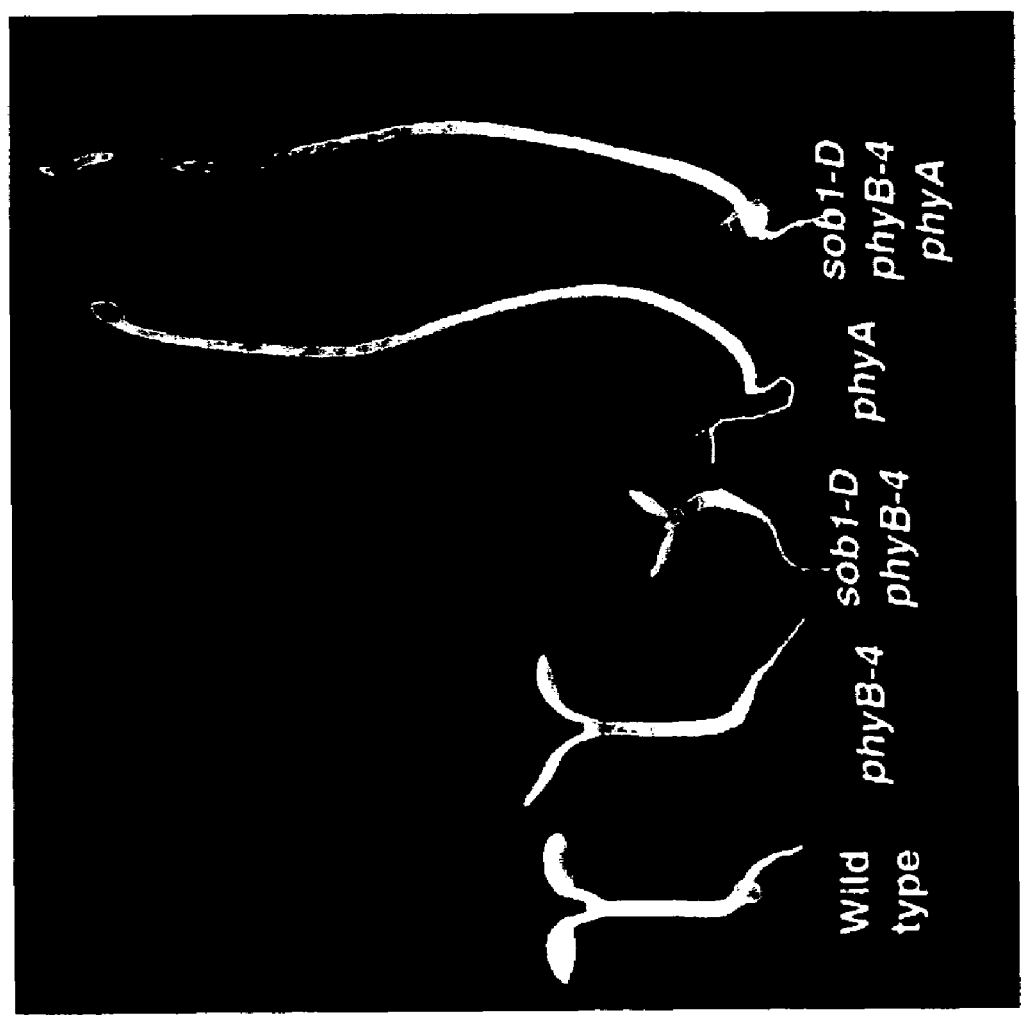
FIG. 10: The sob1-D mutant's hyper-responsivity to far-red light requires phyA.
Figure 11:
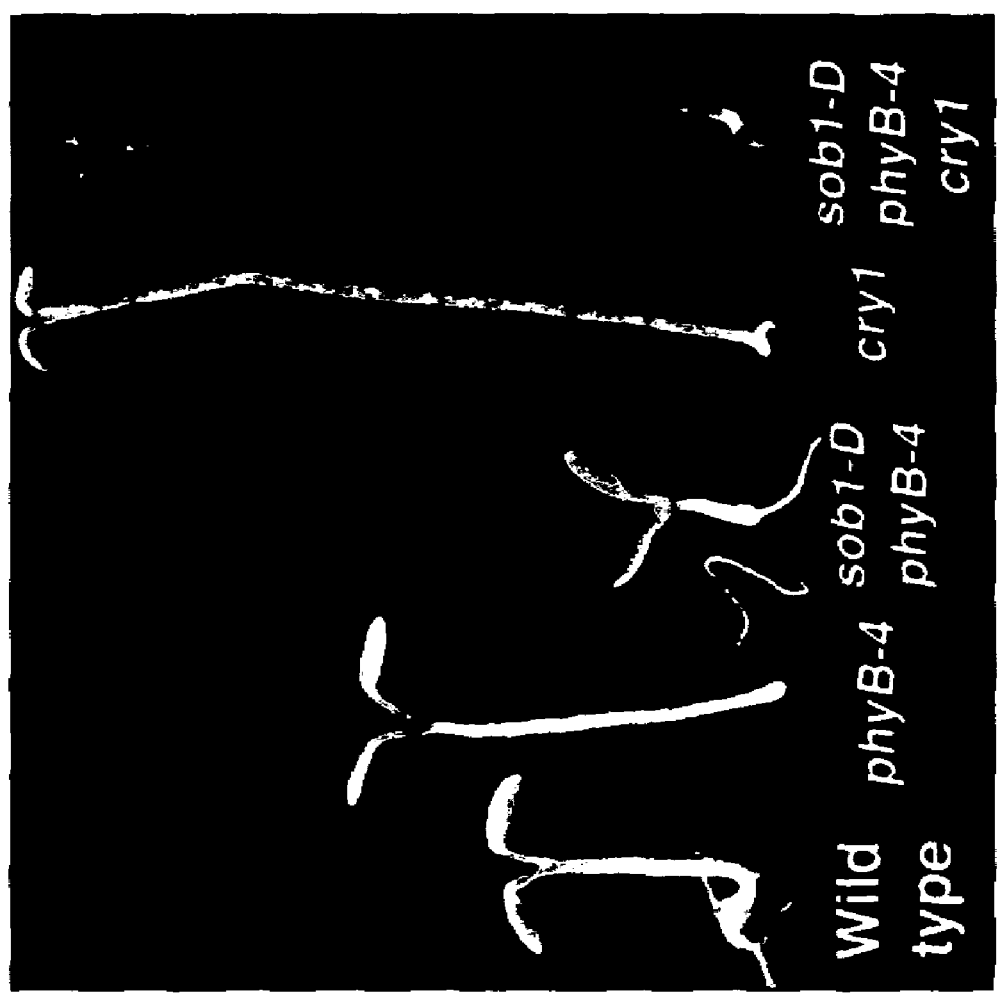
FIG. 11: The sob1-D mutant's hyper-responsivity to blue light requires cry1.

Though the sob1-D phyB-4 mutant has normal hypocotyl growth in the dark (FIG. 7), white-light grown seedlings are shorter than either phyB-4 or the wild type (FIGS. 1 and 7), suggesting that the sob1-D phyB-4 mutant is hyper-responsive to white light. Fluence response analysis in white light (FIG. 9) demonstrates that the sob1-D/OBP3-OX mutation confers hyper-responsivity to white light suggesting that this is the mechanism by which this mutation suppresses the long-hypocotyl phenotype of phyB-4mutants. Preliminary analysis shows that the sob1-D/OBP3-OX mutation also confers hyper-responsivity to far-red (FIG. 10) and blue light (FIG. 11). Genetic analysis indicates that the sob1-D-mediated hyper-responsivity to far-red light requires the far-red-light photoreceptor phyA (FIG. 10). Genetic analysis also indicates that the sob1-D-mediated hyper-responsivity to blue light requires the blue-light photoreceptor cry1 (FIG. 11). The sob1-D mutant's hyper-responsivity to white light does not require phyB since the sob1-D/OBP3-OX mutation can suppress the long-hypocotyl phenotype of a phyB-null allele (data not shown). Thus it appears that the sob1-D mutation is acting as bypass suppressor of the weak phyB-4 mutation via the amplification of phyA and cry1 mediated signal transduction.

Genomic DNA was isolated from rosette leaves of mature Arabidopsis thaliana plants, ecotype Col-O. The portions of the SOB1/OBP3 gene were amplified using the gene-specific primers with restriction endonuclease sites added onto the 5' end of each primer (SEQ ID NO:8)(5'-CGCGGATC-CGTGAAGGCGGAAGAGAATG-3', (SEQ ID NO:9) 5'-CCATCGATCATACATATCACCCACACCTC-3', (SEQ ID NO:10) 5'-CGGGGTACCATACATATCACCCACAC-CTC-3', and (SEQ ID NO:11) 5'-GACCTCGAGTGAAG-GCGGAAGAGAATG-3'). The restriction endonuclease sites were used to clone both of the fragments into the pHANNIBAL vector (CSIRO Plant Industry). The vector was constructed so that the 5' fragment was cloned in the sense direction and the 3' fragment was cloned in the antisense direction. The pHANNIBAL vector along with the fragments was then cloned into a binary vector, pART27 (CSIRO Plant Industry). An intron separating the two fragments is removed post-transcriptionally. After removal of the intron only a double stranded RNA of the fragments amplified from the SOB1/OBP3 gene exists, resulting in dominant RNAi-mediated inhibition of SOB1/OBP3 transcript accumulation. The SOB1/OBP3 gene contains a putative Dof domain at the 5' region of the gene. This domain is common in the family of Dof transcription factors in Arabidopsis. Therefore the portion of the gene which was used for the RNAi construct was the 3' end which is unique to SOB1/OBP3.

Figure 12:
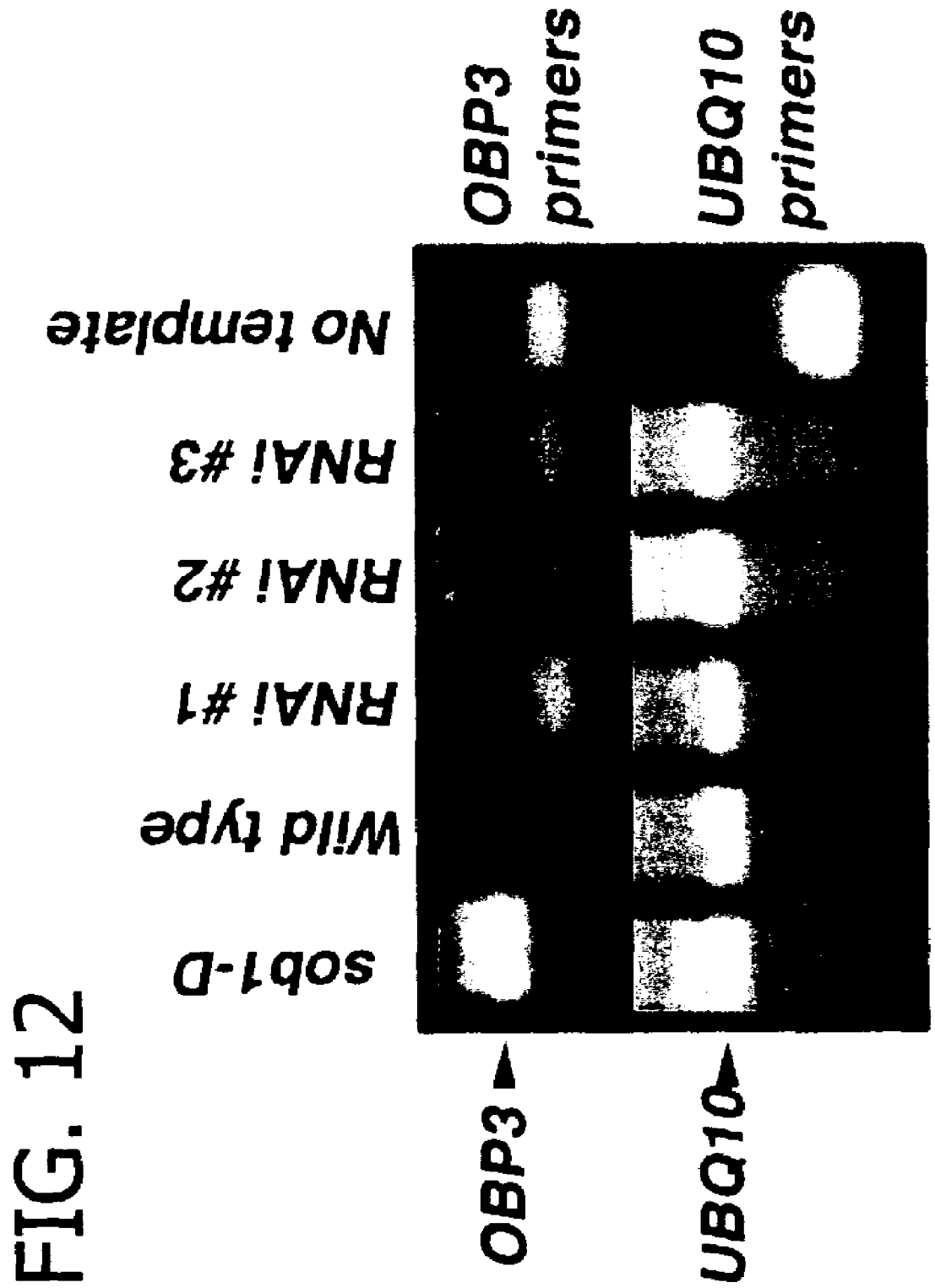
FIG. 12: Multiple OBP3 RNAi transgenic plants have reduced OBP3 transcript accumulation.
Figure 13:
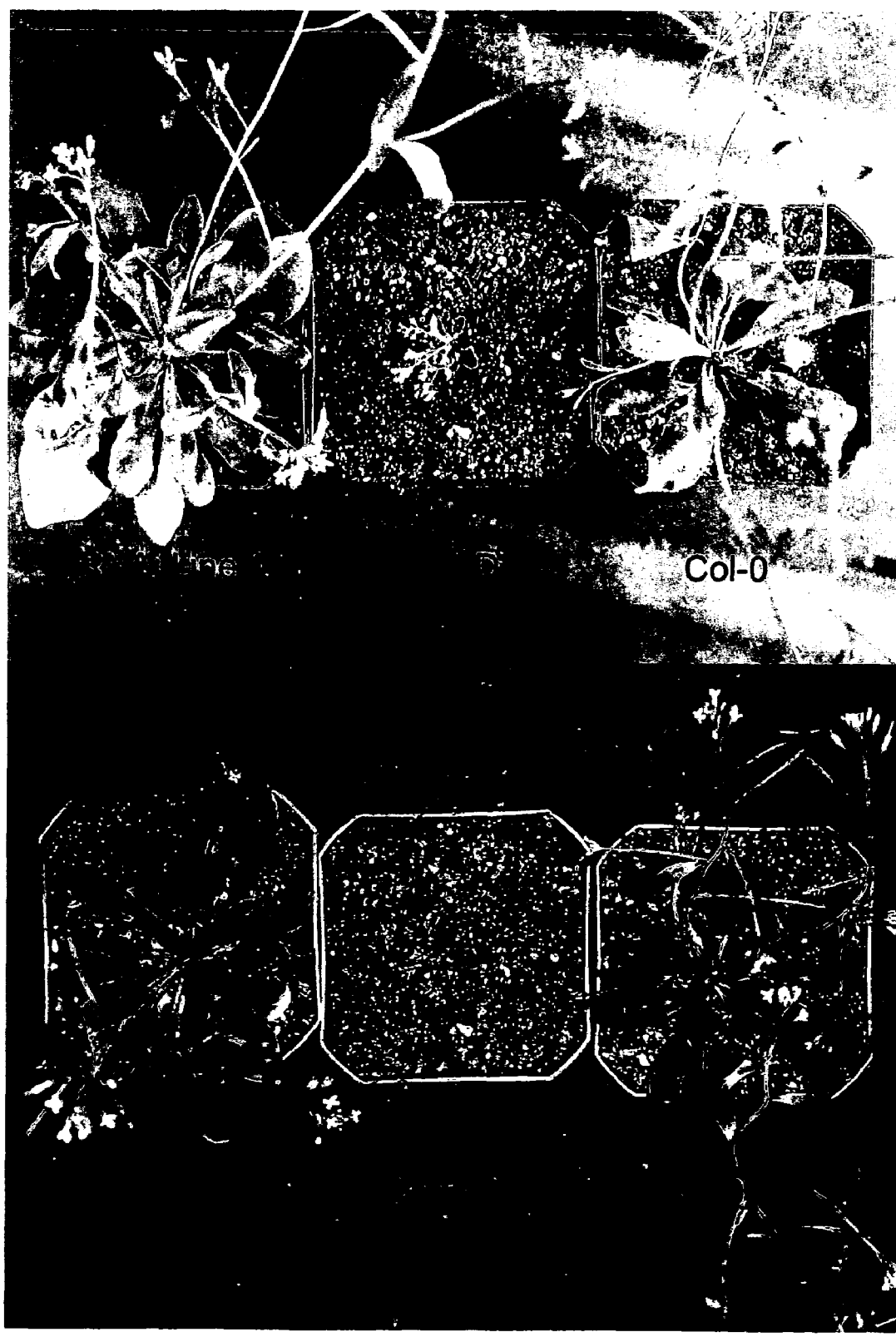
FIG. 13: OBP3 RNAi transgenic plants are larger than the wild-type.
Figure 14:
FIG. 14: Overexpression of OBP3 causes dwarfism in adult tobacco.
Figure 15:
FIG. 15: Overexpression of OBP3 causes dwarfism in adult tobacco.

Clearly the dominant phenotypes seen in the sob1-D phyB-4 mutant are the result of over-expression of SOB1/OBP3. However, since this mutant is caused by the over-expression of a gene, it is possible that these phenotypes are caused by sob1-D being a hypomorphic or neomorphic mutation causing ectopic expression (ie. at the wrong time or in the wrong place) of SOB1/OBP3. Thus, these dwarfing phenotypes may not be reminiscent of the actual role that OBP3 plays in plant development. To test this hypothesis, transgenic plants were generated with RNAi-mediated under-expression of SOB1/OBP3 (FIG. 12). Adult plants with reduced expression of SOB1/OBP3 are significantly larger than the wild type (FIG. 13). Thus for adult morphology, over-expression of SOB1/OBP3 leads to dwarf rosettes whereas under-expression of SOB1/OBP3 leads to plant with larger rosettes. These results demonstrate that the over- and under-expression of the SOB1/OBP3 gene can affect plant stature.

EXAMPLE 7

Tobacco Transformation

Nicotiana tabaccum cv. Samsun was used for transformation. The same Agrobacterium strains used for Arabidopsis transformation were grown over night until they had reach mid log phase growth. The cultures were diluted 1:10 in sterile water and were co-cultivated for 20 min. with leaf disks from sterile grown young tobacco plants. These disks were incubated on 2× growth media, 0.8% bactoagar (Difco Laboratories, Detroit Mich.) in continuous white light. After 48 hours, leaf disks were placed upside down on fresh plates of the same growth media supplemented with 0.4 mg/L of indoleacetic acid (IAA), 2 mg/L benzyl-aminopurine (hOBAP), 200 mg/L kanamycin and 500 mg/L carbenicillin. This media was replaced every 2 weeks. When shoots formed, they were removed from the leaf disk and placed on fresh media supplemented with just 200 mg/L kanamycin. Once roots formed, plants were transplanted into standard greenhouse conditions and grown until flowering. T2 seeds were sterilized for 30 min. in 10% (v/v) bleach with 0.05% triton X-100 then washed 3 times with sterile water and plated on 2× growth media, 0.8% bactoagar with or without 200 mg/L kanamycin.

EXAMPLE 8

General Methods for Altering the Size of a Plant

The Description of the Invention above provides a detailed outline for the various methods herein disclosed for altering the amount of OBP3 present in a plant. The Examples provide the results of applications of the methods herein described. The following is intended to provide a non-limiting summary of the typical steps employed when altering a plant using the present methods.

1. Select Plant

The present methods can be applied to any plant that can be altered using molecular techniques. As discussed above, there are numerous commercially exploited plants whose value would be increased by either shortening the time required for maturation into seed producing plants or where it is desirable to increase biomass or seed yield. The first step in applying the present methods is to select an appropriate plant. Although it is preferable to select a plant that has had methods for expression, transformation and regeneration developed, most plants, though applied effort, can be transformed and regenerated using methods known in the art.

As part of choosing a plant, one needs to choose whether to increase or decrease the desired size of a plant. As provided above, to increase the size of a plant, the plant is altered so as to contain a decreased amount of OBP3 while to decrease the size of a plant, the plant is altered so as to contain an increased amount of OBP3.

2. Chose the Alteration Method/target that is to be Employed

The second step may be to decide which method to employ to alter the plant. As provided above, the amount of OBP3 can be decreased by inactivating or decreasing the amount of the OBP3 gene while the amount of OBP3 can be increased by activating or increasing the gene activity within the cell.

OBP3 activity can be decreased by (1) the use of antisense expression units, (2) creating knockout mutations, (3) forcing the formation of triple helixes, and equivalent methods thereto.

OBP3 activity can be increased by (1) the use of OBP3 expression units, (2) increasing the activity of endogenous OBP3 and equivalent methods thereto.

3. Apply the Chosen Method to the Chosen Plant

Once a plant and target/methods are chosen, the skilled artisan simply alters the plant using the chosen method, such as those outlined herein, and plants are selected based on the level of OBP3, the expression of the transgene, phenotype and equivalent methods thereto.

It is to be understood that the present invention has been described in detail by way of illustration and example in order to acquaint others skilled in the art with the invention, its principles, and its practical application. Further, the specific embodiments of the present invention as set forth are not intended to be exhaustive or to limit the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims. While some of the examples and descriptions above include some conclusions about the way the invention may function, the inventors do not intend to be bound by those conclusions and functions, but put them forth only as possible explanations in light of current understanding.

The invention being thus described, it will be obvious that the same can be varied in many ways. Such variations are not be regarded as a departure from the spirit and scope of the present invention, and all such modifications and equivalents as would be obvious to one skilled in the art are intended to be included in the scope of the following claims. In addition, all references cited herein are hereby incorporated herein by reference.

What is claimed is:

1. A plant cell transformed by an expression vector comprising an isolated nucleic acid molecule in antisense orientation, wherein expression of said vector in the plant cell results in an increase in the size of the resulting plant as compared to a corresponding wild-type plant, and wherein the nucleic acid molecule comprises
    (a) the nucleotide sequence shown in SEQ ID NO:1, or the complement thereof or
    (b) a nucleotide sequence encoding the same amino acid sequence as said nucleotide sequence of (a), but which is degenerate in accordance with the degeneracy of the genetic code.

2. The transgenic plant cell of claim 1 wherein the nucleic acid molecule is SEQ ID NO: 1.

3. The transgenic plant cell of claim 1, wherein the resulting plant is a monocot.

4. The transgenic plant cell of claim 1, wherein the resulting plant is a dicot.

5. The transgenic plant cell of claim 1, wherein the resulting plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and forage crops.

6. A transgenic plant comprising the plant cell according to claim 1.

7. A seed produced by a transgenic plant comprising the plant cell according to claim 1, wherein the seed comprises the expression vector and is true breeding for an increase in the size of a daughter plant as compared to a wild-type variety of plant cell.

8. A recombinant antisense expression vector comprising:
    (a) a promoter functional in a plant cell; and
    (b) an isolated nucleic acid molecule comprising SEQ ID NO:1, wherein said nucleic acid molecule is operably linked in antisense orientation to said promoter.

9. A method for producing a transgenic plant having increased size as compared to the corresponding wild-type plant, said method comprising:
    (a) transforming plant cells by introducing the recombinant antisense expression vector as set forth in claim 8;
    (b) producing plants from said transformed cells and
    (c) selecting a whole plant exhibiting increased size.

10. A method for altering the size of the aerial portion of a plant without dwarfing root tissue, said method comprising:
    (a) introducing the recombinant antisense expression vector as set forth in claim 8 into a plant cell;
    (b) regenerating the plant cell into a transgenic plant;
    (c) evaluating the whole plant for an increase in size by comparing the plant with the introduced expression vector to a corresponding wild-type plant.

11. The method of claim 9, wherein the transgenic plant exhibits increased aerial tissue growth as compared to the corresponding wild-type plant.

12. A plant cell transformed with an isolated nucleotide sequence in antisense orientation, wherein the nucleotide sequence is SEQ ID NO:1 or the complement thereof, or a nucleic acid molecule encoding the same amino acid sequence as SEQ ID NO:1, but which is degenerate in accordance with the degeneracy of the genetic code, wherein expression of said nucleotide sequence in the plant cell results in an increase in the size of a resulting plant as compared to a corresponding wild-type plant.

13. The transgenic plant cell of claim 12, wherein the nucleotide sequence is SEQ ID NO:1.

14. A transgenic plant comprising the plant cell according to claim 12.

15. A seed produced by the transgenic plant of claim 14, wherein the seed comprises said isolated nucleotide sequence in antisense orientation.

16. The recombinant vector of claim 8, wherein the promoter is an inducible promoter.

17. The recombinant vector of claim 16, further comprising an enhancer element.

18. The recombinant vector of claim 17, wherein the enhancer element is from a CaMV35S promoter.

* * * * *